United States Patent [19]

Yaso et al.

[11] Patent Number: 4,877,877
[45] Date of Patent: Oct. 31, 1989

[54] 1-SUBSTITUTED ALKYL-2-OXO-HEXAHYDROQUINOXALINE DERIVATIVES

[75] Inventors: Masao Yaso; Yukio Suzuki; Kensuke Shibata; Eiichi Hayashi, all of Shizuoka, Japan

[73] Assignee: Toyo Jozo Kabushiki Kaisha, Shizuoka, Japan

[21] Appl. No.: 260,904

[22] Filed: Oct. 19, 1988

Related U.S. Application Data

[62] Division of Ser. No. 20,012, Feb. 25, 1987, Pat. No. 4,837,319.

[30] Foreign Application Priority Data

Feb. 25, 1986 [JP] Japan .................................. 61-38210

[51] Int. Cl.$^4$ .................. C07D 241/44; C07D 403/06; C07D 413/06; A61K 31/495
[52] U.S. Cl. ..................................................... 544/354
[58] Field of Search ......................................... 544/354

[56] References Cited

U.S. PATENT DOCUMENTS 4,292,240  9/1981  Lai et al. ............................. 544/349
4,296,114  10/1981  Appleton et al. .................... 544/354
4,837,319  6/1989  Yaso et al. ........................... 544/120

Primary Examiner—Mark L. Berch
Assistant Examiner—E. Bernhardt
Attorney, Agent, or Firm—Young & Thompson

[57] ABSTRACT

1-Substituted alkyl-2-oxo-hexahydroquinoxaline derivatives of the formula

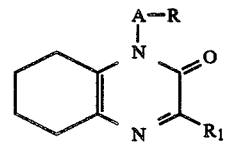

wherein A is lower alkylene; $R_1$ is selected from the group consisting of alkyl, phenyl-lower alkyl, and substituted phenyl-lower alkyl; and R is selected from the group consisting of hydroxyl, halogen, lower alkanocyloxy, $R_4$-carbamoyloxy and arylthio, in which $R_4$ is lower alkyl or aryl; and pharmaceutically acceptable salts thereof. The compounds are useful as agents for platelet aggregation inhibition, vasodilation and anti-lipoperoxide generation.

6 Claims, No Drawings

1-SUBSTITUTED ALKYL-2-OXO-HEXAHYDROQUINOXALINE DERIVATIVES

RELATION TO OTHER APPLICATION

The present application is a division of our copending application Ser. No. 07/020,012, filed Feb. 25, 1987, now U.S. Pat. No. 4,837,319.

BACKGROUND OF THE INVENTION

This invention relates to novel 1-substituted alkyl-2-oxo-hexahydro quinoxaline derivatives, which are useful as pharmaceuticals for treating circulatory and metabolic disorders. The compounds of the invention are active as platelet aggregation inhibiting, vasodilating and/or antilipoperoxide generating agents.

Recently, a significant number of compounds having platelet aggregation inhibiting activity have been reported. Of these, the only known compounds having a pyrazine ring as the basic structure are tetramethyl pyrazine (16th Heterocyclic Chemistry Symposium (Osaka) pp. 65–68 (1984)) and 2-higher fatty acid acyloxymethyl pyrazine (Jap. Pat. Unexam. Publ. No. 59-219269).

It is of great importance to discover high quality pharmaceuticals having stronger inhibitory activities for platelet aggregation, in order effectively to treat circulatory and metabolic disorders.

We have found that 1-substituted alkyl-2-oxo-hexahydroquinoxaline derivatives display inhibitory action on platelet aggregation, vasodilation activity and/or antilipoperoxide generation, and are expected to have excellent pharmaceutical properties.

SUMMARY OF THE INVENTION

In the present invention, a compound of the formula

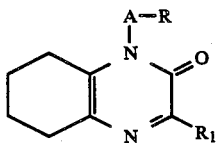

(1)

is provided, wherein R is hydroxyl, halogen, lower alkanoyloxy, $R_4$-carbamoyloxy or arylthio, in which $R_4$ is lower alkyl or aryl, A is lower alkylene, and $R_1$ is alkyl or phenyl-lower alkyl optionally substituted.

The compound [1] can be provided in salt form. The salts must be pharmacologically acceptable non-toxic salts thereof. Examples of such salts are salts of an inorganic acid such as hydrochloric, sulfuric, or phosphoric, and salts of an organic acid such as acetic, propionic, butyric, glycolic, gluconic, malic, tartaric, succinic, mandelic, aspartic, glutaric, methanesulfonic or toluenesulfonic. Salts of other known acids can be used as well.

DETAILED DESCRIPTION OF THE INVENTION

The compound [1] can be produced by the following processes:

Process A

A process for production of compound [1] wherein R is hydroxyl, and the compound produced thus has the formula

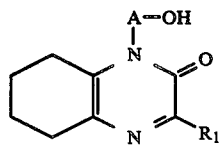

(1a)

wherein $R_1$, and A are defined as above.

The above compound [1a] can be produced by reacting a compound of the formula

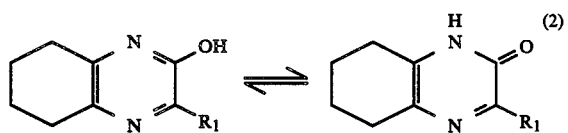

(2)

wherein $R_1$, is are defined as above, with a hydroxyalkyl halide of the formula

X—A—OH where X is halogen and A is defined as above, in an organic solvent.

In the compound [2] above, $R_1$ is alkyl, optionally substituted phenyl, or optionally substituted phenyl-lower alkyl. "Alkyl", as used above, is defined as saturated or unsaturated $C_{1-20}$ alkyl, which may be branched or unbranched. Examples are methyl, ethyl, propyl, isopropyl, butyl, isobutyl, sec-butyl, t-butyl, pentyl, isopentyl, hexyl, heptyl, octyl, nonyl, decyl, undecyl, dodecyl, tridecyl, tetradecyl, pentadecyl or hexadecyl. "Optionally substituted phenyl", as used above, is defined as phenyl or phenyl substituted with $C_{1-3}$ lower alkyl, halogen, nitro, or lower alkoxy. "Optionally substituted phenyl-lower alkyl", as used above, is defined as phenyl or phenyl substituted with $C_{1-3}$ lower alkyl, halogen, nitro or lower alkoxy, in which lower alkyl means methyl, 2-ethyl, 1-ethyl, 3-propyl or 1-propyl. Examples are benzyl, p-chlorobenzyl, 2-phenylethyl and 1-phenylethyl.

The compound [2], i.e. a 2-hydroxy-3-substituted-hexahydro quinoxaline derivative, is produced by the process developed by the present inventors, in which an α-amino acidamide, other than glycine, is reacted with 1,2-cyclohexanedione in an alkaline medium.

The group A in the above hydroxylalkyl halide is defined as above, namely, lower alkylene. Examples of lower alkylene are methylene, ethylene, methylmethylene, propylene, 1-methylethylene, 1,1-dimethylmethylene or 1-ethylmethylene; ethylene is preferred.

The group X in the above hydroxyalkyl halide is halogen, such as chlorine or bromine, and in general chlorine is preferred. The preferred hydroxyalkyl halide is ethylene chlorohydrin.

Reaction of the compound [3] with hydroxyalkyl halide proceeds in an organic solvent such as butanol.

The above reaction is preferably effected in an aqueous alkali solvent such as hydroxy alkali, and preferably, is possible, under heating. Isolation of the product [1a] can be performed by adding water to the reaction mixture and extracting with water-immiscible organic solvent.

Process B

A process for production of compound [1] wherein R is lower alkanoyloxy (hereinafter designated as compound [1b]):

A compound [1b] can be produced by acylating an above compound [1a] with lower fatty acid or its reactive derivative.

Examples of lower fatty acid are branched or unbranched $C_{1-6}$ fatty acids such as acetic acid, propionic acid, butyric acid, isobutyric acid, sec-butyric acid, valeric acid, isovaleric acid and hexanoic acid. Examples of reactive derivatives are known acylating agents for the hydroxyl group, such as acid halide, acid anhydride, mixed anhydride or active ester. The lower fatty acid can itself be acylated in the presence of a condensation reagent such as N,N-dicyclohexyl carbodiimide (DCC).

In the above reactions, co-generated acid can be removed by an acid-binder, for example a known tertiary organic amine such as pyridine or triethylamine.

The product [1b] can be isolated by pouring the reaction mixture into dilute aqueous alkali and extracting with water-immiscible organic solvent.

Process C

A process for production of compound [1] wherein R is $R_4$-carbamoyloxy (hereinafter designated as a compound [1c]):

A compound [1c] can be produced by reacting the above compound [1a] with lower alkyl isocyanate or aryl isocyanate.

"Lower alkyl" in the above lower alkyl carbamoyloxy mens branched or unbranched $C_{1-6}$ alkyl, and "aryl" in the above aryl carbamoyloxy means phenyl or phenyl substituted with $C_{1-3}$ lower alkyl, halogen, nitro or lower alkoxy.

Reaction of the compound [1a] and the isocyanate compound proceeds in an organic solvent such as pyridine. Isolation of the product [1c] can be effected by removing solvent from the reaction mixture and extracting the resultant residue with an inert organic solvent in an aqueous medium, or precipitating the product [1c] by adding solvent such as ether.

Process D

A process for production of compound [1] wherein R is halogen, and the compound produced thus has the formula

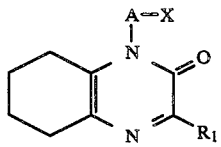

(1d)

wherein X is halogen, and A and $R_2$ are defined as above.

A compound [1d] can be produced by halogenating the compound [1a] above with halogenating agent.

The said halogenating agent may be any known halogenating agent. More specifically, known chlorination reagents or bromination reagents can be used. Conventional chlorination reagents such as $SOCl_2$, $PCl_5$ and $POCl_3$ can be applied. The halogenation reaction can be effected, in general, in an inert organic solvent such as chloroform. Reaction proceeds at room temperature. Isolation of the product [1d] can be performed by adding a water-immiscible organic solvent such as chloroform, washing with dilute aqueous alkali, dehydrating the organic layer and removing the solvent therefrom.

The compound [1d] can be used without purification, as by silica-gel column chromatography.

Process E

A process for production of compound [1] wherein R is arylthio (hereinafter designated as compound [1]):

A compound [1e] can be produced by reacting the above compound [1d] with an alkali metal salt of arylmercaptan in an organic solvent.

"Aryl" in the above arylthio means phenyl or phenyl substituted with $C_{1-3}$ lower alkyl, halogen, nitro or lower alkoxy.

Examples of the above alkali salts of arylmercaptan are the corresponding sodium and potassium salts.

Reaction of the above compound [1d] and the said alkali metal salt of the mercapto compound proceeds, in general, in an organic solvent such as dimethyl formamide (DMF). Isolation of the product [1e] can be performed by removing the reaction solvent and extracting the residue with water-immiscible organic solvent in the presence of dilute aqueous alkali.

The thus-obtained compound [1] is purified, if required, by column chromatography using silica-gel, activated alumina or adsorption resin with elution solvent such as chloroform-methanol or benzene-ethyl acetate.

A compound [1] is generally produced in the form of its free base, but it can also be produced in the form of a conventional salt thereof. For example, a hydrochloride can be prepared by dissolving a compound [1] in a lower alcohol such as methanol or ethanol, adding a slight molar excess of hydrochloric acid, and isolating the precipitated material, or if not precipitated, by adding ether therein to precipitate. The molar ratio of hydrochloric acid may be different according to the specific compound [1].

Examples of the compound [1] of the present invention are set forth in Table 1.

TABLE 1

[Structure: pyrazinone-type core with substituents R₁, R₂, R₃ on ring and N-A-R substituent]

| Compound No. | R₁ | R₂ | R₃ | A | R |
|---|---|---|---|---|---|
| 018 | Me | Me | Me | —CH₂CH₂— | —N(CH₂CH₂)₂CH₂ (piperidinyl) |
| 019 | Me | Me | Me | " | —N(CH₂CH₂)₂O (morpholinyl) |
| 020 | Me | Me | Me | " | —N(CH₂CH₂)₂N—Me |
| 021 | Me | Me | Me | " | —N(CH₂CH₂)₂N—CH₂CH₂—OH |
| 022 | Me | Me | Me | " | 1-imidazolyl |
| 023 | Me | Me | Me | " | —N(CH₂CH₂)₂N—CH₂Ph |
| 024 | Me | Me | Me | " | —N(CH₂CH₂)₂N—CH₂Ph—Cl (p)CH₂ |
| 025 | Me | Me | Me | " | —N(CH₂CH₂)₂N—CH₂Ph—Cl (o) |
| 026 | Me | Me | Me | " | —OH |
| 027 | Me | Me | Me | " | —S—Ph |
| 028 | Me | Me | Me | " | —S—(1-methyltetrazole-5-yl) |
| 061 | Me | Me | Me | —CH₂CH₂— | —O—CO—Me |
| 062 | Me | Me | Me | " | —O—CONH—Me |
| 063 | Me | Me | Me | " | —O—CONH—Ph |
| 064 | Me | Me | Me | " | —O—CONH—Ph—Cl (p) |
| 101 | Me | Me | Me | " | —N(CH₂CH₂)₂N—CH₂CH₂—N(pyrazinone with Me substituents) |
| 109 | Ph | Me | Me | " | —OH |
| 110 | Ph | Me | Me | " | —N(CH₂CH₂)₂O (morpholinyl) |

TABLE 1-continued $$\begin{array}{c} \text{structure with } R_3, R_2, R_1, \text{ and } A-R \text{ substituents on pyrazinone ring} \end{array}$$

| Compound No. | R₁ | R₂ | R₃ | A | R |
|---|---|---|---|---|---|
| 111 | Ph | Me | Me | " | —N(piperazine)N—CH₂Ph—Cl (p)CH₂ |
| 112 | —CH₂Ph | Me | Me | " | —OH |
| 113 | " | Me | Me | " | —N(morpholine)O |
| 114 | " | Me | Me | " | —N(piperazine)N—CH₂Ph |
| 115 | " | Me | Me | " | —N(piperazine)N—CH₂Ph—Cl (p)CH₂ |
| 116 | " | Me | Me | " | —N(piperazine)N—CH₂Ph—Cl (o) |
| 117 | Pro | —(CH₂)₄— | | " | —N(piperazine)N—CH₂CH₂—OH |
| 118 | Pro | " | | " | —N(morpholine)O |
| 119 | Pro | " | | " | —N(piperazine)N—CH₂Ph |
| 120 | Pro | —(CH₂)₄— | —CH₂CH₂— | | —N(piperazine)N—CH₂Ph—Cl (p)CH₂ |
| 121 | Pro | Me | Me | " | —N(morpholine)O |
| 122 | Pro | Me | Me | " | —N(piperazine)N—CH₂Ph |
| 123 | iso-Bu | Me | Me | " | —N(morpholine)O |

TABLE 1-continued

Structure:

$$\begin{array}{c} A-R \\ R^3 \diagdown N \diagup O \\ R_2 \diagdown \diagup N \diagdown R_1 \end{array}$$

| Compound No. | R₁ | R₂ | R₃ | A | R |
|---|---|---|---|---|---|
| 124 | " | Me | Me | " | —N(CH₂CH₂)₂N—CH₂Ph |
| 125 | " | Me | Me | " | —N(CH₂CH₂)₂N—CH₂Ph—Cl (p)CH₂ |
| 126 | " | Me | Me | " | —N(CH₂CH₂)₂N—CH₂Ph—Cl (m) |
| 127 | " | —(CH₂)₄— | | " | —N(CH₂CH₂)₂O |
| 128 | " | " | | " | —N(CH₂CH₂)₂N—CH₂Ph |
| 129 | " | " | | " | —N(CH₂CH₂)₂N—CH₂Ph—Cl (m) |
| 130 | Pro | Et | Et | " | —N(CH₂CH₂)₂O |
| 131 | Pro | Et | Et | " | —N(CH₂CH₂)₂N—CH₂Ph |
| 132 | Pro | Et | Et | " | —N(CH₂CH₂)₂N—CH₂Ph—Cl (p)CH₂ |
| 133 | Pro | Et | Et | " | —N(CH₂CH₂)₂N—CH₂Ph—Cl (m) |
| 134 | Pro | Et | Et | " | —N(CH₂CH₂)₂N—CH₂Ph—Cl (o) |
| 141 | Bu | —(CH₂)₄— | | —CH₂CH₂— | —N(CH₂CH₂)₂O |

TABLE 1-continued

[Structure: pyrazinone with R³, R², N, N, R₁, A-R, O substituents]

| Compound No. | R₁ | R₂ | R₃ | A | R |
|---|---|---|---|---|---|
| 142 | Bu | | " | " | —N⌐⌐N—CH₂Ph |
| 143 | Bu | | " | " | —N⌐⌐N—CH₂Ph—Cl (p)CH₂ |
| 144 | Bu | | " | " | —N⌐⌐CH₂ |
| 145 | Bu | | " | " | —N⌐⌐N—CH₂CH₂—OH |
| 146 | Bu | | " | " | —N⌐⌐N—CH₂Ph—F (p) |
| 147 | CH₂Ph | Me | Me | " | —OCO—Me |
| 148 | iso-Pro | Me | Me | " | —N⌐⌐O |
| 149 | " | Me | Me | " | —N⌐⌐N—CH₂Ph |
| 150 | " | Me | Me | " | —N⌐⌐N—CH₂Ph—Cl (p)CH₂ |
| 151 | " | Me | Me | " | —N⌐⌐N—CH₂Ph—F (p) |
| 152 | sec-Bu | Me | Me | " | —N⌐⌐O |
| 153 | " | Me | Me | " | —N⌐⌐N—CH₂Ph |
| 154 | " | Me | Me | " | —N⌐⌐N—CH₂Ph—Cl (p)CH₂ |

TABLE 1-continued
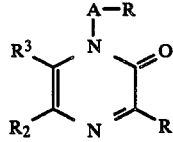
| Compound No. | R₁ | R₂ | R₃ | A | R |
|---|---|---|---|---|---|
| 155 | " | Me | Me | " | −N☐N−CH₂Ph−F (p) |
| 156 | Bu | Me | Me | " | −N☐O |
| 157 | Bu | Me | Me | −CH₂CH₂− | −N☐N−CH₂Ph |
| 158 | Bu | Me | Me | " | −N☐N−CH₂Ph−Cl (p)CH₂ |
| 159 | iso-Pro | Et | Et | " | −N☐O |
| 160 | " | Et | Et | " | −N☐N−CH₂Ph |
| 161 | " | Et | Et | " | −N☐N−CH₂Ph−Cl (p)CH₂ |
| 162 | " | Et | Et | " | −N☐N−CH₂Ph−F (p) |
| 163 | " | Et | Et | " | −N☐CH₂ |
| 164 | " | Et | Et | " | −N☐N−CH₂CH₂−OH |
| 165 | " | Et | Et | " | −N☐N−CH₂Ph−Cl (m) |
| 166 | iso-Bu | Et | Et | " | −N☐N−CH₂Ph−F (p) |

TABLE 1-continued $$\text{structure with } R^3, R_2, N, N(A-R), C=O, R_1$$

| Compound No. | R₁ | R₂ | R₃ | A | R |
|---|---|---|---|---|---|
| 167 | " | Et | Et | " | —N☐O (morpholino) |
| 168 | " | Et | Et | " | —N☐N—CH₂Ph—Cl (p)CH₂ |
| 170 | " | Et | Et | " | —N☐N—CH₂Ph |
| 171 | sec-Bu | Et | Et | " | —N☐CH₂ |
| 172 | " | Et | Et | " | —N☐N—CH₂CH₂—OH |
| 173 | sec-Bu | Et | Et | —CH₂CH₂— | —N☐O |
| 174 | " | Et | Et | " | —N☐N—CH₂Ph |
| 175 | " | Et | Et | " | —N☐N—CH₂Ph—F (p) |
| 176 | " | Et | Et | " | —N☐N—CH₂Ph—Cl (p) |
| 177 | " | Et | Et | " | —N☐N—CH₂Ph—Cl (m) |
| 178 | " | Et | Et | " | —N☐N—CH₂Ph—Cl (o) |
| 179 | Bu | Et | Et | " | —N☐N—CH₂Ph |

TABLE 1-continued

[Structure with R³, R², A—R, N, N, R₁, O]

| Compound No. | R₁ | R₂ | R₃ | A | R |
|---|---|---|---|---|---|
| 180 | Bu | Et | Et | " | —N(piperazine)N—CH₂Ph—Cl (p) |
| 181 | Bu | Et | Et | " | —N(piperidine)CH₂ |
| 182 | Bu | Et | Et | " | —N(morpholine)O |
| 183 | Bu | Et | Et | " | —N(piperazine)N—CH₂Ph—F (p) |
| 185 | Bu | Et | Et | " | —N(piperazine)N—CH₂Ph—Cl (m) |
| 187 | Et | Et | Et | " | —N(morpholine)O |
| 188 | Et | Et | Et | " | —N(piperazine)N—CH₂Ph—Cl (p) |
| 189 | Et | Et | Et | " | —N(piperazine)N—CH₂Ph |
| 190 | Et | Me | Me | —CH₂CH₂— | —N(morpholine)O |
| 191 | Et | Me | Me | " | —N(piperazine)N—CH₂Ph—Cl (p) |
| 192 | Et | Me | Me | " | —N(piperazine)N—CH₂Ph—F (p) |
| 193 | Et | Me | Me | " | —N(piperazine)N—CH₂Ph—OMe (p) |

TABLE 1-continued

Structure:

$$R^3, R_2 \text{ on ring with } N-A-R, \text{ C=O, } N, R_1$$

| Compound No. | R₁ | R₂ R₃ | A | R |
|---|---|---|---|---|
| 250 | —(CH₂)₄CH₃ | —(CH₂)₄— | " | —N◯N—CH₂Ph—Cl (p) |
| 251 | " | " | " | —N◯N—CH₂Ph—F (p) |
| 252 | " | " | " | —N◯O |
| 253 | " | " | " | —N◯N—Bu |
| 254 | " | " | " | —N◯N—CH₂Ph—OMe (p) |
| 255 | —(CH₂)₅CH₂ | " | " | —N◯O |
| 256 | " | " | " | —N◯N—CH₂Ph—Cl (p) |
| 257 | " | " | " | —N◯N—CH₂Ph—NO₂ (p) |
| 258 | " | " | " | —N◯N—CH₂Ph—F (p) |
| 259 | —(CH₂)₆CH₃ | " | " | —N◯O |
| 260 | " | " | " | —N◯N—CH₂Ph—Cl (p) |
| 261 | —(CH₂)₆CH₂ | —(CH₂)₄— | —CH₂CH₂— | —N◯N—CH₂Ph—NO₂ (p) |

TABLE 1-continued

| Compound No. | R₁ | R₂ | R₃ | A | R |
|---|---|---|---|---|---|
| 262 | " | | " | " | —N⟨piperazine⟩N—CH₂Ph—F (p) |
| 263 | " | | " | " | —N⟨piperazine⟩N—Bu |
| 264 | " | | " | " | —N⟨3,5-dimethylpiperazine⟩N—CH₂Ph—Cl (p) |
| 265 | —(CH₂)₇CH₃ | | " | " | —N⟨morpholine⟩O |
| 266 | " | | " | " | —N⟨piperazine⟩N—CH₂Ph—Cl (p) |
| 267 | " | | " | " | —N⟨piperazine⟩N—CH₂Ph—OMe (p) |
| 268 | " | | " | " | —N⟨piperazine⟩N—CH₂Ph—NO₂ (p) |
| 269 | " | | " | " | —N⟨piperazine⟩N—CH₂Ph—F (p) |
| 270 | " | | " | " | —N⟨3,5-dimethylpiperazine⟩N—CH₂Ph—F (p) |
| 271 | —(CH₂)₈CH₃ | | " | " | —N⟨morpholine⟩O |
| 272 | " | | " | " | —N⟨piperazine⟩N—CH₂Ph—Cl (p) |
| 273 | " | | " | " | —N⟨piperazine⟩N—CH₂Ph—F (p) |

TABLE 1-continued

| Compound No. | R₁ | R₂ | R₃ | A | R |
|---|---|---|---|---|---|
| 274 | " | | " | " | —N(piperazine)N—CH₂Ph—NO₂ (p) |
| 275 | " | | " | " | —N(piperazine)N—CH₂Ph—OMe (p) |
| 276 | —(CH₂)₁₁CH₃ | —(CH₂)₄— | | —CH₂CH₂— | —N(morpholine)O |
| 277 | " | | " | " | —N(piperazine)N—CH₂Ph—Cl (p) |
| 278 | " | | " | " | —N(homopiperazine)N—CH₂Ph—F (p) |
| 279 | " | | " | " | —N(piperazine)N—CH₂Ph—NO₂ (p) |
| 280 | —(CH₂)₁₃CH₃ | | " | " | —N(morpholine)O |
| 281 | " | | " | " | —N(piperazine)N—CH₂Ph—OMe (p) |
| 282 | " | | " | " | —N(homopiperazine)N—CH₂Ph—F (p) |
| 283 | (CH₂)₁₅CH₃ | | " | " | —N(morpholine)O |
| 284 | " | | " | " | —N(piperazine)N—CH₂Ph—Cl (p) |
| 285 | " | | " | " | —N(piperazine)N—CH₂Ph—NO₂ (p) |

TABLE 1-continued

| Compound No. | R₁ | R₂ | R₃ | A | R |
|---|---|---|---|---|---|
| 286 | " | | " | " | —N(piperazine)N—CH₂Ph—Cl (p) |
| 287 | Et | Me | Me | " | —N(piperazine)N—CH₂Ph |
| 288 | Et | Me | Me | " | —N(piperazine)N—CH₂Ph—Cl (p) |
| 289 | Et | Me | Me | " | —N(piperazine)N—CH₂Ph—F (p) |
| 290 | Et | Me | Me | " | —N(piperazine)N—CH₂Ph—NO₂ (p) |
| 291 | —CH₂Ph | Et | Et | —CH₂CH₂— | —N(morpholine)O |
| 292 | " | Et | Et | " | —N(piperidine)CH₂ |
| 293 | " | Et | Et | " | —N(piperazine)N—CH₂Ph |
| 294 | " | Et | Et | " | —N(piperazine)N—CH₂Ph—Cl(p) |
| 295 | " | Et | Et | " | —N(piperazine)N—CH₂Ph—Cl₂(2,4) |
| 296 | " | Et | Et | " | —N(piperazine)N—CH₂Ph—F(p) |
| 297 | " | Et | Et | " | —N(piperazine)N—CH₂Ph—OMe(p) |

TABLE 1-continued $$\text{structure with } R^3, R_2, R_1, \text{ N-A-R, =O}$$

| Compound No. | R₁ | R₂ | R₃ | A | R |
|---|---|---|---|---|---|
| 305 | —(CH₂)₅CH₃ | —(CH₂)₄— | | " | —N⌷N—Ph |
| 306 | " | " | | " | —N⌷N—CH₂Ph |
| 307 | " | " | | " | —N⌷N—CH₂Ph—F(p) |
| 308 | " | " | | " | —N⌷N—CH₂Ph—OMe(p) |
| 309 | " | " | | " | —N⌷N—Ph—Cl(o) |
| 310 | " | " | | " | —N⌷N—Ph—OMe(o) |
| 311 | " | " | | " | —N⌷N—CH₂Ph—NO₂(p) |
| 312 | " | " | | " | —N⌷N—CH₂Ph—Cl(p) |
| 313 | —(CH₂)₅CH₃ | —(CH₂)₄— | | —CH₂CH₂— | —N⌷N—CH₂Ph—OMe(p) |
| 314 | —(CH₂)₆CH₃ | " | | " | —N⌷N—CH₂Ph |
| 315 | " | " | | " | —N⌷N—Ph |
| 316 | " | " | | " | —N⌷N—Ph—OMe(o) |

TABLE 1-continued

| Compound No. | R₁ | R₂ | R₃ | A | R |
|---|---|---|---|---|---|
| 317 | " | | " | " | —N◯N—Ph—Cl(o) |
| 318 | " | | " | " | —N◯N—CH₂Ph—F(p) |
| 319 | " | | " | " | —N◯N—CH₂Ph—OMe(p) |
| 320 | " | | " | " | —N◯N—CH₂Ph—NO₂(p) |
| 321 | —(CH₂)₇CH₃ | | " | " | —N◯N—CH₂Ph |
| 322 | " | | " | " | —N◯N—Ph |
| 323 | " | | " | " | —N◯N—Ph—OMe(o) |
| 324 | " | | " | " | —N◯N—Ph—Cl(o) |
| 325 | " | | " | " | —N◯N—CH₂Ph—NO₂(p) |
| 326 | " | | " | " | —N◯N—CH₂Ph—OMe(p) |
| 327 | " | | " | " | —N◯N—CH₂Ph—Cl(p) |
| 328 | —(CH₂)₈CH₃ | —(CH₂)₄— | | =CH₂CH₂— | —N◯N—CH₂Ph |

TABLE 1-continued

Structure: pyrazinone with R³, R² on ring, N-A-R substituent, R¹ on C=N carbon, C=O group.

| Compound No. | R₁ | R₂ | R₃ | A | R |
|---|---|---|---|---|---|
| 329 | " | | " | " | —N(piperazine)N—CH₂Ph—Cl(p) |
| 330 | " | | " | " | —N(homopiperazine)N—CH₂Ph—NO₂(p) |
| 331 | " | | " | " | —N(homopiperazine)N—CH₂Ph—F(p) |
| 332 | " | | " | " | —N(homopiperazine)N—CH₂Ph—OMe(p) |
| 334 | —(CH₂)₉CH₃ | | " | " | —N(morpholine)O |
| 335 | " | | " | " | —N(piperazine)N—CH₂Ph |
| 336 | " | | " | " | —N(homopiperazine)N—Ph |
| 337 | " | | " | " | —N(piperazine)N—CH₂Ph—OMe(p) |
| 338 | " | | " | " | —N(piperazine)N—CH₂Ph—Cl(p) |
| 339 | " | | " | " | —N(homopiperazine)N—CH₂Ph—NO₂(p) |
| 340 | " | | " | " | —N(homopiperazine)N—CH₂Ph—Cl(p) |
| 374 | —CH₂Ph | Et | Et | " | —N(piperidine)CH—Ph |

TABLE 1-continued

Structure:

R³, R², N (ring), R₁, with N-A-R and C=O substituents on the pyrazinone ring.

| Compound No. | R₁ | R₂ | R₃ | A | R |
|---|---|---|---|---|---|
| 375 | " | Et | Et | " | —N(ring)CH—Me |
| 378 | " | Et | Et | " | —N(ring)N—CH₂Ph—NO₂(p) |
| 380 | —CH₂Ph | Et | Et | —CH₂CH₂— | —N(ring)N—Ph |
| 384 | —CH₂Ph—Cl(p) | Et | Et | " | —N(ring)O |
| 385 | " | Et | Et | " | —N(ring)N—CH₂Ph—Cl(p) |
| 386 | " | Et | Et | " | —N(ring)N—CH₂Ph—OMe(p) |
| 387 | " | Et | Et | " | —N(ring)N—CH₂Ph—NO₂(p) |
| 454 | Et | Me | Me | " | —N(ring)NH |
| 455 | Et | Me | Me | " | —N(ring)N—CO—CH₂Ph |
| 456 | Et | Me | Me | " | —N(ring)N—CH₂Ph—Cl(p) |
| 457 | Et | Me | Me | " | —N(ring)N—CO—CH₂—(2-    ) |
| 458 | Et | Me | Me | " | —N(ring)N—CO—Ph—NO₂(p) |

TABLE 1-continued structure (heading): R³, R², N, N, A—R, O, R₁

| Compound No. | R₁ | R₂ | R₃ | A | R |
|---|---|---|---|---|---|
| 459 | Et | Me | Me | " | —N◯N—CO—CH₂Ph—NO₂(p) |
| 460 | Et | Me | Me | " | —N◯N—CO—Ph—OMe(p) |
| 461 | Et | Me | Me | " | —N◯N—CO—Ph—OMe₂(2,3) |
| 462 | Et | Me | Me | " | —N◯N—CO—Ph—OMe₂(2,4) |
| 463 | Et | Me | Me | " | —N◯N—CO—Ph—OMe₂(3,4) |
| 464 | Et | Me | Me | —CH₂CH₂— | —N◯N—CO—Ph—OMe₃(3,4,5) |
| 465 | Et | Me | Me | " | —N◯N—SO₂—Ph—Cl(p) |
| 467 | CH₂Ph—Cl(p) | Et | Et | " | —N◯N—CH₂Ph |
| 470 | CH₂Ph | —(CH₂)₄— | | " | —N◯O |
| 471 | " | " | | " | —N◯N—CH₂Ph |
| 472 | " | " | | " | —N◯N—Ph |
| 473 | " | " | | " | —N◯N—CH₂Ph—Cl(p) |

TABLE 1-continued

Structure:
R³ and R² on a pyrazine-like ring with N-A-R substituent and =O; R₁ on the ring.

| Compound No. | R₁ | R₂ | R₃ | A | R |
|---|---|---|---|---|---|
| 474 | " | | " | " | −N⏉N−CH₂Ph−OMe(p) (piperazine) |
| 475 | " | | " | " | −N⏉N−CH₂Ph−F(p) (piperazine) |
| 476 | CH₂CH₂Ph | | " | " | −N⏉O (morpholine) |
| 477 | " | | " | " | −N⏉N−CH₂Ph (piperazine) |
| 478 | " | | " | " | −N⏉N−Ph (piperazine) |
| 479 | " | | " | " | −N⏉N−CH₂Ph−Cl(p) (piperazine) |
| 480 | " | | " | " | −N⏉N−CH₂Ph−OMe(p) (piperazine) |
| 481 | Et | −(CH₂)₄− | −CH₂CH₂− | | −N⏉O (morpholine) |
| 482 | Et | −(CH₂)₄− | −CH₂CH₂− | | −N⏉N−CH₂Ph−Cl(p) (piperazine) |
| 483 | Et | | " | " | −N⏉N−CH₂Ph (piperazine) |
| 484 | Et | | " | " | −N⏉N−Ph (piperazine) |
| 485 | Et | | " | " | −N⏉N−CH₂Ph−Cl(p) (piperazine) |

TABLE 1-continued

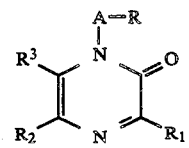

| Compound No. | R₁ | R₂ | R₃ | A | R |
|---|---|---|---|---|---|
| 486 | Et | | " | " | 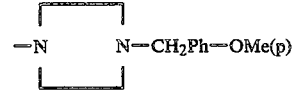 —N  N—CH₂Ph—OMe(p) |
| 487 | (CH₂)₁₃CH₃ | | " | " | —N  N—CH₂Ph |
| 488 | " | | " | " | —N  N—CH₂Ph—NO₂(p) |
| 489 | " | | " | " | —N  N—CH₂Ph—Cl(p) |
| 490 | " | | " | " | —N  N—CH₂Ph—OMe(p) |
| 611 | Me | Me | Me | " | —N  NH |
| 612 | Ph | Me | Me | " | Cl |
| 613 | CH₂Ph | Me | Me | " | Cl |
| 614 | Pro | =(CH₂)₄= | | " | —OH |
| 615 | Pro | " | | " | —S—Ph |
| 616 | Pro | Me | Me | " | —OH |
| 617 | iso-Bu | Me | Me | " | —OH |
| 618 | iso-Bu | =(CH₂)₄= | | —CH₂CH₂— | —OH |
| 619 | " | Me | Me | " | —N  N—CH₂Ph—F(p) |
| 620 | Pro | Et | Et | " | —OH |
| 621 | Bu | =(CH₂)₄= | | " | —OH |
| 622 | iso-Pro | Me | Me | " | —OH |
| 623 | sec-Bu | Me | Me | " | —OH |
| 624 | Bu | Me | Me | " | —OH |
| 625 | iso-Pro | Et | Et | " | —OH |
| 626 | iso-Bu | Et | Et | " | —OH |
| 627 | sec-Bu | Et | Et | " | —OH |
| 628 | Bu | Et | Et | " | —OH |
| 629 | Et | Et | Et | " | —OH |
| 630 | Et | Me | Me | " | —OH |
| 631 | (CH₂)₄CH₃ | —(CH₂)₄— | | " | —OH |
| 632 | (CH₂)₅CH₃ | " | | " | —OH |
| 633 | (CH₂)₆CH₃ | " | | " | —OH |
| 634 | (CH₂)₇CH₃ | " | | " | —OH |
| 635 | (CH₂)₈CH₃ | " | | " | —OH |
| 636 | (CH₂)₉CH₃ | " | | " | —OH |
| 637 | (CH₂)₁₁CH₃ | " | | " | —OH |
| 638 | (CH₂)₁₃CH₃ | " | | " | —OH |
| 639 | (CH₂)₁₅CH₃ | " | | " | —OH |
| 640 | CH₂Ph | Et | Et | " | —OH |
| 641 | CH₂Ph—Cl (p) | Et | Et | " | —OH |

TABLE 1-continued

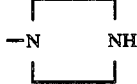

| Compound No. | R₁ | R₂ | R₃ | A | R |
|---|---|---|---|---|---|
| 642 | Me | Me | Me | " | 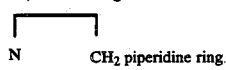 —N NH |
| 643 | CH₂Ph | —(CH₂)₄— | | " | —OH |
| 644 | CH₂Ph | " | | " | Cl |
| 645 | CH₂CH₂Ph | " | | " | —OH |
| 646 | Et | " | | " | —OH |
| 647 | CH₂Ph—Cl (p) | Et | Et | " | Cl |

Me; methyl
Et; ethyl
Pro; propyl
iso-Pro; isopropyl
Bu; butyl
iso-Bu; isobutyl
sec-Bu; sec-butyl
Ph; benzene ring

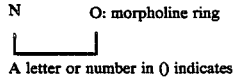 N  CH₂ piperidine ring.

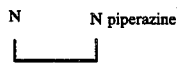 N  O: morpholine ring

A letter or number in () indicates the position of the preceding substituent.

N  N piperazine

 N  N: homopiperazine

The pharmacological activity of the present compounds [1] is illustrated below. All the compounds [1] used in the pharmacological tests were tested in the form of the hydrochloride salt thereof.

1. Platelet aggregation inhibition:

Sample solution containing a compound [1] (final concentration 500 or 100 μM) is added to rabbit platelet plasma to which was added 10% by volume of a 3.8% sodium citrate solution, and the mixture is incubated at 37° C. for 3 mins. A platelet activation factor (PAF, final concentration 10–50 ng/ml) or collagen (final concentration 2.5 μg/ml) is added thereto as an aggregating agent, and platelet aggregation activity is measured with an aggrigometer. The results of assays for PAF-induced aggregation are shown in Table 2, and those for collagen-induced aggregation are shown in Table 3, which tables show the strong platelet aggregation inhibitory activity of the compounds [1] of the present invention.

TABLE 2

Platelet Aggregation Inhibitory Action on PAF-Induced Aggregation

| Compound No. | Concentration μM | Inhibition % | Compound No. | Concentration μM | Inhibition % |
|---|---|---|---|---|---|
| 114 | 500 | 63 | 174 | 500 | 96 |
| 115 | " | 88 | 175 | " | 94 |
| 116 | " | 76 | 176 | " | 81 |
| 120 | " | 83 | 177 | " | 79 |
| 126 | " | 54 | 178 | " | 94 |
| 128 | " | 83 | 179 | " | 93 |
| 129 | " | 79 | 180 | " | 90 |
| 132 | " | 72 | 183 | " | 85 |
| 133 | " | 63 | 185 | " | 61 |
| 134 | " | 57 | 188 | " | 86 |
| 142 | " | 82 | 189 | " | 69 |
| 143 | " | 87 | 191 | " | 62 |
| 145 | " | 52 | 253 | 100 | 93 |
| 146 | " | 87 | 263 | " | 70 |
| 154 | " | 54 | 306 | " | 60 |
| 158 | " | 64 | 308 | " | 40 |
| 160 | " | 97 | 310 | " | 46 |
| 161 | " | 93 | 313 | " | 48 |
| 162 | " | 93 | 316 | " | 49 |
| 163 | " | 62 | 321 | " | 43 |
| 165 | " | 92 | 323 | " | 43 |
| 166 | " | 87 | 326 | " | 51 |
| 168 | " | 76 | 332 | " | 46 |
| 170 | " | 80 | 386 | " | 71 |
| 172 | " | 57 | 387 | " | 41 |
| 173 | " | 61 | | | |

TABLE 3

Platelet Aggregation Inhibitory Action on Collagen-Induced Aggregation

| Compound No. | Concentration μM | Inhibition % | Compound No. | Concentration μM | Inhibition % |
|---|---|---|---|---|---|
| 114 | 100 | 50 | 289 | 100 | 58 |
| 115 | " | 50 | 292 | " | 50 |
| 251 | " | 78 | 384 | " | 76 |
| 252 | " | 42 | 386 | " | 71 |
| 253 | " | 52 | 467 | " | 80 |
| 255 | " | 48 | 471 | " | 81 |
| 263 | " | 73 | 473 | " | 64 |
| 265 | " | 45 | 474 | " | 81 |
| 287 | " | 50 | 475 | " | 81 |
| 288 | " | 72 | 477 | " | 72 |

2. Vasodilation activity:

A dog, pretreated with morphine (81.5 mg/kg, sc) is anesthetized with urethane (8450 mg/kg, iv) and α-chloralose (45 mg/kg, iv), and immobilized in the dosal position. Right femoral arterial blood is introduced into a left femoral artery via a perfusion pump, and Sterling's resistance is connected to the exosomatic circulatory system to perfuse blood to a left back limb at constant pressure. The perfusion pressure is set with a valve at slightly higher than that of the average blood pressure of the animal. Sample (100 μg) dissolved in physiological saline solution is administered to a right femoral artery, and changes in blood flow are measured. Vasodilation activity is measured as a relative activity, by defining as 100% the increased rate of blood flow when 30 μg papaverine is administered intra-arterially. The results are shown in Table 4, where it will be seen that the compounds [1] of the present invention have strong vasodilation activity.

TABLE 4

Vasodilation Activity

| Compound No. | Vasodilation activity % | Compound No. | Vasodilation activity % |
|---|---|---|---|
| 023 | 118 | 158 | 139 |
| 024 | 182 | 160 | 117 |
| 025 | 112 | 161 | 214 |
| 114 | 174 | 162 | 212 |
| 115 | 210 | 165 | 222 |
| 116 | 147 | 166 | 153 |
| 119 | 132 | 168 | 205 |
| 120 | 223 | 170 | 178 |
| 122 | 161 | 171 | 122 |
| 124 | 278 | 174 | 179 |
| 125 | 220 | 175 | 151 |
| 126 | 310 | 176 | 159 |
| 128 | 155 | 177 | 122 |
| 129 | 201 | 178 | 111 |
| 131 | 158 | 179 | 139 |
| 132 | 231 | 180 | 136 |
| 133 | 251 | 181 | 125 |
| 134 | 143 | 183 | 107 |
| 142 | 151 | 185 | 115 |
| 143 | 119 | 188 | 188 |
| 144 | 120 | 189 | 133 |
| 146 | 125 | 191 | 165 |
| 149 | 122 | 193 | 226 |
| 150 | 229 | 254 | 232 |
| 151 | 121 | 287 | 170 |
| 153 | 197 | 288 | 232 |
| 157 | 162 | 297 | 229 |

3. Antioxidant activity:

Antioxidant activity is determined according to the method of Stocks et al. (Clin. Sci. Mol. Med., 47: 215 (1974)). Rat cerebrum is added to ice-cooled 40 mM phosphate saline buffer solution (PBS) (pH 7.4, 4 ml buffer per 1 g cerebrum), homogenized and centrifuged (1000×g, 4° C., 10 min.) to obtain supernatant solution. The supernatant solution is diluted five-fold with the above ice-cooled PBS solution, and to a 0.9 ml aliquot thereof is added a sample containing a compound [1] (0.1 ml, final concentration 100 μM) dissolved in ethanol. The resultant mixture is incubated at 37° C. for 15 mins., 35% perchloric acid (0.2 ml) is added, and the mixture is then ice-cooled to stop the reaction and centrifuged (1300×g, 4° C., 10 min.). 0.5 ml thiobarbituric acid (5 g/lit. of 50% acetic acid) is added to the supernatant solution (1 ml), whereafter it is heated at 100° C. for 30 mins. and ice-cooled, so as to measure its absorbency at 532 nm. The amount of lipoperoxide thus-generated is expressed as an amount of malondialdehyde. The results are shown in Table 5, where it will be seen that the compounds [1] of the present invention inhibit lipoperoxide generation.

TABLE 5

Antioxidant Activity

| Compound No. | Inhibition % | Compound No. | Inhibition % |
|---|---|---|---|
| 115 | 44 | 307 | 50 |
| 119 | 41 | 308 | 57 |
| 129 | 53 | 309 | 71 |
| 132 | 53 | 310 | 79 |
| 133 | 51 | 311 | 89 |
| 134 | 49 | 312 | 93 |
| 142 | 48 | 313 | 89 |
| 143 | 53 | 314 | 75 |
| 150 | 45 | 315 | 82 |
| 154 | 51 | 316 | 86 |
| 158 | 44 | 317 | 68 |
| 160 | 41 | 318 | 82 |
| 161 | 76 | 319 | 89 |
| 162 | 47 | 320 | 86 |
| 165 | 70 | 321 | 75 |
| 168 | 59 | 322 | 79 |
| 175 | 49 | 323 | 75 |
| 176 | 88 | 324 | 64 |
| 177 | 73 | 325 | 92 |
| 178 | 67 | 326 | 88 |
| 180 | 69 | 327 | 92 |
| 183 | 41 | 328 | 72 |
| 185 | 63 | 329 | 88 |
| 256 | 66 | 330 | 92 |
| 258 | 87 | 331 | 88 |
| 260 | 62 | 332 | 80 |
| 264 | 79 | 334 | 56 |
| 267 | 68 | 335 | 80 |
| 268 | 77 | 336 | 96 |
| 269 | 70 | 337 | 88 |
| 270 | 93 | 338 | 80 |
| 272 | 83 | 339 | 72 |
| 273 | 77 | 340 | 92 |
| 274 | 77 | 378 | 52 |
| 275 | 80 | 385 | 67 |
| 276 | 67 | 386 | 50 |
| 277 | 70 | 387 | 77 |
| 278 | 87 | 467 | 61 |
| 279 | 73 | 472 | 53 |
| 280 | 67 | 473 | 58 |
| 281 | 77 | 478 | 59 |
| 282 | 87 | 479 | 53 |
| 283 | 53 | 487 | 72 |
| 295 | 55 | 488 | 84 |
| 305 | 61 | 489 | 78 |
| 306 | 54 | 490 | 75 |

As explained hereinabove, a compound [1] of the present invention or its corresponding salt inhibits platelet aggregation, has vasodilating activity, and/or inhibits lipoperoxide generation, and is useful in pharmaceutical form for treating circulatory and metabolic disorders.

EXAMPLES

The following examples are illustrative of the present invention, but are not to be construed as limiting.

In the examples, the Rf value of silica-gel thin layer chromatography (TLC) is either specified by or measured using the following carrier and developing solvent:

Carrier: silica-gel, Kieselgel 60 F$_{254}$ (Merck)
Developer: chloroform-methanol (20:1)

Physical properties of the compounds [1] obtained in the following examples are shown in Table 27.

EXAMPLE 1

1-(2-hydroxyethyl)-3,5,6-trimethyl-2-oxo-1,2-dihydropyrazine (compound 026)

2-Hydroxy-3,5,6-trimethylpyrazine (13.8 g, 0.1M) and 5N NaOH (100 ml, 0.5M) were added to t-butanol (200 ml). Ethylene chlorohydrin (40.3 g, 0.5M) was added thereto and the mixture was stirred at 60° C. for 2 hours. Water was added to the reaction mixture, which was then extracted 10 times with chloroform (100 ml), and the extract dried with anhydrous magnesium sulfate and concetrated in vacuo. The residue was charged on a column of silica-gel (Wako Pure Chem. Co., C-200) and eluted with chloroform-methanol (300:1) to obtain the product (14.4 g, yield: 79.1%). Dihydrochloride: m.p.: 140°–144° C.

EXAMPLES 2-9

1-(2-substituted ethyl)-3,5,6-trimethyl-2-oxo-1,2-dihydropyrazine

Thionylchloride (0.86 ml, 12 mM) in chloroform (0.5 ml) was added dropwise under ice-cooling to the compound 026 (1.82 g, 10 mM) suspended in chloroform (5 ml) and stirred at room temperature for 3 hours to chlorinate. The reaction mixture was poured into dilute aqueous Na$_2$CO$_3$, extracted three times with chloroform, and the extract dried with anhydrous sodium sulfate and concentrated in vacuo.

The obtained chlorinated compound was dissolved in benzene (60 ml), base (20 mM) and triethylamine (2.8 ml, 20 mM) were added thereto, and the mixture was refluxed. The reaction mixture was washed with dilute aqueous Na$_2$CO$_3$ and the aqueous layer was extracted two times with benzene. The combined benzene layer, which was dried with anhydrous sodium sulfate, was concentrated in vacuo. The residue was chromatographed on a silica-gel (80 g) column using an elution solvent of chloroform-methanol to obtain the compounds in Table 6.

Table 6 shows the identify of the base, the reflux time and the ratio of chloroform-methanol mixture used in each of the above examples.

EXAMPLES 10-11

1-(2-substituted thioethyl)-3,5,6-trimethyl-2-oxo-1,2-dihydropyrazine

Compound 026 (0.91 g, 5 mM) was chlorinated with thionylchloride according to the same method used in Examples 2-9. The thus-obtained chlorinated compound was dissolved in dimethylformamide (DMF, 10 ml), sodium mercaptan (5 mM) was added, and the mixture was stirred at room temperature for 2 days. DMF was driven off in vacuo. Dilute aqueous K$_2$CO$_3$ solution was added to the residue, whereafter it was extracted with chloroform, dried by adding anhydrous sodium sulfate and concentrated in vacuo. The residue was chromatographed on a silica-gel (C-200, 50 g) column eluted with benzene-ethyl acetate (5:1) to obtain the product in Table 7.

Table 7 shows the particular mercaptans used in the above examples.

EXAMPLE 12

1,4-bis[2-(3,5,6-trimethyl-2-oxo-1,2-dihydropyrazine-1-yl)ethyl]piperazine (compound 101)

Chloroform (3 ml) in solution with thionylchloride (4.3 ml, 60 mM) was added dropwise under ice-cooling to compound 026 (9.10 g, 50 mM) suspended in chloroform (15 ml). After stirring at room temperature for 3 hours, the reaction mixture was poured into dilute aqueous K$_2$CO$_3$ and extracted with chloroform (200 ml). The chloroform layer was dried with anhydrous magnesium sulfate and concentrated in vacuo. The residue was dissolved in benzene (300 ml), piperazine (2.15 g) and triethylamine (0.8 ml, 50 mM) were added, and the mixture was refluxed for 3 hours. THe reaction mixture was washed with dilute aqueous K$_2$CO$_3$ and the aqueous layer was extracted with chloroform. The chloroform layer was dried with anhydrous magnesium sulfate and concentrated in vacuo. The residue was charged on a column of silica-gel (C-200, 180 g), and eluted with chloroform-methanol (100:1) to obtain compound 101 (7.60 g, yield: 73.2%).

EXAMPLE 13

1-(2-piperazinoethyl)-3,5,6-trimethyl-1,2-dihydropyrazine (compound 642)

Piperazine (17.2 g, 0.2M) and triethylamine (28 ml, 0.2M) were used in the method of Example 12, the other conditions being preserved, to obtain compound 642 (5.52 g, yield: 44.2%) which displayed a lower Rf value relative to compound 101.

EXAMPLE 14

1-(2-hydroxyethyl)-3-phenyl-5,6-dimethyl-2-oxo-1,2-dihydropyrazine (compound 109)

Ethylene chlorohydrin (20.2 g, 0.25M) was added to a solution of 2-hydroxy-3-phenyl-5,6-dimethyl-pyrazine (10.0 g, 50 mM) and 5N NaOH (50 ml) in t-butanol (150 ml), and stirred at 60° C. for 2.5 hours. Water was added to the reaction mixture, the mixture extracted with chloroform, and the extract dried with anhydrous sodium sulfate and concentrated in vacuo. The residue was charged on a column of silica-gel (C-200, 130 g) packed with chloroform and eluted with chloroform-methanol (100:1) to obtain compound 109 (8.73 g, yield: 71.5%).

EXAMPLE 15

1-(2-chloroethyl)-3-phenyl-5,6-dimethyl-2-oxo-1,2-dihydropyrazine (compound 612)

Thionylchloride (0.42 ml, 6.0 mM) was added dropwise under ice-cooling to compound 109 (1.22 g, 50 mM) dissolved in chloroform (10 ml), and stirred at room temperature for 3 hours. Chloroform was added to the reaction mixture, whereafter the mixture was washed with dilute aqueous K$_2$CO$_3$ and the resultant aqueous layer extracted with further chloroform. The chloroform layer was combined, dried with anhydrous magnesium sulfate and concentrated in vacuo. The residue was charged on a column of silica-gel (C-200, 25 g), and eluted with chloroform to obtain compound 612 (0.59 g, yield: 42.7%).

EXAMPLES 16-17

1-(2-substituted ethyl)-3-phenyl-5,6-dimethyl-2-oxo-1,2-dihydropyrazine

Base (5 mM) and triethylamine (0.70 ml, 5 mM) were added to compound 612 (0.66 g, 2.5 mM) dissolved in benzene (15 ml), and refluxed. The reaction mixture was washed with dilute aqueous $K_2CO_3$, and the resultant aqueous layer extracted with benzene. The benzene layer was combined, dried with anhydrous sodium sulfate and concentrated in vacuo. The residue was charged on a column of silica-gel (C-200, 65 g) and eluted with chloroform-methanol to obtain the compounds in Table 8.

Table 8 identifies the base, reflux time and the ratio of the chloroform-methanol mixture used in the above examples.

EXAMPLE 18

1-(2-hydroxyethyl)-3-benzyl-5,6-dimethyl-2-oxo-1,2-dihydropyrazine (compound 112)

Ethylene chlorohydrin 4.03 g, 50 mM was added to a solution of 2-hydroxy-3-benzyl-5,6-dimethyl-pyrazine (2.14 g, 10 mM) and 5N NaOH (10 ml) in t-butanol (30 ml), and stirred at 60° C. for 2.5 hours. Water (100 ml) was added to the reaction mixture, and the mixture was extracted three times with chloroform, the extract dried with anhydrous magnesium sulfate and concentrated in vacuo. The residue was charged on a column of silica-gel (C-200, 25 g) and eluted with chloroform-methanol (100:1) to obtain compound 112 (2.22 g, yield: 86.0%).

EXAMPLE 19

1-(2-chloroethyl)-3-benzyl-5,6-dimethyl-2-oxo-1,2-dihydropyrazine (compound 613)

Thionylchloride (0.42 ml, 6.0 mM) was added dropwise under ice-cooling to a compound 112 (1.29 g, 5 mM) dissolved in chloroform (6 ml), and stirred at room temperature for 5 hours. Chloroform (70 ml) was added to the reaction mixture, which mixture was then washed with dilute aqueous $K_2CO_3$, the resulting aqueous layer being twice extracted with further chloroform. The chloroform layer was combined, dried with anhydrous magnesium sulfate and concentrated in vacuo. The residue was charged on a column of silica-gel (C-200, 25 g), packed with chloroform, and eluted with chloroform to obtain compound 613 (1.00 g, yield: 87.5%).

EXAMPLES 20-23

1-(2-substituted ethyl)-3-benzyl-5,6-dimethyl-2-oxo 1,2-dihydropyrazine

Base (6.0 mM) and triethylamine (0.84 ml, 6.0 mM) were added to compound 613 (0.83 g, 30 mM) dissolved in benzene (15 ml), and refluxed. The reaction mixture was washed with dilute aqueous $K_2CO_3$, and the aqueous layer extracted with further benzene. The benzene layer was combined, dried with anhydrous sodium sulfate and concentrated in vacuo. The residue was charged on a column of silica-gel (C-200, 65 g) packed with chloroform and eluted with chloroform-methanol to obtain the compounds of Table 9.

Table 9 identifies the base, reflux time and ratio of chloroform-methanol mixture used in the above examples.

EXAMPLES 24-28

1-(2-hydroxyethyl)-3-alkyl-5,6-dimethyl-2-oxo-1,2-dihydropyrazine

Aqueous 5N NaOH (10 ml, 50 mM), t-butanol (30 ml) and ethylene chlorohydrin (50 mM) were added to 2-hydroxy-3-alkyl-5,6-dimethyl-pyrazine (10 mM) and stirred at 60° C. Water was added to the reaction mixture, which mixture was then extracted three times with chloroform, dried with anhydrous magnesium sulfate and concentrated in vacuo. The residue was charged on a column of silica-gel (C-200, 120 g) and eluted with chloroform-methanol to obtain the compounds (hydroxy ethyl form) of Table 10.

Table 10 identifies the specific 2-hydroxy-3-alkyl-5,6-dimethyl-pyrazine, its amount used, reaction time in hours, and ratio of mixture of chloroform-methanol used in each of the above examples.

EXAMPLES 29-46

1-(2-substituted ethyl)-3-alkyl-5,6-trimethyl-2-oxo 1,2-dihydropyrazine

Thionylchloride (0.34 ml) was added dropwise under ice-cooling to the hydroxy ethyl form (4 mM) of the compounds obtained in Examples 24-28, and the reaction mixture was dissolved in chloroform (5 ml) and stirred at room temperature for one hour. Chloroform was added to the reaction mixture, which mixture was washed with dilute aqueous $K_2CO_3$, and the resultant aqueous layer extracted twice with further chloroform. The chloroform layer was combined, dried with anhydrous magnesium sulfate and concentrated in vacuo. Benzene (30 ml), triethylamine (1.12 ml) and base (8 mM) were added to the residue and the resultant mixture was refluxed. Chloroform (100-120 ml) was added to the reaction mixture and washed with dilute aqueous $K_2CO_3$. The aqueous layer was extracted twice with chloroform. The chloroform layer was combined, dried with anhydrous magnesium sulfate and concentrated in vacuo. The residue was charged on a column of silica-gel (C-200, 60 g) and eluted with chloroform-methanol to obtain the compounds shown in Table 11.

Table 11 identifies the starting material (hydroxy ethyl form), base, reflux time and ratio of chloroform-methanol mixture used in the above examples.

EXAMPLES 47-49

1-(2-hydroxyethyl)-3-alkyl-5,6-dimethyl-2-oxo-1,2,5,6,7,8-hexahydroquinoxaline Aqueous 5N NaOH (10 ml, 50 mM), t-butanol (30 ml) and ethylene chlorohydrin (50 mM) were added to 2-hydroxy-3-alkyl-5,6,7,8-tetrahydroquinoxaline (10 mM) and stirred at 60° C. Water was added to the reaction mixture, which mixture was then extracted with chloroform, dried with anhydrous magnesium sulfate and concentrated in vacuo. The residue was charged on a column of silica-gel (C-200) and eluted with chloroform-methanol to obtain the compounds (hydroxy ethyl form) of Table 12.

Table 12 identifies the specific 2-hydroxy-3-alkyl-5,6,7,8-tetrahydroquinoxaline (group $R_1$), its amount used, reaction time in hours, and ratio of the chloroform-methanol mixture used in the above examples.

EXAMPLES 50-62

1-(2-substituted ethyl)-3-alkyl-2-oxo-1,2,5,6,7,8-hexahydroquinoxaline

Thionylchloride (0.34 ml) was added dropwise under ice-cooling to the hydroxy ethyl form (4 mM) of the compounds obtained in Examples 47-49, dissolved in chloroform and stirred at room temperature for one hour. Chloroform was added to the reaction mixture, which mixture was then washed with dilute aqueous $K_2CO_3$, and the resultant aqueous layer extracted with chloroform. The chloroform layer was combined, dried with anhydrous magnesium sulfate and concentrated in vacuo. Benzene (30 ml), triethylamine (1.12 ml, 8 mM) and base (8 mM) were added to the reaction mixture, followed by refluxing. Chloroform (100 ml) was added to the reaction mixture, which mixture was then washed with dilute aqueous $K_2CO_3$, and the resultant aqueous layer extracted with chloroform. The chloroform layer was combined, dried with anhydrous magnesium sulfate and concentrated in vacuo. The residue was charged on a column of silica-gel (C-200, 70 g) and eluted with chloroform-methanol to obtain the compounds shown in Table 13.

Table 13 identifies the starting material (hydroxy ethyl form), base, reflux time and ratio of chloroform-methanol mixture used in the above examples.

EXAMPLES 63-68

1-(2-hydroxyethyl)-3-alkyl-5,6-diethyl-3-oxo-1,2-dihydropyrazine

Aqueous 5N NaOH (10 ml, 50 mM), t-butanol (30 ml) and ethylene chlorohydrin (50 mM) were added to 2-hydroxy-3-alkyl-5,6-diethyl-pyrazine (10 mM) and stirred at 60° C. Water was added to the reaction mixture, which mixture was then extracted with chloroform, dried with anhydrous sodium sulfate and concentrated in vacuo.

The residue was charged on a silica-gel column (C-200) packed with chloroform, and eluted with chloroform-methanol to obtain the compounds in Table 14.

Table 14 identifies the specific 2-hydroxy-3-alkyl-5,6-diethyl-pyrazine (group $R_1$), its amount used, reaction time in hours, amount of silica-gel and ratio of chloroform-methanol mixture used in each of the above examples.

EXAMPLES 69-101

1-(2-substituted ethyl)-3-alkyl-5,6-diethyl-2-oxo-1,2-dihydropyrazine

Thionylchloride (0.34 ml) was added dropwise under ice-cooling to the hydroxy ethyl form (4 mM) of the compounds obtained in Examples 63-68, dissolved in chloroform (5 ml) and stirred at room temperature for one hour. Chloroform was added to the reaction mixture, which mixture was then washed with dilute aqueous $K_2CO_3$, and the resultant aqueous layer extracted twice with further chloroform. The chloroform layer was combined, dried with anhydrous magnesium sulfate and concentrated in vacuo. Benzene (30 ml), triethylamine (1.12 ml, 8 mM) and base (8 mM) were added to the residue, followed by refluxing. Chloroform (100 ml) was added to the reaction mixture, and the mixture was washed with dilute aqueous $K_2CO_3$. The resultant aqueous layer was extracted with additional chloroform. The chloroform layer was combined, dried with anhydrous magnesium sulfate and concentrated in vacuo. The residue was charged on a column of silica-gel (C-200, 60 g) packed with chloroform, and eluted with chloroform-methanol to obtain the compounds shown in Table 15.

Table 15 identifies the starting material (hydroxy ethyl form), base, reflux time and ratio of chloroform-methanol mixture used in the above examples.

EXAMPLE 102

1-(2-hydroxyethyl)-3-ethyl-5,6-dimethyl-2-oxo-1,2-dihydropyrazine (compound 630)

Ethylene chlorohydrin (32.21 g, 0.4M) was added to a solution of 2-hydroxy-3-ethyl-5,6-dimethyl-pyrazine (12.16 g, 80 mM) and 5N NaOH (80 ml) in t-butanol (240 ml), and stirred at 60° C. for 3 hours. Dilute aqueous $K_2CO_3$ was added to the reaction mixture, the mixture extracted with chloroform, and the resultant aqueous layer extracted twice with further chloroform. The combined chloroform layers were dried with anhydrous magnesium sulfate and concentrated in vacuo. The residue was charged on a column of silica-gel (C-200, 250 g) packed with chloroform and eluted with chloroform-methanol (from 200:1 to 50:1) to obtain compound 630 (12.31 g, yield: 78.5%).

EXAMPLES 103-110

1-(2-substituted ethyl)-3-ethyl-5,6-dimethyl-2-oxo-1,2-dihydropyrazine

Thionylchloride (0.43 ml) was added dropwise under ice-cooling to compound (0.98 g, 5 mM) dissolved in chloroform (5 ml), and stirred at room temperature for one hour. Chloroform (50 ml) was added to the reaction mixture, the mixture then washed with dilute aqueous $K_2CO_3$, and the resultant aqueous layer extracted twice with additional chloroform (50 ml). The chloroform layer was combined, dried with anhydrous magnesium sulfate and concentrated in vacuo. Benzene (30 ml), triethylamine (1.40 ml) and base (10 mM) were added to the residue and refluxed. Chloroform (100 ml) was added to the reaction mixture, which mixture was then washed with dilute aqueous $K_2CO_3$. The resultant aqueous layer was extracted twice with chloroform (50 ml). The chloroform layer was combined, dried with anhydrous magnesium sulfate and concentrated in vacuo. The residue was charged on a column of silica-gel (C-200, 70 g) packed with chloroform, and eluted with chloroform-methanol to obtain the compounds shown in Table 16.

Table 16 identifies the base, reflux time and ratio of chloroform-methanol mixture used in the above examples.

EXAMPLE 111

1-(2-hydroxyethyl)-3-benzyl-5,6-diethyl-2-oxo-1,2-dihydropyrazine (compound 640)

Ethylene chlorohydrin (20.15 g, 0.25M) was added to a solution of 2-hydroxy-3-benzyl-5,6-diethyl-pyrazine (12.10 g, 50 mM) and 5N NaOH (50 ml) in t-butanol (150 ml), and stirred at 60° C. for 3 hours. The t-butanol was distilled off in vacuo, water was added thereto and the mixture was extracted three times with chloroform. The extract was dried with anhydrous magnesium sulfate and concentrated in vacuo. The residue was charged on a column of silica-gel (C-200, 230 g) packed with chloroform and eluted with chloroform-methanol (100:1) to obtain compound 640 (12.31 g, yield: 58.7%).

EXAMPLES 112–122

1-(2-substituted ethyl)-3-benzyl-5,6-dimethyl-2-oxo-1,2-dihydropyrazine

Thionylchloride (0.34 ml) was added dropwise under ice-cooling to compound 640 (1.15 g, 4.0 mM) dissolved in chloroform (5 ml) and stirred at room temperature for one hour. Chloroform (100 ml) was added to the reaction mixture, which mixture was then washed with dilute aqueous $K_2CO_3$, and the resultant aqueous layer extracted twice with additional chloroform (30 ml). The chloroform layer was combined, dried with anhydrous sodium sulfate and concentrated in vacuo. Triethylamine (1.12 ml, 8 mM) and base (8 mM) were added to the residue dissolved in benzene (30 ml), followed by refluxing. The reaction mixture was washed with dilute aqueous $K_2CO_3$. The resultant aqueous layer was extracted twice with benzene. The benzene layer was combined, dried with anhydrous sodium sulfate and concentrated in vacuo. The residue was charged on a column of silica-gel (C-200, 60 g) and eluted with chloroform-methanol to obtain the compounds shown in Table 17.

Table 17 identifies the base, reflux time and ratio of chloroform-methanol mixture used in the above examples.

EXAMPLE 123

1-(2-hydroxyethyl)-3-p-chlorobenzyl-5,6-dimethyl-2-oxo-1,2-dihydropyrazine (compound 641)

Ethylene chlorohydrin (16.11 g, 0.20M) was added to a solution of 2-hydroxy-3-p-chlorobenzyl-5,6-dimethylpyrazine (11.06 g, 40 mM) in aqueous 5N NaOH (40 ml) and t-butanol (120 ml), and stirred at 60° C. for 3 hours. The t-butanol was distilled off in vacuo. Dilute aqueous $K_2CO_3$ was added to the residue, the resulting mixture being extracted three times with chloroform, dried wit anhydrous sodium sulfate and concentrated in vacuo. The residue was charged on a column of silica-gel (C-200, 300 g) packed with chloroform and eluted with chloroform-methanol (100:1) to obtain compound 641 (9.73 g, yield: 75.9%).

EXAMPLE 124

1-(2-chloroethyl)-3-p-chlorobenzyl-5,6-diethyl-2-oxo-1,2-dihydropyrazine (compound 647)

Thionylchloride (1.20 ml) was added dropwise to compound 641 (4.16 g, 13 mM) dissolved in chloroform (20 ml) under ice-cooling and stirred at room temperature for 1.5 hours. Dilute aqueous $K_2CO_3$ was added to the reaction mixture, the resulting mixture being extracted with chloroform, dried with anhydrous sodium sulfate and concentrated in vacuo to obtain compound 647 (4.27 g, yield: 96.9%).

EXAMPLES 125–129

1-(2-substituted ethyl) 3-p-chlorobenzyl-5,6-diethyl-2-oxo-1,2-dihydropyrazine

Base (6 mM) and triethylamine were added to chloroethyl compound 649 (1.023 g, 3 mM) dissolved in benzene (30 ml), and refluxed. The reaction mixture was poured into dilute aqueous $K_2CO_3$, the resultant aqueous layer being washed and extracted with benzene. The benzene layer was combined, dried with anhydrous sodium sulfate and concentrated in vacuo. The residue was charged on a column of silica-gel (C-200, 65 g) packed with chloroform and eluted with chloroform-methanol to obtain the compounds of Table 18.

Table 18 identifies the base, reflux time and ratio of chloroform-methanol mixture used in the above examples.

EXAMPLES 130–138

1-(2-hydroxyethyl)-3-alkyl-2-oxo-1,2,5,6,7,8-hexahydroquinoxaline

Ethylene chlorohydrin (4.03 g, 50 mM) was added to a solution of 2-hydroxy-3-alkyl-5,6,7,8-tetrahydroquinoxaline (10 mM) in aqueous 5N NaOH (10 ml, 50 mM) and t-butanol (30 ml), and stirred at 60° C. for 4 hours. Water was added to the reaction mixture, which mixture was then extracted with chloroform, dried with anhydrous sodium sulfate and concentrated in vacuo. The residue was charged on a column of silica-gel (C-200) packed with chloroform and eluted to obtain the compounds (hydroxy ethyl form) of Table 19.

The kind of 2-hydroxy-3-alkyl-5,6,7,8-tetrahydroquinoxaline (group $R_1$), its amount used, amount of silica gel used in column chromatography and kind of elution solvent are illustrated in Table 19.

EXAMPLES 139–214

1-(2-substituted ethyl)-3-alkyl-2-oxo-1,2,3,5,6,7,8-hexahydroquinoxaline

Thionylchloride (1.3 equivalent) was added dropwise under ice-cooling to the hydroxy ethyl form (3–5 mM) of the compounds obtained in Examples 130–138, dissolved in chloroform (3–5 ml) and stirred at room temperature for one hour. Dilute aqueous $K_2CO_3$ was added to the reaction mixture, which mixture was then extracted three times with chloroform (50 ml), dried with anhydrous sodium sulfate, and concentrated in vacuo. Benzene (30 ml), triethylamine (2 eq.) and base (2 eq.) were added to the residue, followed by refluxing. The reaction mixture was poured into dilute aqueous $K_2CO_3$, then extracted several times with benzene. The extract was dried with anhydrous sodium sulfate and concentrated in vacuo. The residue was charged on a column of silica-gel (C-200, 60 g) and eluted with chloroform-methanol (200:1) to obtain the compounds shown in Table 20.

The kind of starting material (hydroxy ethyl form), amount thereof used, base and reflux time are shown in Table 20.

EXAMPLE 215

1-(2-piperazinyl ethyl)-3-ethyl-5,6-dimethyl-3-oxo-1,2-dihydropyrazine

Thionylchloride (6.6 ml) was added dropwise under ice-cooling to compound 630 (13.72 g, 70 mM) dissolved in chloroform (70 ml), and stirred at room temperature for one hour. Dilute aqueous $K_2CO_3$ was added to the reaction mixture, which was then extracted with chloroform. The extract was dried with anhydrous magnesium sulfate and concentrated in vacuo. Triethylamine (19.6 ml, 0.14M) and anhydrous piperazine (64.4 g, 0.75M) were added to the residue dissolved in benzene (420 ml), and refluxed for 3 hours. The reaction mixture was washed with dilute aqueous $K_2CO_3$. The resultant aqueous layer was extracted with benzene. The benzene layer was combined, dried with anhydrous magnesium sulfate and concentrated in vacuo. The residue was charged on a column of silica-gel (C-200, 375 g) packed with chloroform and eluted with chloroform-methanol (10:1) to obtain compound 454 (13.66 g, yield: 73.9%).

EXAMPLES 216-226

1-[2-(4'-arylpiperazinyl)ethyl]-3-ethyl-5,6-dimethyl-2-oxo-1,2-dihydropyrazine (a) Acid chloride method:

Triethylamine (0.84 ml, 6 mM) was added to compound 454 (0.81 g, 3 mM) dissolved in chloroform (10 ml), and acid chloride (3 mM) was added thereto under ice-cooling. Dilute aqueous $K_2CO_3$ was added to the reaction mixture, which mixture was then extracted three times with chloroform. The combined chloroform layer was dried with anhydrous sodium sulfate and concentrated in vacuo. The residue was charged on a column of silica-gel (C-200, 80 g) packed with chloroform and eluted with chloroform-methanol to obtain the compounds shown in Table 21.

(b) Mixed anhydride method:

Triethylamine (0.70 ml) was added to the carboxylic acid (5 mM) dissolved in tetrahydrofuran (10 ml). After pivaloyl chloride (0.61 g, 5 mM) was added dropwise thereto at −5° C. and stirred for 30 mins., a solution of compound 454 (1.06 g, 4 mM) in chloroform was added dropwise. Reaction was continued under gradually increasing temperature, up to room temperature. The reaction mixture was thereafter treated as in method (a) above, to obtain the products shown in Table 21.

Acylation method, acylating agent used, reaction time and ratio of chloroform-methanol mixture are shown in Table 21.

EXAMPLE 227

1-(2-hydroxyethyl-3-benzyl-2-oxo-1,2,5,6,7,8-hexahydroquinoxaline (compound 643)

Ethylene chlorohydrin (16.10 g, 0.2M) was added to a solution of 2-hydroxy-3-benzyl-5,6,7,8-tetrahydroquinoxaline (9.60 g, 40 mM) in dilute aqueous 5N NaOH (40 ml) and t-butanol (120 ml), and stirred at 60° C. for 3 hours. The t-butanol was distilled off in vacuo. The residue was extracted three times with chloroform, dried with anhydrous sodium sulfate and concentrated in vacuo. The residue was charged on a column of silica-gel (C-200, 220 g) packed with chloroform, and eluted with chloroform-methanol (200:1) to obtain compound 643 (10.90 g, yield: 83.8%).

EXAMPLE 228

1-(2-chloroethyl)-3-benzyl-2-oxo-1,2,5,6,7,8-hexahydroquinoxaline (compound 644)

Thionylchloride (2.96 ml, 1.3 eq.) was added dropwise under ice-cooling to compound 643 (9.09 g, 32 mM) dissolved in chloroform (30 ml), and stirred at room temperature for 2 hours. Dilute aqueous $K_2CO_3$ was added to the reaction mixture, which mixture was then extracted twice with chloroform, dried with anhydrous sodium sulfate and concentrated in vacuo. The residue was charged on a column of silica-gel (C-200, 100 g) packed with chloroform and eluted with chloroform to obtain compound 644 (7.55 g, yield: 78.0%).

EXAMPLES 229-234

1-(2-substituted ethyl)-3-benzyl-2-oxo-1,2,5,6,7,8-hexahydroquinoxaline

Base (7 mM) and triethylamine (0.98 ml) were added to compound 644 (1.05 g, 3.5 mM) dissolved in benzene (30 ml), and refluxed. The reaction mixture was washed with dilute aqueous $K_2CO_3$, and the resultant aqueous layer was extracted with benzene. The combined benzene layer was dried with anhydrous sodium sulfate and concentrated in vacuo. The residue was charged on a column of silica-gel (C-200, 65 g) packed with chloroform and eluted with chloroform-methanol to obtain the compounds shown in Table 22.

The kind of base, reflux time and ratio of chloroform-methanol mixture are shown in Table 22.

EXAMPLE 235

1-(2-hydroxyethyl)-3-(2-phenylethyl)-2-oxo-1,2,5,6,7,8-hexahydroquinoxaline (compound 645)

Ethylene chlorodrohydrin (9.0 g) was added to a solution of 2-hydroxy-3-(2-phenylethyl)-5,6,7,8-tetrahydroquinoxaline (5.59 g, 22 mM) in aqueous 5N NaOH and t-butanol (60 ml), and stirred at 60° C. for 3 hours. The t-butanol was distilled off in vacuo, water was added to the residue, and the mixture was extracted three times with chloroform. The extract was dried with anhydrous sodium sulfate and concentrated in vacuo. The residue was charged on a column of silica-gel (C-200, 170 g) packed with chloroform, and eluted with chloroform-methanol (200:1) to obtain compound 645 (6.73 g, yield: 90.9%).

EXAMPLE 236

1-(2-chloroethyl)-3-(2-phenylethyl)-2-oxo-1,2,5,6,7,8-hexahydroquinoxaline (compound 647)

Thionylchloride (2.05 ml) was added dropwise under ice-cooling to compound 645 (6.49 g, 22.1 mM) dissolved in chloroform (25 ml), and stirred at room temperature for 2 hours. Dilute aqueous $K_2CO_3$ was added to the reaction mixture, which mixture was then extracted twice with chloroform. The extract was dried with anhydrous sodium sulfate and concentrated in vacuo to obtain compound 647, which was used without further purification in the following reactions.

EXAMPLES 237-241

1-(2-substituted ethyl)-3-(2-phenylethyl)-2-oxo-1,2,5,6,7,8-hexahydroquinoxaline Base (7 mM) and triethylamine (0.98 ml) were added to compound 647 (1.11 g, 3.5 mM) dissolved in benzene (30 ml), and refluxed. The reaction mixture was washed with dilute aqueous $K_2CO_3$, and the resultant aqueous layer was extracted with benzene. The combined benzene layer was dried with anhydrous sodium sulfate and concentrated in vacuo. The residue was charged on a column of silica-gel (C-200), 65 g) packed with chloroform and eluted with chloroform-methanol to obtain the compounds shown in Table 23.

The kind of base, reflux time and ratio of chloroform-methanol mixture are shown in Table 23.

EXAMPLE 242

1-(2-hydroxyethyl)-3-ethyl-2-oxo-1,2,5,6,7,8-hexahydroquinoxaline (compound 646)

Ethylene chlorohydrin (20.2 g, 0.25M) was added to a solution of 2-hydroxy-3-ethyl-5,6,7,8-tetrahydroquinoxaline (8.90 g, 50 mM) in dilute aqueous 5N NaOH (50 ml) and t-butanol (150 ml), and stirred at 60° C. for 3 hours. The t-butanol was distilled off in vacuo. Water was added to the residue, which residue was then extracted three times with chloroform, dried with anhydrous sodium sulfate and concentrated in vacuo. The residue was charged on a column of silica-gel (C-200, 170 g) packed with chloroform, and eluted with chloroform-methanol (100:1) to obtain compound 646 (9.30 g, yield: 83.8%).

EXAMPLES 243–248

1-(2-substituted ethyl)-3-ethyl-2-oxo-1,2,5,6,7,8-hexahydroquinoxaline

Thionylchloride (0.47 ml) was added dropwise under ice-cooling to compound 646 (1.11 g, 5 mM) dissolved in chloroform (4 ml), and stirred at room temperature for one hour. Dilute aqueous $K_2CO_3$ was added to the reaction mixture, which mixture was then extracted with chloroform. The extract was dried with anhydrous sodium sulfate and concentrated in vacuo.

Benzene (30 ml), triethylamine (1.4 ml) and base (10 mM) were added to the residue, followed by refluxing. The reaction mixture was poured into dilute aqueous $K_2CO_3$ and extracted with benzene. The extract was dried with anhydrous sodium sulfate and concentrated in vacuo. The residue was charged on a column of silica-gel (C-200, 65 g) packed with chloroform and eluted with chloroform-methanol to obtain the compounds shown in Table 24.

The kind of base, reflux time and ratio of chloroform-methanol mixture are shown in Table 24.

EXAMPLE 249

1-(2-acetoxyethyl)-3,5,6-trimethyl-2-oxo-1,2-dihydropyrazine (compound 061)

Acetic anhydride (2 ml) was added under ice-cooling to compound 026 (0.91 g, 5 mM) dissolved in pyridine (10 ml), and stirred at room temperature for 1.5 hours. The reaction mixture was concentrated in vacuo and dilute aqueous $K_2CO_3$ was added thereto, the resultant mixture being extracted three times with chloroform. The extract was dried with anhydrous magnesium sulfate and concentrated in vacuo. The residue was charged on a column of silica-gel (Florisil, 60 g) packed with benzene and eluted with benzene-ethyl acetate (5:1) to obtain compound 061 (0.58 g, yield: 51.8%).

EXAMPLE 250

1-(2-phenylthioethyl)-3-propyl-2-oxo-1,2,5,6,7,8-hexahydroquinoxaline (compound 615)

Thionylchloride (0.47 ml) was added dropwise under ice-cooling to compound 614 (1.18 g, 5 mM, hydroxy ethyl form) as obtained in Example 47 dissolved in chloroform (5 ml), and stirred at room temperature for hour. Chloroform was added to the reaction mixture, which mixture was then washed with dilute aqueous $K_2CO_3$ and extracted with chloroform. The combined chloroform layer was dried with anhydrous magnesium sulfate and concentrated in vacuo.

Sodium thiophenolate (0.66 g) was added to the residue dissolved in DMF (20 ml), and stirred at room temperature for 2 days. DMF was distilled off in vacuo, dilute aqueous $K_2CO_3$ was added to the residue, and the resulting mixture was extracted with chloroform. The extract was dried with anhydrous sodium sulfate and concentrated in vacuo.

The residue was charged on a column of silica-gel (C-200, 50 g) and eluted with benzene-ethyl acetate (5:1) to obtain compound 615 (1.32 g, yield: 80.7%).

COMPARATIVE EXAMPLE 1

2-hydroxy-3-ethyl-5,6,7,8-tetrahydroquinoxaline 1,2-cyclohexanedione (6.72 g, 60 mM) was added all at once to a methanol solution (100 ml) of α-aminobutylamide 5.1 g, 50 mM) at −30° C., and aqueous 12.5N NaOH (5 ml) was added dropwise thereto. The reaction mixture was stirred at −30° C. for 30 mins., whereafter the cooling was removed and the mixture was stirred at room temperature for 3 hours. Concentrated hydrochloric acid (6.25 ml) was added to the reaction mixture under ice-cooling, and sodium bicarbonate (5 g) was added after 10 mins., the methanol being distilled off in vacuo. The residue was extracted with chloroform, and the extract was washed with water, dried with anhydrous sodium sulfate and concentrated in vacuo. The residue was washed with acetone and recrystallized from acetone to obtain the product as colorless crystals (5.3 g, yield: 60%, m.p.: 152°–153° C.).

NMR (CDCl$_3$) δ(ppm): 1.25 (t, 3H, —CH$_2$CH$_3$), 1.7–1.9 (m, 4H, 6-H$_2$, 7-H$_2$), 2.5–2.8 (m, 4H, 5-H$_2$, 8-H$_2$), 2.80 (q, 2H, —CH$_2$CH$_3$), 13.06 (br. s, 1H, OH).

Mass (CI): 179 (M$^+$+1).

COMPARATIVE EXAMPLE 2

2-hydroxy-3-propyl-5,6,7,8-tetrahydroquinoxaline 1,2-cyclohexanedione (5.4 g, 48 mM) was added all at once to a methanol solution (80 ml) of norvalineamide hydrochloride (6.1 g, 40 mM) at −30° C., and aqueous 12.5N NaOH (8 ml) was added dropwise thereto. The reaction mixture was stirred at −30° C. for 30 mins., cooling was removed, and the mixture stirred at room temperature for 3 hours. Conc. hydrochloric acid (10 ml) was added to the reaction mixture under ice-cooling, sodium bicarbonate (8 g) was added after 10 mins., the methanol then being distilled off in vacuo. The residue was extracted with chloroform, and the extract washed with water, dried with anhydrous sodium sulfate and concentrated in vacuo. The residue was washed with acetone and recrystallized from acetone to obtain the product as colorless crystals (3.8 g., yield: 50%, m.p.: 131°–133° C.

NMR (CDCl$_3$) δ(ppm: 100 (t, 3H, —CH$_2$CH$_2$CH$_3$), 1.55–1.90 (m, 4H, 6-H, —CH$_2$CH$_2$CH$_3$, 6-H$_2$, 7-H$_2$), 2.67–2.83 (m, 6H, —CH$_2$CH$_2$C$_3$, 5-H$_2$, 6-H$_2$), 13.09 (br. s, 1H, OH).

Mass (CI): 193 (M$^+$+1).

COMPARATIVE EXAMPLES 3–13

2-hydroxy-3-alkyl-5,6,7,8-tetrahydroquinoxaline 1,2-cyclohexanedione (6.72 g, 60 mM) was added all at once to a methanol solution (100 ml) of α-amino acidamide hydrochloride (50 mM) at −30° C., and aqueous 12N NaOH (10 ml) was added dropwise thereto. The reaction mixture was stirred for 30 mins., cooling was removed, and the mixture was stirred at room temperature for 5 hours. Conc. hydrochloric acid (12.5 ml) was added to the reaction mixture under ice-cooling, and sodium bicarbonate (10 g) was added after 10 mins., whereafter the methanol was distilled off in vacuo. The residue was extracted with chloroform, and the extract was washed with water, dried with anhydrous sodium sulfate and concentrated in vacuo. The residue was washed with acetone and recrystallized from acetone to obtain the product shown in Table 25.

The kind of product, yield (weight and %) and physical properties are shown in Table 25.

COMPARATIVE EXAMPLE 14

2-hydroxy-3-benzyl-5,6,7,8-tetrahydroquinoxaline

A methanol (30 ml) solution of 1,2-cyclohexanedione (13.44 g, 0.12M) was added to phenylalanineamide hydrochloride (20.05 g, 0.1M) dissolved in methanol (200 ml) under cooling below −30° C., and aqueous 12.5N NaOH (20 ml) was added dropwise thereto. The reaction mixture was stirred under −30° C. for 30 mins., whereafter cooling was removed and the mixture was stirred at room temperature for 3 hours. Conc. hydrochloric acid (25 ml) was added to the reaction mixture under ice-cooling, and sodium bicarbonate (15 g) was added after 10 mins. stirring, the methanol then being distilled off in vacuo. The residue, to which was added water, was extracted three times with chloroform, and the extract was washed with water, dried with anhydrous magnesium sulfate and concentrated in vacuo. The residue was washed with acetone and recrystallized from acetone to obtain the product (19.7 g, yield: 82.1%).

NMR (CDCl$_3$, TMS) δ(ppm): 1.6–2.0 (m, 4H), 2.4–2.7 (m, 4H), 4.02 (s, 2H), 7.0–7.4 (m, 5H).

Mass (CI): 241 (M$^+$+1).

COMPARATIVE EXAMPLE 15

2-hydroxy-3-(phenylethyl)-5,6,7,8-tetrahydroquinoxaline

A methanol (20 ml) solution of 1,2-cyclohexanedione (5.38 g) was added to a methanol suspension (100 ml) of α-amino-(3-phenyl)-butylamide hydrochloride (8.58 g, 40 mM) at below −30° C., and aqueous 12.5N NaOH (8 ml) was added dropwise thereto. The reaction mixture was stirred at below −30° C. for 30 mins., cooling was removed, and the mixture was stirred at room temperature for 6 hours. Conc. hydrochloric acid (8 ml) was added to the reaction mixture under ice-cooling, and sodium bicarbonate (6.0 g) was added after 10 mins. stirring, the methanol then being distilled off in vacuo. The residue, to which was added water, was extracted three times with chloroform, whereafter the extract was washed with water, dried with anhydrous sodium sulfate and concentrated in vacuo. The residue was washed with acetone and recrystallized from acetone to obtain the product (6.79 g, yield: 66.8%).

NMR (CDCl$_3$, TMS) δ(ppm): 1.6–2.0 (m, 4H), 2.5–2.8 (m, 4H), 3.06 (s, 2H×2), 7.1–7.3 (s, 5H), 12.9 (br. s, 1H).

Mass (CI): 225 (M$^+$+1).

COMPARATIVE EXAMPLES 16–23

2-hydroxy-3-alkyl-5,6-diethylpyrazine

α-amino acidamide (0.20M) and 3,4-hexane (22.8 g, 020M) were added to triethylamine (200 ml), the mixture was stirred at room temperature for 30 mins. and refluxed for 15 hours. Triethylamine was distilled off in vacuo, and the residue was dissolved in chloroform and washed with dilute aqueous K$_2$CO$_3$. The chloroform layer was dried with anhydrous sodium sulfate and concentrated in vacuo. The residue was recrystallized from acetone to obtain the products shown in Table 26.

Product, yield, (weight and %) and physical properties are shown in Table 26.

TABLE 6

| | | | 1-(2-substituted ethyl)-3,5,6-trimethyl-2-oxo-1,2-dihidropyrazine | | | | |
|---|---|---|---|---|---|---|---|
| Example | Product* | Base | Starting Material* | Heat time(hr) | Elution solvent ratio | Yield (g) | Yield (%) |
| 2 | 018 | HN⎡⎤CH$_2$ | 026 | 1.75 h | 20:1 | 1.96 | 78.5 |
| 3 | 019 | HN⎡⎤O | 026 | 4 | 40:1 | 1.61 | 64.1 |
| 4 | 020 | HN⎡⎤N—Me | 026 | 1.75 | 20:1 | 1.70 | 64.4 |
| 5 | 021 | HN⎡⎤N—CH$_2$CH$_2$—OH | 026 | 2 | 10:1 | 2.25 | 76.5 |
| 6 | 022 | 1-imidazole | 026 | 2 | 50:1 | 1.45 | 62.4 |

TABLE 6-continued

1-(2-substituted ethyl)-3,5,6-trimethyl-2-oxo-1,2-dihidropyrazine

| Example | Product* | Base | Starting Material* | Heat time(hr) | Elution solvent ratio | Yield (g) | Yield (%) |
|---|---|---|---|---|---|---|---|
| 7 | 023 | HN⎡⎤N—CH₂Ph | 026 | 5 | 100:1 | 2.42 | 71.2 |
| 8 | 024 | HN⎡⎤N—CH₂Ph—Cl(p) | 026 | 5 | 100:1 | 3.34 | 86.5 |
| 9 | 025 | HN⎡⎤N—CH₂Ph—Cl(o) | 026 | 5 | 100:1 | 3.64 | 97.2 |

*Compound No.

TABLE 7

1-(2-substituted thioththyl)-3,5,6-trimethyl-2-oxo-1,2-dihydropyrazine

| Example | Product° | Mercaptane | Starting material° | Yield (g) | Yield (%) |
|---|---|---|---|---|---|
| 10 | 027 | HS—Ph | 026 | 1.06 | 77.4 |
| 11 | 028 | 1-methyl-5-mercaptotetrazole | 026 | 1.04 | 78.8 |

*Compound No.

TABLE 8

1-(2-substituted ethyl)-3-phenyl-5,6-dimethyl-2-oxo-1,2-dihydropyrazine

| Example | Product° | Base | Starting material° | Heat time(hr) | Elution solvent ratio | Yield (g) | Yield (%) |
|---|---|---|---|---|---|---|---|
| 16 | 110 | HN⎡⎤O | 612 | 3 | 100:1 | 0.70 | 89.5 |
| 17 | 111 | HN⎡⎤N—CH₂Ph—Cl(p) | 612 | 3 | 100:1 | 0.99 | 91.0 |

*Compound No.

TABLE 9

1-(2-substituted ethyl)-3-benzyl-5,6-dimethyl-2-oxo-1,2-dihydropyrazine

| Example | Product° | Base | Starting material* | Heat time(hr) | Elution solvent ratio | Yield (g) | Yield (%) |
|---|---|---|---|---|---|---|---|
| 20 | 113 | HN⎡⎤O | 613 | 3 h | 100:1 | 0.78 | 79.5 |
| 21 | 114 | HN⎡⎤N—CH₂Ph | 613 | 2 | 100:1 | 1.07 | 85.5 |
| 22 | 115 | HN⎡⎤N—CH₂Ph—Cl(p) | 613 | 3 | 100:1 | 0.78 | 57.7 |

TABLE 9-continued 1-(2-substituted ethyl)-3-benzyl-5,6-dimethyl-2-oxo-1,2-dihydropyrazine

| Example | Product* | Base | Starting material* | Heat time(hr) | Elution solvent ratio | Yield (g) | Yield (%) |
|---|---|---|---|---|---|---|---|
| 23 | 116 | HN▭N—CH₂Ph—Cl(o) | 613 | 2 | 100:1 | 0.96 | 71.0 |

*Compound No.

TABLE 10

1-(2-hydroxyethyl)-3-alkyl-5,6-dimethyl-2-oxo-1,2-dihydropyrazine

| Example | Product* | Starting material ($R_1$) | | Reaction time (hr) | Elution solvent ratio | Yield (g) | Yield (%) |
|---|---|---|---|---|---|---|---|
| 24 | 616 | Pro | 3.32 g (20 mM) | 2 h | 100:1 | 3.42 | 81.4 |
| 25 | 622 | iso-Pro | 4.50 g (27 mM) | 2 | 100:1 | 4.32 | 76.2 |
| 26 | 624 | Bu | 2.70 g (15 mM) | 2 | 50:1 | 3.31 | 98.5 |
| 27 | 617 | iso-Bu | 5.40 g (30 mM) | 2 | 50:1 | 5.12 | 76.2 |
| 28 | 623 | sec-Bu | 4.50 g (25 mM) | 2 | 100:1 | 4.74 | 84.6 |

*Compound No.

TABLE 11

1-(2-substituted ethyl)-3-alkyl-5, 6-dimethyl-2-oxo-1, 2-dihydropyrazine

| Example | Product° | Base | Starting material* | Heat time (hr) | Elution solvent ratio | Yield (g) | Yield (%) |
|---|---|---|---|---|---|---|---|
| 29 | 121 | HN▭O | 616 | 1.5 h | 100:1 | 0.94 | 67.4 |
| 30 | 122 | HN▭N—CH₂Ph | 616 | 2 | 100:1 | 1.00 | 67.9 |
| 31 | 123 | HN▭O | 617 | 2.5 | 150:1 | 0.72 | 61.4 |
| 32 | 124 | HN▭N—CH₂Ph | 617 | 2 | 150:1 | 1.41 | 92.3 |
| 33 | 125 | HN▭N—CH₂Ph—Cl (p) | 617 | 1.5 | 150:1 | 1.58 | 94.8 |
| 34 | 126 | HN▭N—CH₂Ph—Cl (m) | 617 | 1.5 | 150:1 | 1.27 | 76.2 |
| 35 | 619 | HN▭N—CH₂Ph—F (p) | 617 | 1.5 | 150:1 | 1.16 | 72.5 |
| 36 | 148 | HN▭O | 622 | 1.5 | 200:1 | 0.94 | 84.2 |
| 37 | 149 | HN▭N—CH₂Ph | 622 | 1.5 | 200:1 | 1.42 | 96.5 |
| 38 | 150 | HN▭N—CH₂Ph—Cl (p) | 622 | 2 | 200:1 | 1.41 | 87.6 |

TABLE 11-continued

1-(2-substituted ethyl)-3-alkyl-5,6-dimethyl-2-oxo-1,2-dihydropyrazine

| Example | Product* | Base | Starting material* | Heat time (hr) | Elution solvent ratio | Yield (g) | Yield (%) |
|---|---|---|---|---|---|---|---|
| 39 | 151 | HN☐N—CH₂Ph—F (p) | 622 | 2 | 150:1 | 1.21 | 78.4 |
| 40 | 156 | HN☐O | 624 | 1.5 | 150:1 | 0.85 | 72.5 |
| 41 | 157 | HN☐N—CH₂Ph | 624 | 1.5 | 150:1 | 1.03 | 67.4 |
| 42 | 158 | HN☐N—CH₂Ph—Cl (p) | 624 | 1.5 | 150:1 | 1.08 | 64.8 |
| 43 | 152 | HN☐O | 623 | 1 | 150:1 | 0.49 | 41.8 |
| 44 | 153 | HN☐N—CH₂Ph | 623 | 1.25 | 150:1 | 0.64 | 41.9 |
| 45 | 154 | HN☐N—CH₂Ph—Cl (p) | 623 | 1.25 | 150:1 | 1.05 | 63.0 |
| 46 | 155 | HN☐N—CH₂Ph—F (p) | 623 | 1.5 | 150:1 | 1.12 | 70.0 |

*Compound No.

TABLE 12

1-(2-hydroxyethyl)-3-alkyl-2-oxo-1,2,5,6,7,8-hexahydro quinoxaline

| Example | Product* | Starting material (R₁) | | Reaction time (hr) | Elution solvent ratio | Yield (g) | Yield (%) |
|---|---|---|---|---|---|---|---|
| 47 | 614 | Pro | 6.26 g (32 mM) | 1.25 h | 50:1 | 7.15 | 94.7 |
| 48 | 621 | Bu | 5.15 g (25 mM) | 2 | 50:1 | 6.15 | 98.4 |
| 49 | 618 | iso-Bu | 4.12 g (20 mM) | 2 | 50:1 | 4.12 | 82.4 |

*; Compound No.

TABLE 13

1-(2-substituted ethyl)-3-alkyl-2-oxo-1,2,5,6,7,8-hexahydro quinoxaline

| Example | Product* | Base | Starting material* | Heat time (hr) | Elution solvent ratio | Yield (g) | Yield (%) |
|---|---|---|---|---|---|---|---|
| 50 | 118 | HN☐O | 614 | 3 h | 100:1 | 1.14 | 93.5 |
| 51 | 119 | HN☐N—CH₂Ph | 614 | 3 | 100:1 | 1.21 | 95.8 |
| 52 | 120 | HN☐N—CH₂Ph—Cl (p) | 614 | 2.5 | 100:1 | 1.57 | 91.9 |
| 53 | 117 | HN☐N—CH₂CH₂—OH | 614 | 2.5 | 50:1 | 0.70 | 62.2 |

TABLE 13-continued

1-(2-substituted ethyl)-3-alkyl-2-oxo-1,2,5,6,7,8-hexahydro quinoxaline

| Example | Product* | Base | Starting material* | Heat time (hr) | Elution solvent ratio | Yield (g) | Yield (%) |
|---|---|---|---|---|---|---|---|
| 54 | 127 | HN⏋O | 618 | 2.5 | 200:1 | 1.07 | 83.6 |
| 55 | 128 | HN⏋N—CH₂Ph | 618 | 1 | 200:1 | 1.58 | 96.8 |
| 56 | 129 | HN⏋N—CH₂Ph—Cl (p) | 618 | 1 | 200:1 | 1.46 | 82.5 |
| 57 | 141 | HN⏋O | 621 | 1 | 200:1 | 0.76 | 59.6 |
| 58 | 142 | HN⏋N—CH₂Ph | 621 | 1 | 200:1 | 0.95 | 58.2 |
| 59 | 143 | HN⏋N—CH₂Ph—Cl (p) | 621 | 2 | 200:1 | 1.49 | 84.2 |
| 60 | 144 | HN⏋CH₂ | 621 | 1 | 200:1 | 0.86 | 67.8 |
| 61 | 145 | HN⏋N—CH₂CH₂—OH | 621 | 2 | 50:1 | 0.92 | 63.5 |
| 62 | 146 | HN⏋N—CH₂Ph—F (p) | 621 | 1.25 | 200:1 | 1.15 | 67.5 |

*Compound No.

TABLE 14

1-(2-hydroxy ethyl)-3-alkyl-5,6-diethyl-2-oxo-1,2-dihydropyrazine

| Example | Product* | Starting material (R₁) | | Reaction time (hr) | Elution solvent ration | Yield (g) | Yield (%) |
|---|---|---|---|---|---|---|---|
| 63 | 620 | Pro | 7.76 g (40 mM) | 5.5 h | 50:1 | 6.89 | 73.3 |
| 64 | 625 | iso-Pro | 9.70 g (50 mM) | 5.5 | 100:1 | 8.70 | 73.1 |
| 65 | 628 | Bu | 10.40 g (50 mM) | 3 | 100:1 | 8.53 | 68.2 |
| 66 | 626 | iso-Bu | 5.20 g (25 mM) | 3 | 100:1 | 5.08 | 81.3 |
| 67 | 627 | sec-Bu | 10.40 g (50 mM) | 3 | 100:1 | 9.94 | 79.5 |
| 68 | 629 | Et | 4.50 g (25 mM) | 2 | 100:1 | 4.38 | 78.2 |

*Compound No.

TABLE 15

1-(2-substituted ethyl)-3-alkyl-5,6-diethyl-2-oxo-1,2-dihydropyrazine

| Example | Product* | Base | Starting material* | Heat time (hr) | Elution Solvent ratio | Yield (g) | Yield (%) |
|---|---|---|---|---|---|---|---|
| 69 | 130 | HN⏋O | 620 | 3h | 100:1 | 0.77 | 62.7 |

TABLE 15-continued 1-(2-substituted ethyl)-3-alkyl-5,6-diethyl-2-oxo-1,2-dihydropyrazine

| Example | Product* | Base | Starting material° | Heat time (hr) | Elution Solvent ratio | Yield (g) | Yield (%) |
|---|---|---|---|---|---|---|---|
| 70 | 131 | HN⎡⎤N—CH₂ Ph | 620 | 1.5 | 200:1 | 1.05 | 66.3 |
| 71 | 132 | HN⎡⎤N—CH₂ Ph—Cl (p) | 620 | 1.25 | 200:1 | 0.90 | 52.1 |
| 72 | 133 | HN⎡⎤N—CH₂ Ph—Cl (m) | 620 | 1.5 | 200:1 | 1.02 | 59.0 |
| 73 | 134 | HN⎡⎤N—CH₂ Ph—Cl (o) | 620 | 1.25 | 200:1 | 0.63 | 36.5 |
| 74 | 159 | HN⎡⎤O | 625 | 1.25 | 200:1 | 0.65 | 52.9 |
| 75 | 160 | HN⎡⎤N—CH₂ Ph | 625 | 1.25 | 200:1 | 0.74 | 46.8 |
| 76 | 161 | HN⎡⎤N—CH₂ Ph—Cl (p) | 625 | 1.25 | 200:1 | 0.99 | 57.5 |
| 77 | 162 | HN⎡⎤N—CH₂ Ph—F (p) | 625 | 1.25 | 200:1 | 0.55 | 33.2 |
| 78 | 163 | HN⎡⎤CH₂ | 625 | 1.25 | 200:1 | 0.55 | 45.1 |
| 79 | 164 | HN⎡⎤N—CH₂ CH₂—OH | 625 | 1.25 | 50:1 | 0.47 | 33.6 |
| 80 | 165 | HN⎡⎤N—CH₂ Ph—Cl (m) | 625 | 1.25 | 200:1 | 0.77 | 44.7 |
| 81 | 166 | HN⎡⎤N=CH₂ Ph—F (p) | 626 | 1.25 | 200:1 | 1.20 | 70.1 |
| 82 | 167 | HN⎡⎤O | 626 | 1.25 | 200:1 | 0.70 | 54.5 |

TABLE 15-continued 1-(2-substituted ethyl)-3-alkyl-5,6-diethyl-2-oxo-1,2-dihydropyrazine

| Example | Product* | Base | Starting material* | Heat time (hr) | Elution Solvent ratio | Yield (g) | Yield (%) |
|---|---|---|---|---|---|---|---|
| 83 | 168 | HN⏜N—CH$_2$Ph—Cl (p) | 626 | 1.25 | 200:1 | 1.17 | 65.6 |
| 84 | 170 | HN⏜N—CH$_2$Ph | 626 | 1.25 | 200:1 | 1.31 | 79.9 |
| 85 | 171 | HN⏜CH$_2$ | 627 | 1.25 | 200:1 | 0.33 | 25.9 |
| 86 | 172 | HN⏜N—CH$_2$CH$_2$—OH | 627 | 2 | 50:1 | 0.30 | 20.6 |
| 87 | 173 | HN⏜O | 627 | 1 | 200:1 | 0.68 | 53.0 |
| 88 | 174 | HN⏜N—CH$_2$Ph | 627 | 1 | 200:1 | 0.46 | 28.0 |
| 89 | 175 | HN⏜N—CH$_2$Ph—F (p) | 627 | 1.25 | 200:1 | 0.39 | 22.8 |
| 90 | 176 | HN⏜N—CH$_2$Ph—Cl (p) | 627 | 1 | 200:1 | 0.78 | 43.6 |
| 91 | 177 | HN⏜N—CH$_2$Ph—Cl (m) | 627 | 1.25 | 200:1 | 0.52 | 29.1 |
| 92 | 178 | HN⏜N—CH$_2$Ph—Cl (o) | 628 | 1.25 | 200:1 | 1.08 | 60.8 |
| 93 | 179 | HN⏜N—CH$_2$Ph | 628 | 1.25 | 200:1 | 0.92 | 56.1 |
| 94 | 180 | HN⏜N—CH$_2$Ph—Cl (p) | 628 | 1.25 | 200:1 | 1.54 | 86.7 |
| 95 | 181 | HN⏜CH$_2$ | 628 | 1 | 200:1 | 0.90 | 70.5 |

TABLE 15-continued

| | | | 1-(2-substituted ethyl)-3-alkyl-5,6-diethyl-2-oxo-1,2-dihydropyrazine | | | | |
|---|---|---|---|---|---|---|---|
| Example | Product* | Base | Starting material* | Heat time (hr) | Elution Solvent ratio | Yield (g) | Yield (%) |
| 96 | 182 | HN⎡⎤O | 628 | 1.25 | 200:1 | 0.98 | 76.3 |
| 97 | 183 | HN⎡⎤N—CH₂Ph—F (p) | 628 | 1.25 | 200:1 | 1.28 | 74.8 |
| 98 | 185 | HN⎡⎤N—CH₂Ph—Cl (m) | 628 | 1.25 | 200:1 | 0.78 | 43.9 |
| 99 | 187 | HN⎡⎤O | 629 | 2 | 200:1 | 0.86 | 77.6 |
| 100 | 188 | HN⎡⎤N—CH₂Ph—Cl (p) | 629 | 1.25 | 100:1 | 0.80 | 48.1 |
| 101 | 189 | HN⎡⎤N—CH₂Ph | 629 | 1.25 | 100:1 | 0.79 | 51.7 |

*Compound No.

TABLE 16

| | | | 1-(2-substituted ethyl)-3-ethyl-5,6-dimethyl-2-oxo-1,2-dihydropyrazine | | | | |
|---|---|---|---|---|---|---|---|
| Example | Product* | Base | Starting material* | Heat time (hr) | Elution solvent ration | Yield (g) | Yield (%) |
| 103 | 190 | HN⎡⎤O | 630 | 2 | 200:1 | 1.03 | 77.7 |
| 104 | 191 | HN⎡⎤N—CH₂Ph—Cl (p) | 630 | 2 | 200:1 | 1.54 | 79.3 |
| 105 | 192 | HN⎡⎤N—CH₂Ph—F (p) | 630 | 1.5 | 200:1 | 1.23 | 66.1 |
| 106 | 193 | HN⎡⎤N—CH₂Ph—OMe (p) | 630 | 2 | 200:1 | 1.70 | 88.5 |
| 107 | 287 | HN⎡⎤N—CH₂Ph | 630 | 1 | 200:1 | 1.37 | 77.4 |
| 108 | 288 | HN⎡⎤N—CH₂Ph—Cl (p) | 630 | 1 | 200:1 | 1.42 | 70.6 |

TABLE 16-continued

1-(2-substituted ethyl)-3-ethyl-5,6-dimethyl-2-oxo-1,2-dihydropyrazine

| Example | Product* | Base | Starting material* | Heat time (hr) | Elution solvent ration | Yield (g) | Yield (%) |
|---|---|---|---|---|---|---|---|
| 109 | 289 | HN〔 〕N—CH₂Ph—F (p) | 630 | 1 | 200:1 | 1.05 | 54.4 |
| 110 | 290 | HN〔 〕N—CH₂Ph—NO₂ (p) | 630 | 1.5 | 200:1 | 1.39 | 69.7 |

*Compound No.

TABLE 17

1 - (2-substituted ethyl)-3-benzyl-5,6-diethyl-2-oxo-1,2-dihydropyrazine

| Example | Product* | Base | Starting material* | Heat time (hr) | Elution solvent ratio | Yield (g) | Yield (%) |
|---|---|---|---|---|---|---|---|
| 112 | 291 | HN〔 〕O | 640 | 4 h | 100:1 | 1.15 | 81.0 |
| 113 | 292 | HN〔 〕CH₂ | 640 | 1 | 100:1 | 1.15 | 81.4 |
| 114 | 293 | HN〔 〕N—CH₂Ph | 640 | 3 | 100:1 | 1.11 | 62.5 |
| 115 | 294 | HN〔 〕N—CH₂Ph—Cl (p) | 640 | 2 | 100:1 | 1.60 | 83.6 |
| 116 | 295 | HN〔 〕N—CH₂Ph—Cl₂ (2,4) | 640 | 2.5 | 100:1 | 0.95 | 46.3 |
| 117 | 296 | HN〔 〕N—CH₂Ph—F (p) | 640 | 4 | 100:1 | 1.45 | 78.5 |
| 118 | 297 | HN〔 〕N—CH₂Ph—OMe (p) | 640 | 2.5 | 100:1 | 0.99 | 52.2 |
| 119 | 374 | HN〔 〕CH₂—Ph | 640 | 1 | 200:1 | 1.21 | 70.5 |
| 120 | 375 | HN〔 〕CH₂—Me | 640 | 1 | 200:1 | 0.99 | 67.4 |

TABLE 17-continued

1 - (2-substituted ethyl)-3-benzyl-5,6-diethyl-2-oxo-1,2-dihydropyrazine

| Example | Product* | Base | Starting material* | Heat time (hr) | Elution solvent ratio | Yield (g) | Yield (%) |
|---|---|---|---|---|---|---|---|
| 121 | 378 | HN⎡⎤N—CH$_2$Ph—NO$_2$ (p) | 640 | 1 | 100:1 | 1.57 | 80.3 |
| 122 | 380 | HN⎡⎤N—Ph | 640 | 2 | 200:1 | 0.73 | 42.4 |

*Compound No.

TABLE 18

1-(2-substituted ethyl)-3-p-chlorobenzyl-5,6-diethyl-2-oxo-1,2-dihydropyrazine

| Example | Product° | Base | Starting material° | Heat time (hr) | Elution solvent ratio | Yield (g) | Yield (%) |
|---|---|---|---|---|---|---|---|
| 125 | 384 | HN⎡⎤O | 641 | 2 | 100:1 | 0.89 | 76.2 |
| 126 | 467 | HN⎡⎤N—CH$_2$Ph | 641 | 2 | 100:1 | 1.10 | 76.6 |
| 127 | 385 | HN⎡⎤N—CH$_2$Ph—Cl (p) | 641 | 2 | 100:1 | 1.23 | 79.9 |
| 128 | 386 | HN⎡⎤N—CH$_2$Ph—OMe (p) | 641 | 2 | 100:1 | 1.15 | 75.4 |
| 129 | 387 | HN⎡⎤N—CH$_2$Ph—NO$_2$ (p) | 641 | 2 | 100:1 | 1.03 | 56.2 |

*Compound No.

TABLE 19

1-(2-hydroxyethyl)-3-alkyl-2-oxo-1,2,5,6,7,8-hexyahydro quinozaline

| Example | Product* | Starting material ($R_1$) | silica-gel | Elution solvent | Yield (g) | Yield (%) |
|---|---|---|---|---|---|---|
| 130 | 631 | —(CH$_2$)$_4$CH$_3$ 30 mM | 150 g | chloroform-methanol (200:1) | 6.44 | 81.3 |
| 131 | 632 | —(CH$_2$)$_5$CH$_3$ 20 mM | 100 g | chloroform-methanol (200:1) | 4.66 | 83.8 |
| 132 | 633 | —(CH$_2$)$_6$CH$_3$ 30 mM | 150 g | chloroform-methanol (200:1) | 8.39 | 95.8 |
| 133 | 634 | —(CH$_2$)$_7$CH$_3$ 28 mM | 150 g | chloroform-methanol (200:1) | 7.60 | 89.2 |
| 134 | 635 | —(CH$_2$)$_8$CH$_3$ 40 mM | 200 g | chloroform-methanol (200:1) | 11.00 | 85.9 |
| 135 | 636 | —(CH$_2$)$_9$CH$_3$ 30 mM | 150 g | chloroform-methanol (200:1) | 8.42 | 84.0 |
| 136 | 637 | —(CH$_2$)$_{11}$CH$_3$ 20 mM | 100 g | benzene-ethyl acetate (5:1→3:1) | 6.06 | 84.2 |
| 137 | 638 | —(CH$_2$)$_{13}$CH$_3$ 15 mM | 100 g | benzene-ethyl acetate (5:1) | 3.86 | 66.2 |
| 138 | 639 | —(CH$_2$)$_{15}$CH$_3$ 20 mM | 100 g | benzene-ethyle acetate (5:1→3:1) | 5.92 | 70.8 |

*; Compound No.

TABLE 20

1-(2-substituted ethyl)-3-alkyl-2-oxo-1,2,5,6,7,8-hexahydro quinoxaline

| Example | Product° | Starting material° | Base | Heat time (hr) | Yield (g) | Yield (%) |
|---|---|---|---|---|---|---|
| 139 | 250 | 631 1.06 g (4mM) | HN⎡⎤N—CH$_2$Ph—Cl (p) | 1.5 h | 1.59 | 87.1 |

TABLE 20-continued 1-(2-substituted ethyl)-3-alkyl-2-oxo-1,2,5,6,7,8-hexahydro quinoxaline

| Example | Product* | Starting material* | Base | Heat time (hr) | Yield (g) | Yield (%) |
|---|---|---|---|---|---|---|
| 140 | 251 | 631 | 1.06 g (4mM) | HN☐N—CH₂Ph—F (p) | 2 | 1.65 | 93.8 |
| 141 | 252 | 631 | 1.32 g (5mM) | HN☐O | 1.5 | 1.05 | 63.1 |
| 142 | 253 | 631 | 1.06 g (4mM) | HN☐N—Bu | 2 | 1.01 | 65.1 |
| 143 | 254 | 631 | 1.06 g (4mM) | HN☐N—CH₂Ph—OMe (p) | 1.5 | 1.35 | 74.7 |
| 144 | 255 | 632 | 1.25 g (4.5mM) | HN☐O | 2 | 1.34 | 85.8 |
| 145 | 256 | 632 | 0.95 g (3.5mM) | HN☐N—CH₂Ph—Cl (p) | 2 | 0.88 | 53.4 |
| 146 | 257 | 632 | 0.95 g (3.5mM) | HN☐N—CH₂Ph—NO₂ (p) | 2 | 1.50 | 89.1 |
| 147 | 258 | 632 | 1.12 g (4mM) | HN⋁⋁N—CH₂Ph—F (p) | 2 | 1.44 | 76.9 |
| 148 | 305 | 632 | 1.12 g (4mM) | HN☐N—Ph | 2 | 1.38 | 81.7 |
| 149 | 306 | 632 | 1.12 g (4mM) | HN☐N—CH₂Ph | 2 | 1.32 | 75.7 |
| 150 | 307 | 632 | 1.12 g (4mM) | HN☐N—CH₂Ph—F (p) | 2 | 1.49 | 83.9 |
| 151 | 308 | 632 | 1.12 g (4mM) | HN☐N—CH₂Ph—OMe (p) | 2 | 1.73 | 92.8 |
| 152 | 309 | 632 | 1.12 g (4mM) | HN☐N—Ph—Cl (o) | 2.5 | 1.38 | 75.6 |

TABLE 20-continued 1-(2-substituted ethyl)-3-alkyl-2-oxo-1,2,5,6,7,8-hexahydro quinoxaline

| Example | Product* | Starting material* | Base | | Heat time (hr) | Yield (g) | Yield (%) |
|---|---|---|---|---|---|---|---|
| 153 | 310 | 632 | 1.12 g (4mM) | HN⌐⌐N—Ph—OMe (o) | 2.5 | 1.43 | 79.1 |
| 154 | 311 | 632 | 1.12 g (4mM) | HN⌐⌐N—CH₂Ph—NO₂ (p) | 2.5 | 1.44 | 72.7 |
| 155 | 312 | 632 | 1.12 g (4mM) | HN⌐⌐N—CH₂Ph—Cl (p) | 2 | 1.49 | 76.9 |
| 156 | 313 | 632 | 1.12 g (4mM) | HN⌐⌐N—CH₂Ph—OMe (p) | 2 | 0.81 | 42.2 |
| 157 | 259 | 633 | 1.17 g (4mM) | HN⌐⌐O | 2 | 0.94 | 65.1 |
| 158 | 260 | 633 | 1.17 g (4mM) | HN⌐⌐N—CH₂Ph—Cl (p) | 2 | 1.03 | 53.4 |
| 159 | 261 | 633 | 1.17 g (4mM) | HN⌐⌐N—CH₂Ph—NO₂ (p) | 2 | 1.50 | 75.8 |
| 160 | 262 | 633 | 1.17 g (4mM) | HN⌐⌐N—CH₂Ph—F (p) | 2 | 1.28 | 68.4 |
| 161 | 263 | 633 | 1.17 g (4mM) | HN⌐⌐N—Bu | 2 | 0.85 | 51.1 |
| 162 | 264 | 633 | 1.17 g (4mM) | HN⌐⌐N—CH₂Ph—Cl (p) | 2 | 1.42 | 71.4 |
| 163 | 314 | 633 | 1.17 g (4mM) | HN⌐⌐N—CH₂Ph | 2 | 1.50 | 83.3 |
| 164 | 315 | 633 | 1.17 g (4mM) | HN⌐⌐N—Ph | 2 | 0.44 | 25.2 |
| 165 | 316 | 633 | 1.17 g (4mM) | HN⌐⌐N—Ph—OMe (o) | 2 | 1.70 | 93.3 |

TABLE 20-continued 1-(2-substituted ethyl)-3-alkyl-2-oxo-1,2,5,6,7,8-hexahydro quinoxaline

| Example | Product* | Starting material* | Base | Heat time (hr) | Yield (g) | Yield (%) |
|---|---|---|---|---|---|---|
| 166 | 317 | 633 1.17 g (4mM) | HN  N—Ph—Cl (o) | 2 | 1.30 | 69.1 |
| 167 | 318 | 633 1.17 g (4mM) | HN  N—CH₂Ph—F (p) | 2.5 | 1.11 | 57.6 |
| 168 | 319 | 633 1.17 g (4mM) | HN  N—CH₂Ph—OMe (p) | 2 | 1.01 | 51.1 |
| 169 | 320 | 633 1.17 g (4mM) | HN  N—CH₂Ph—NO₂ (p) | 1.5 | 1.29 | 63.4 |
| 170 | 265 | 634 1.23 g (4mM) | HN  O | 2 | 1.01 | 67.3 |
| 171 | 266 | 634 0.92 g (3mM) | HN  N—CH₂Ph—Cl (p) | 2 | 1.49 | 99.6 |
| 172 | 267 | 634 0.92 g (3mM) | HN  N—CH₂Ph—OMe (p) | 2 | 1.24 | 83.7 |
| 173 | 268 | 634 0.92 g (3mM) | HN  N—CH₂Ph—NO₂ (p) | 2 | 1.40 | 91.7 |
| 174 | 269 | 634 0.92 g (3mM) | HN  N—CH₂Ph—F (p) | 2 | 1.27 | 87.8 |
| 175 | 270 | 634 1.23 g (4mM) | HN  N—CH₂Ph—F (p) | 2 | 1.18 | 59.5 |
| 176 | 321 | 634 1.23 g (4mM) | HN  N—CH₂Ph | 2 | 1.79 | 96.4 |
| 177 | 322 | 634 1.23 g (4mM) | HN  N—Ph | 2 | 1.58 | 87.8 |
| 178 | 323 | 634 1.23 g (4mM) | HN  N—Ph—OMe (o) | 3 | 1.90 | 99.0 |

TABLE 20-continued

1-(2-substituted ethyl)-3-alkyl-2-oxo-1,2,5,6,7,8-hexahydro quinoxaline

| Example | Product* | Starting material* | Base | Heat time (hr) | Yield (g) | Yield (%) |
|---|---|---|---|---|---|---|
| 179 | 324 | 634 | 1.23 g (4mM) HN─N─Ph─Cl (o) | 2 | 1.54 | 79.5 |
| 180 | 325 | 634 | 1.23 g (4mM) HN─N─CH₂Ph─NO₂ (p) | 2 | 1.45 | 69.3 |
| 181 | 326 | 634 | 1.23 g (4mM) HN─N─CH₂Ph─OMe (p) | 2 | 1.33 | 65.5 |
| 182 | 327 | 634 | 1.23 g (4mM) HN─N─CH₂Ph─Cl (p) | 2 | 1.41 | 68.8 |
| 183 | 271 | 635 | 1.28 g (4mM) HN─O | 2 | 1.03 | 66.2 |
| 184 | 272 | 635 | 0.96 g (3mM) HN─N─CH₂Ph─Cl (p) | 2 | 1.15 | 74.8 |
| 185 | 273 | 635 | 0.96 g (3mM) HN─N─CH₂Ph─F (p) | 2 | 1.25 | 84.0 |
| 186 | 274 | 635 | 0.96 g (3mM) HN─N─CH₂Ph─NO₂ (p) | 2 | 1.15 | 73.3 |
| 187 | 275 | 635 | 0.96 g (3mM) HN─N─CH₂Ph─OMe (p) | 2 | 0.72 | 47.2 |
| 188 | 328 | 635 | 0.96 g (3mM) HN─N─CH₂Ph | 2 | 1.30 | 90.7 |
| 189 | 329 | 635 | 0.96 g (3mM) HN─N─CH₂Ph─Cl (p) | 2 | 0.87 | 55.1 |
| 190 | 330 | 635 | 0.96 g (3mM) HN─N─CH₂Ph─NO₂ (p) | 2.5 | 1.08 | 67.0 |
| 191 | 331 | 635 | 0.96 g (3mM) HN─N─CH₂Ph─F (p) | 2 | 0.61 | 39.9 |

TABLE 20-continued 1-(2-substituted ethyl)-3-alkyl-2-oxo-1,2,5,6,7,8-hexahydro quinoxaline

| Example | Product* | Starting material* | Base | Heat time (hr) | Yield (g) | Yield (%) |
|---|---|---|---|---|---|---|
| 192 | 332 | 635 | 0.96 g (3mM) HN⌐⌐N—CH₂Ph—OMe (p) | 2 | 1.04 | 66.4 |
| 193 | 334 | 636 | 1.01 g (3mM) HN⌐⌐O | 2 | 0.96 | 79.4 |
| 194 | 335 | 636 | 1.01 g (3mM) HN⌐⌐N—CH₂Ph | 2 | 1.28 | 86.6 |
| 195 | 336 | 636 | 1.01 g (3mM) HN⌐⌐N—Ph | 2 | 0.91 | 63.5 |
| 196 | 337 | 636 | 1.01 g (3mM) HN⌐⌐N—CH₂Ph—OMe (p) | 2.5 | 1.38 | 88.1 |
| 197 | 338 | 636 | 1.01 g (3mM) HN⌐⌐N—CH₂Ph—Cl (p) | 2 | 1.32 | 83.6 |
| 198 | 339 | 636 | 1.01 g (3mM) HN⌐⌐N—CH₂Ph—NO₂ (p) | 3 | 1.48 | 89.5 |
| 199 | 340 | 636 | 1.01 g (3mM) HN⌐⌐N—CH₂Ph—Cl (p) | 2 | 1.24 | |
| 200 | 276 | 637 | 1.09 g (3mM) HN⌐⌐O | 2 | 1.16 | 89.5 |
| 201 | 277 | 637 | 1.09 g (3mM) HN⌐⌐N—CH₂Ph—Cl (p) | 2 | 1.27 | 76.3 |
| 202 | 278 | 637 | 1.09 g (3mM) HN⌐⌐N—CH₂Ph—F (p) | 2 | 0.60 | 36.2 |
| 203 | 279 | 637 | 1.09 g (3mM) HN⌐⌐N—CH₂Ph—NO₂ (p) | 2 | 1.35 | 79.6 |
| 204 | 280 | 638 | 1.17 g (3mM) HN⌐⌐O | 2 | 0.91 | 66.1 |

TABLE 20-continued

1-(2-substituted ethyl)-3-alkyl-2-oxo-1,2,5,6,7,8-hexahydro quinoxaline

| Example | Product* | Starting material* | | Base | Heat time (hr) | Yield (g) | Yield (%) |
|---|---|---|---|---|---|---|---|
| 205 | 281 | 638 | 1.17 g (3mM) | HN⎡⎤N—CH₂Ph—OMe (p) | 2 | 1.21 | 69.8 |
| 206 | 282 | 638 | 1.17 g (3mM) | HN⎡⎤N—CH₂Ph—F (p) | 2 | 0.97 | 55.7 |
| 207 | 487 | 638 | 1.17 g (3mM) | HN⎡⎤N—CH₂Ph | 2 | 1.43 | 87.0 |
| 208 | 488 | 638 | 1.17 g (3mM) | HN⎡⎤N—CH₂Ph—NO₂ (p) | 3 | 0.89 | 48.9 |
| 209 | 489 | 638 | 1.17 g (3mM) | HN⎡⎤N—CH₂Ph—Cl (p) | 3 | 0.92 | 51.4 |
| 210 | 490 | 638 | 1.17 g (3mM) | HN⎡⎤N—CH₂Ph—OMe (p) | 2.5 | 0.98 | 55.2 |
| 211 | 283 | 639 | 1.26 g (3mM) | HN⎡⎤O | 2 | 1.22 | 83.5 |
| 212 | 284 | 639 | 1.26 g (3mM) | HN⎡⎤N—CH₂Ph—Cl (p) | 2 | 1.52 | 83.0 |
| 213 | 285 | 639 | 1.26 g (3mM) | HN⎡⎤N—CH₂Ph—NO₂ (p) | 2 | 1.77 | 95.0 |
| 214 | 286 | 639 | 1.26 g (3mM) | HN⎡⎤N—CH₂Ph—Cl (p) | 2 | 1.76 | 93.9 |

*Compound No.

TABLE 21

1-[2-(4'-acylpiperadinyl) ethyl]-3-ethyl-5,6-dimethyl-2-oxo-1,2-dihydropyrazine

| Example | Product° | Acylation Method | Acylating agent | Reaction time | Elution solvent ratio | Yield (g) | Yield (%) |
|---|---|---|---|---|---|---|---|
| 216 | 455 | acid chloride | ClCO—CH₂ Ph | 1 h | 100:1 | 0.93 | 81.2 |
| 217 | 457 | acid anhydride | 2-thienylchloride | 4 | 100:1 | 1.35 | 87.0 |
| 218 | 459 | acid anhydride | HOOC—CH₂ Ph-NO₂ (p) | 5 | 200:1 | 0.98 | 57.4 |
| 219 | 465 | acid chloride | ClSO₂—Ph-Cl (p) | 1 | 200:1 | 1.23 | 93.5 |
| 220 | 456 | acid anhydride | HOOC—Ph-Cl (p) | 2 | 100:1 | 1.49 | 92.5 |
| 221 | 458 | acid anhydride | HOOC—Ph-NO₂ (p) | 2 | 100:1 | 1.59 | 96.2 |
| 222 | 460 | acid chloride | HOOC—Ph-OMe (p) | 1 | 100:1 | 1.07 | 89.6 |
| 223 | 461 | acid anhydride | HOOC—Ph-OMe₂ (2,3) | 2 | 100:1 | 1.56 | 91.1 |
| 224 | 462 | acid anhydride | HOOC—Ph-OMe₂ (2,4) | 2 | 200:1 | 1.51 | 88.2 |
| 225 | 463 | acid anhydride | HOOC—Ph-OMe₂ (3,4) | 4 | 100:1 | 1.55 | 90.5 |

TABLE 21-continued

1-[2-(4′-acylpiperadinyl) ethyl]-3-ethyl-5,6-dimethyl-2-oxo-1,2-dihydropyrazine

| Example | Product* | Acylation Method | Acylating agent | Reaction time | Elution solvent ratio | Yield (g) | Yield (%) |
|---|---|---|---|---|---|---|---|
| 226 | 464 | acid anhydride | HOOC—Ph-OMe$_3$ (3,4,5) | 3 | 100:1 | 1.40 | 99.0 |

*; Compound No.

TABLE 22

1-(2-substituted ethyl)-3-benzyl-2-oxo-1,2,5,6,7,8-hexahydro quinoxaline

| Compound | Product* | Base | Starting material* | Heat time (hr) | Elution solvent ratio | Yield (g) | Yield (%) |
|---|---|---|---|---|---|---|---|
| 229 | 470 | HN⌐⌐O | 643 | 3 h | 100:1 | 0.67 | 52.6 |
| 230 | 471 | HN⌐⌐N—CH$_2$Ph | 643 | 3 | 100:1 | 1.01 | 62.3 |
| 231 | 472 | HN⌐⌐N—Ph | 643 | 3 | 200:1 | 0.82 | 54.7 |
| 232 | 473 | HN⌐⌐N—CH$_2$Ph—Cl (p) | 643 | 3 | 200:1 | 1.10 | 66.0 |
| 233 | 474 | HN⌐⌐N—CH$_2$Ph—OMe (p) | 643 | 2.5 | 100:1 | 0.93 | 56.3 |
| 234 | 475 | HN⌐⌐N—CH$_2$Ph—F (p) | 643 | 2.75 | 100:1 | 1.15 | 71.4 |

*Compound No.

TABLE 23

1-(2-substituted ethyl)-3-(2-phenylethyl)-2-oxo-1,2,5,6,7,8-hexahydro quinoxaline

| Example | product* | Base | Starting material* | Heat time (hr) | Elution solvent ratio | Yield (g) | Yield (%) |
|---|---|---|---|---|---|---|---|
| 237 | 476 | HN⌐⌐O | 645 | 2 h | 100:1 | 1.07 | 83.3 |
| 238 | 477 | HN⌐⌐N—CH$_2$Ph | 645 | 2 | 100:1 | 1.35 | 84.6 |
| 239 | 478 | HN⌐⌐N—Ph | 645 | 2 | 200:1 | 1.01 | 65.2 |
| 240 | 479 | HN⌐⌐N—CH$_2$Ph—Cl(p) | 645 | 2.5 | 100:1 | 1.41 | 82.0 |

TABLE 23-continued 1-(2-substituted ethyl)-3-(2-phenylethyl)-2-oxo-1,2,5,6,7,8-hexahydro quinoxaline

| Example | product* | Base | Starting material* | Heat time (hr) | Elution solvent ratio | Yield (g) | Yield (%) |
|---|---|---|---|---|---|---|---|
| 241 | 480 | HN◯N—CH$_2$Ph—OMe(p) | 645 | 2.5 | 100:1 | 0.98 | 57.6 |

*Compound No.

TABLE 24

1-(2-substituted ethyl)-3-(2-phenylethyl)-2-oxo-1,2,5,6,7,8-hexahydro quinoxaline

| Example | Product* | Base | Starting material* | Heat time (hr) | Elution solvent ratio | Yield (g) | Yield (%) |
|---|---|---|---|---|---|---|---|
| 243 | 481 | HN◯O | 646 | 2.5 h | 100:1 | 0.98 | 62.6 |
| 244 | 482 | HN◯N—CH$_2$Ph—Cl(p) | 646 | 2.5 | 100:1 | 1.54 | 74.3 |
| 245 | 483 | HN◯N—CH$_2$Ph | 646 | 2 | 100:1 | 1.67 | 87.9 |
| 246 | 484 | HN◯N—Ph | 646 | 2.5 | 200:1 | 1.29 | 70.5 |
| 247 | 485 | HN◯N—CH$_2$Ph—Cl(p) | 646 | 2 | 100:1 | 1.25 | 58.3 |
| 248 | 486 | HN◯N—CH$_2$Ph—OMe(p) | 646 | 3 | 100:1 | 1.78 | 86.8 |

*Compound No.

TABLE 25

2-hydroxy-3-alkyl-5,6,7,8-tetrahydro quinoxaline

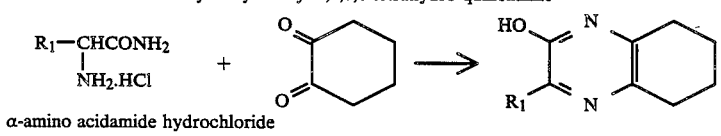

α-amino acidamide hydrochloride

| Comp. Exa. | Product (R$_1$) | Yield (g) | Yield (%) | NMR (CDCl$_3$) δ (ppm) | Mass |
|---|---|---|---|---|---|
| 3 | Bu | 7.49 | 73.0 | 0.94 (t, 3H, butyl 4-CH$_3$), 1.24~2.00 (m, butyl 2-CH$_2$, 3-CH$_2$, quinoxaline 6-H$_2$, 7-H$_2$), 2.55~2.85 (m, 6H, butyl 1-CH$_2$, quinoxaline 5-H$_2$, 8-H$_2$), 12.99 (br. s, 1H, OH) | 207 (M$^+$ + 1) |
| 4 | iso-Bu | 6.58 | 64.0 | 0.96 (d, 6H, isobutyl 2 × CH$_3$), 1.6~2.0 (m, 4H, 6-H$_2$, 7-H$_2$), 2.0~2.4 (isobutyl CH), 2.5~2.8 (m, 6H, 5-H$_2$, 8-H$_2$) | 207 (M$^+$ + 1) |
| 5 | —(CH$_2$)$_4$CH$_3$ | 9.03 | 82.0 | 0.90 (t, 3H, J ≈ 6.3), 1.2~1.5 (m, 4H), 1.5~1.9 (m, 6H), 2.5~2.9 (m, 6H) | 221 (M$^+$ + 1) 164 |
| 6 | —(CH$_2$)$_5$CH$_3$ | 7.81 | 66.7 | 0.88 (t, 3H, J ≈ 7.9), 1.1~1.5 (m, 6H), 1.5~2.0 (m, 6H), 2.4~2.9 (m, 6H) | 235 (M$^+$ + 1) |
| 7 | —(CH$_2$)$_5$CH$_3$ | 9.33 | 75.0 | 0.88 (t, 3H, J ≈ 7.4), 1.1~1.5 (m, 8H), 1.5~2.0 (m, 6H), 2.5~2.9 (m, 6H) | 249 (M$^+$ + 1) |
| 8 | —(CH$_2$)$_7$CH$_3$ | 11.67 | 89.1 | 0.88 (t, 3H, J ≈ 7.5), 1.1~1.5 (m, 10H), 1.5~2.0 (m, 6H), 2.5~2.9 (m, 6H) | 263 (M$^+$ + 1) |

TABLE 25-continued 2-hydroxy-3-alkyl-5,6,7,8-tetrahydro quinoxaline

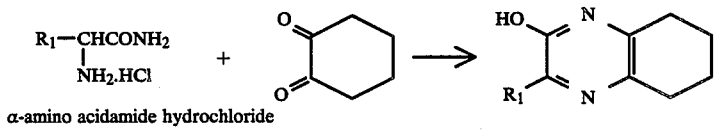

α-amino acidamide hydrochloride

| Comp. Exa. | Product (R₁) | Yield (g) | Yield (%) | NMR (CDCl₃) δ (ppm) | Mass |
|---|---|---|---|---|---|
| 9 | —(CH₂)₈CH₃ | 12.73 | 92.2 | 0.88 (t, 3H, J ≈ 6.2), 1.1~1.5 (m, 12H), 1.5~2.0 (m, 6H), 2.5~2.8 (m, 6H) | 277 (M⁺ + 1) 164 |
| 10 | —(CH₂)₉CH₃ | 10.46 | 72.4 | 0.88(t, 3H, J ≈ 6.0), 1.2~2.0 (m, 20H), 2.5~2.9 (m, 6H), 12.7 (br. s, 1H) | 291 (M⁺ + 1) |
| 11 | —(CH₂)₁₁CH₃ | 14.00 | 88.1 | 0.88 (t, 3H, J ≈ 6), 1.1~1.9 (m, 24H), 2.4~2.8 (m, 6H) | 319 (M⁺ + 1) 164 |
| 12 | —(CH₂)₁₃CH₃ | 16.58 | 95.8 | 0.88 (t, 3H, J ≈ 6), 1.1~1.9 (m, 28H), 2.4~2.8 (m, 6H) | 347 (M⁺ + 1) 164 |
| 13 | —(CH₂)₁₅CH₃ | 18.55 | 99.2 | 0.88 (t, 3H, J ≈ 6), 1.1~1.9 (m, 32H), 2.5~2.8 (m, 6H) | 375 (M⁺ + 1) 164 |

TABLE 26

2-hydroxy-3-alkyl-5,6-diethylpyrazine

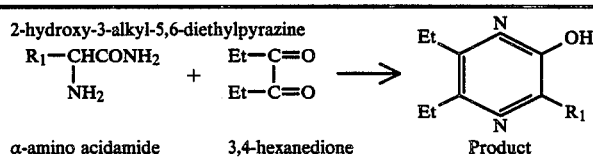

α-amino acidamide   3,4-hexanedione   Product

| Comp. Exa. | Product (R₁) | Yield (g) | Yield (%) | NMR (CDCl₃) δ (ppm) | Mass |
|---|---|---|---|---|---|
| 16 | Et | 14.4 | 40 | 1.1~1.4 (m, 9H), 2.3~3.0 (m, 6H), 13.2 (br. s, 1H) | 167 |
| 17 | Pro | 16.5 | 43 | 1.00 (t, 3H), 1.19 (t, 3H), 1.28 (t, 3H), 1.5~1.9 (m, 2H), 2.47 (q, 2H), 2.54 (q, 2H), 2.76 (q, 2H), 13.1 (br. s, 1H) | 181 |
| 18 | iso-Pro | 18.2 | 47 | 1.0~1.4 (m, 12H), 2.56 (q, 2H), 2.58 (q, 2H), 3.40 (sept, 1H), 12.9 (br. s, 1H) | 195 |
| 19 | Bu | 17.5 | 42 | 0.95 (t, 3H), 1.19 (t, 3H), 1.27 (t, 3H), 1.2~1.9 (m, 4H), 2.57 (q, 2H × 2), 2.73 (t, 3H), 12.9 (br. s, 1H) | 209 |
| 20 | iso-Bu | 16.5 | 40 | 0.96 (t, 3H), 1.19 (t, 3H), 1.28 (t, 3H), 1.9~2.4 (m, H), 2.41 (q, 2H), 2.58 (q, 2H), 2.66 (d, 2H), 13.0 (br. s, 1H) | 209 |
| 21 | sec-Bu | 17.5 | 42 | 0.88 (t, 3H × 2), 1.0~1.4 (m, 9H), 1.4~2.0 (m, 2H), 2.46 (q, 2H), 2.57 (q, 2H), 12.8 (br. s, 1H) | 209 |
| 22 | —CH₂Ph | 27.9 | 57.6 | 1.19 (t, 3H, J ≈ 7.6), 1.23 (t, 3H, J ≈ 7.6), 2.50 (q, 2H, J ≈ 7.6), 2.53 (q, 2H, J ≈ 7.6), 4.07 (s, 2H), 7.0~7.4 (m, 5H), 13.2 (br. s, 1H) | 243 |
| 23 | —CH₂Ph—Cl (p) | 27.4 | 49.6 | 1.19 (t, 3H, J ≈ 7.7), 1.23 (t, 3H, J ≈ 7.7), 2.53 (q, 2H, J ≈ 7.7), 2.57 (q, 2H, J ≈ 7.7), 4.03 (s, 2H), 7.0~7.4 (m, 4H), 13.3 (br. s, 1H) | 279 277 |

TABLE 27

| Compound Nos. | NMR (CDCl₃, TMS) δ | Mass | TLC |
|---|---|---|---|
| 018 | 1.3–1.8(6H, m), 2.30(3H, s), 2.41(3H, s), 2.5–2.8(6H, m), 4.1–4.3(2H, m) | 250(M⁺ +1) | 0.25 |
| 019 | 2.31(3H, s), 2.34(3H, s), 2.41(3H, s), 2.5–2.7(6H, m), 3.6–3.8(4H, m), 4.0–4.2(2H, m) | 252(M⁺ +1) | 0.31 |
| 020 | 2.29(3H×2, s), 2.34(3H, s), 2.41(3H, s), 2.3–2.9(10H, m), 4.0–4.2(2H, m) | 265(M⁺ +1) | 0.10 |
| 021 | 2.30(3H, s), 2.34(3H, s), 2.41(3H, s), 2.4–2.7(12H, m), 2.92(1H, s), 2.63(2H, t, J= 5.4), 4.0–4.2(2H, m) | 295(M⁺ +1) | 0.08 |
| 022 | 1.79(3H, s), 2.24(3H, s), 2.45(3H, s), 4.2–4.4(4H, m), 6.7–6.8(1H, m), 7.0–7.1(1H, m) 7.2–7.4(1H, m) | 233(M⁺ +1) | 0.30 |
| 023 | 2.30(3H, s), 2.33(3H, s), 2.41(3H, s), 2.3–2.7(10H, m), 3.54(2H, s), 4.0–4.2(2H, m), 7.30(5H, s) | 341(M⁺ +1) | 0.35 |
| 024 | 2.30(3H, s), 2.33(3H, s), 2.41(3H, s), 2.3–2.7(10H, m), 3.47(2H, s), 4.0–4.2(2H, m), 7.24(4H, s) | 375 377 (M⁺ +1) | 0.36 |
| 025 | 2.30(3H, s), 2.34(3H, s), 2.41(3H, s), 2.57(8H, s), 2.5–2.7(2H, m), 3.62(2H, s), 4.0–4.2(2H, m), 7.1–7.5(4H, m) | 375 377 (M⁺ +1) | 0.36 |
| 026 | 2.29(3H, s), 2.35(3H, s), 2.38(3H, s), 3.4(1H, bs), 3.8–4.0(2H, m), 4.1–4.3(2H, s) | 183(M⁺ +1) | 0.26 |
| 027 | 2.21(3H, s), 2.25(3H, s), 2.38(3H, s), 3.1–3.3(2H, m), 4.1–4.3(2H, m), 7.1–7.6(5H, m) | 275(M⁺ +1) | 0.48 |
| 028 | 2.32(3H, s), 2.43(3H, s), 2.46(3H, s), 3.4–3.7(2H, m), 3.95(3H, s), 4.3–4.6(2H, m) | 281(M⁺ +1) | 0.39 |
| 061 | 2.06(3H, s), 2.32(3H, s), 2.34(3H, s), 2.42(3H, s), 4.31(2H, t, J=3.3), 4.33(2H, t, J= 3.3) | 225(M⁺ +1) | 0.31 |
| 062 | 2.31(3H×2, s), 2.41(3H, s), 2.79(3H, d, J=5.4), 4.1–4.4(4H, m), 4.8–5.0(1H, bm) | 240(M⁺ +1) | 0.31 |
| 063 | 2.21(3H, s), 2.25(3H, s), 2.31(3H, s), 4.1–4.4(4H, m), 4.8–5.0(1H, b), 6.9–7.5(5H, m) | 302(M⁺ +1) | 0.41 |
| 064 | 2.20(3H, s), 2.25(3H, s), 2.31(3H, s), 4.2–4.4(4H, m), 4.8–5.0(1H, b), 7.1–7.5(4H, m) | 338(M⁺ +1) 336 | 0.42 |
| 101 | 2.30(3H×2, s), 2.33(3H×2, s), 2.58(3H×2,s), 2.58(8H, s), 2.5–2.7(4H, m), 4.0–4.2( | 415(M⁺ +1) | 0.13 |

TABLE 27-continued

| Compound Nos. | NMR (CDCl₃, TMS) δ | Mass | TLC |
|---|---|---|---|
| 109 | 4H, m)<br>2.38(3H, s), 2.41(3H, s), 3.97(2H, t, J=5.2), 4.25(2H, t, J=5.2), 7.2-7.5(3H, m), 8.1-8.2(2H, m) | 265(M⁺ +1) | 0.34 |
| 110 | 2.42(3H×2, s), 2.4-2.8(6H, m), 3.6-3.8(4H, m), 4.25(2H, t, J=6.9), 7.3-7.5(3H, m), 8.1-8.3(2H, m) | 314(M⁺ +1)<br>227 | 0.40 |
| 111 | 2.41(3H×2, s), 2.3-2.8(10H, m), 3.46(2H, s), 4.23(2H, t, J=6.1), 7.27(4H, s), 7.2-7.4(2H, m), 8.1-8.3(2H, m) | 441 439<br>(M⁺ +1) | 0.40 |
| 112 | 2.32(3H×2, s), 3.90(2H, t, J=5.3), 4.08(2H, s), 4.20(2H, t, J=5.3), 7.1-7.5(5H, m) | 258(M⁺ +1) | 0.34 |
| 113 | 2.31(3H×2, s), 2.4-2.7(6H, m), 3.5-3.7(4H, m), 4.08(2H, s), 4.0-4.2(2H, m), 7.1-7.5(5H, m) | 328(M⁺ +1)<br>241<br>114 | 0.35 |
| 114 | 2.30(3H×2, s), 2.3-2.7(10H, m), 3.51(2H, s), 4.08(2H, s), 3.9-4.2(2H, m), 7.1-7.4(10H, m) | 417(M⁺ +1) | 0.32 |
| 115 | 2.30(3H×2, s), 2.3-2.7(10H, m), 3.45(2H, s), 4.08(2H, s), 3.9-4.2(2H, m), 7.1-7.4(9H, m) | 452(M⁺ +1)<br>450<br>223 | 0.35 |
| 116 | 2.31(3H×2, s), 2.4-2.7(10H, m), 3.62(2H, s), 4.08(2H, s), 4.0-4.2(2H, m), 7.1-7.9(9H, m) | 452(M⁺ +1)<br>450<br>223 | 0.38 |
| 117 | 0.99(3H, t, J=7.3), 1.5-2.0(6H, m), 2.0-2.3(2H, m), 2.4-2.8(16H, m), 3.5-3.7(2H, m), 3.9-4.2(2H, m) | 349(M⁺ +1) | 0.08 |
| 118 | 0.99(3H, t, J=7.3), 1.5-2.0(6H, m), 2.4-2.9(12H, m), 3.5-3.8(4H, m), 3.9-4.2(2H, m) | 306(M⁺ +1)<br>219<br>214 | 0.43 |
| 119 | 0.98(3H, t, J=7.3), 1.7-2.0(6H, m), 2.3-2.9(16H, m), 3.51(2H, s), 3.9-4.2(2H, m), 7.29(5H, s) | 395(M⁺ +1)<br>189 | 0.40 |
| 120 | 0.99(3H, t, J=7.3), 1.7-2.0(6H, m), 2.3-2.9(16H, m), 3.47(2H, s), 3.9-4.2(2H, m), 7.26(4H, s) | 429(M⁺ +1)<br>431 | 0.38 |
| 121 | 0.99(3H, t, J=7.3), 1.5-1.9(2H, m), 2.31(3H, s), 2.33(3H, s), 2.4-2.8(8H, m), 3.6-3.8(4H, m), 4.0-4.3(2H, m) | 280(M⁺ +1)<br>193 | 0.33 |
| 122 | 0.98(3H, t, J=7.3), 1.5-1.9(2H, m), 2.30(2H×3, s), 2.4-2.8(12H, m), 3.51(2H, s), 4.0-4.2(2H, m), 7.29(5H, s) | 369((M⁺ +1)<br>193 | 0.22 |
| 123 | 0.94(3H×2, d, J=6.6), 1.9-2.4(1H, m), 2.31(3H, s), 2.33(3H, s), 2.4-2.7(8H, m), 3.6-3.8(4H, m), 4.0-4.3(2H, m) | 294(M⁺ +1)<br>207<br>114<br>102 | 0.40 |
| 124 | 0.93(3H×2, d, J=6.6), 1.9-2.4(1H, m), 2.17(3H, s), 2.31(3H, s), 2.4-2.7(12H, m), 3.51(2H, s), 4.0-4.3(2H, m), 7.30(5H, s) | 383(M⁺ +1)<br>207 | 0.31 |
| 125 | 0.93(3H×2, d, J=6.6), 1.9-2.4(1H, m), 2.31(3H×2, s), 2.3-2.8(12H, m), 3.46(2H, s), 4.0-4.3(2H, m), 7.26(4H, s) | 419(M⁺ +1)<br>417<br>207<br>125 | 0.29 |
| 126 | 0.94(3H×2, d, J=6.6), 1.9-2.4(1H, m), 2.31(3H×2, s), 2.3-2.8(12H, m), 3.47(2H, s), 4.0-4.3(2H, m), 7.26(4H, s) | 419(M⁺ +1)<br>417<br>207<br>125 | 0.31 |
| 127 | 0.95(3H×2, d, J=6.6), 1.7-1.9(4H, m), 2.0-2.2(1H, m), 2.5-2.8(12H, m), 3.6-3.8(4H, m), 4.0-4.2(2H, m) | 320(M⁺ +1)<br>233<br>114<br>102 | 0.39 |
| 128 | 0.94(3H×2, d, J=6.6), 1.6-2.0(4H, m), 2.0-2.4(1H, m), 2.3-2.8(16H, m), 3.51(2H, s), 3.9-4.2(2H, m), 7.29(5H, s) | 409(M⁺ +1)<br>233<br>189 | 0.38 |
| 129 | 0.94(3H, d, J=6.4), 0.96(3H, d, J=6.4), 1.6-2.0(4H, m), 2.0-2.4(1H, m), 2.3-2.8(16H, m), 7.45(2H, s), 3.8-4.3(2H, m), 7.26(4H, s) | 445(M⁺ +1)<br>443<br>233<br>125 | 0.37 |
| 130 | 0.99(3H, t, J=7.3), 1.21(3H, t, J=7.6), 1.23(2H, t, J=7.6), 1.5-2.0(2H, m), 2.4-2.9(12H, m), 3.6-3.8(4H, m), 4.0-4.3(2H, m) | 308(M⁺ +1)<br>221<br>102 | 0.37 |
| 131 | 0.99(3H, t, J=7.2), 1.20(3H, t, J=7.5), 1.4-1.9(2H, m), 2.2-2.8(16H, m), 3.51(2H, s), 3.8-4.3(2H, m), 7.29(5H, s) | 397(M⁺ +1)<br>221 | 0.38 |
| 132 | 0.99(3H, t, J=7.2), 1.21(3H×2, t, J=7.6), 1.5-2.0(2H, m), 2.3-2.9(16H, m), 3.48(2H, s), 3.9-4.3(2H, m), 7.26(4H, s) | 433(M⁺ +1)<br>431<br>307<br>221<br>125 | 0.31 |
| 133 | 0.99(3H, t, J=7.2), 1.20(3H×2, t, J=7.6), 1.4-2.1(2H, m), 2.3-2.9(16H, m), 3.48(2H, s), 4.0-4.3(2H, m), 7.1-7.4(4H, m) | 433(M⁺ +1)<br>431<br>239<br>221<br>125 | 0.28 |
| 134 | 0.99(3H, t, J=7.8), 1.20(3H, t, J=7.6), 1.21(3H, t, J=7.6), 1.4-2.1(2H, m), 2.4-2.9(16H, m), 2.64(2H, s), 4.0-4.3(2H, m), 7.1-7.5(4H, m) | 433(M⁺ +1)<br>431<br>221<br>125 | 0.32 |
| 141 | 0.94(3H, t, J=6.4), 1.2-2.0(8H, m), 2.4-2.9(12H, m), 3.6-3.8(4H, m), 3.9-4.2(2H, m) | 320(M⁺ +1) | 0.44 |
| 142 | 0.93(3H, t, J=6.4), 1.2-2.0(8H, m), 2.3-2.9(16H, m), 3.51(2H, s), 3.9-4.3(2H, m), 7.29(5H, s) | 409(M⁺ +1)<br>189 | 0.47 |
| 143 | 0.93(3H, t, J=6.4), 1.2-2.0(8H, m), 2.3-2.9(16H, m), 3.46(2H, s), 3.9-4.2(2H, m), 7.26(4H, s) | 445(M⁺ +1)<br>443 | 0.46 |

TABLE 27-continued

| Compound Nos. | NMR (CDCl₃, TMS) δ | Mass | TLC |
|---|---|---|---|
| | | 225 | |
| | | 223 | |
| | | 125 | |
| 144 | 0.93(3H, t, J=6.4), 1.2-2.0(14H, m), 2.4-2.9(12H, m), 4.0-4.3(2H, m) | 318(M⁺ +1) | 0.33 |
| | | 223 | |
| | | 111 | |
| 145 | 0.93(3H, t, J=6.4), 1.2-2.0(8H, m), 2.0-2.9(16H, m), 3.61(2H, t, J=5.2), 3.9-4.2(2H, m) | 363(M⁺ +1) | 0.09 |
| | | 143 | |
| | | 125 | |
| 146 | 0.93(3H, t, J=6.4), 1.2-2.0(8H, m), 2.3-2.9(16H, m), 3.46(2H, s), 3.9-4.2(2H, m), 6.8-7.1(2H, m), 7.1-7.3(2H, m) | 427(M⁺ +1) 207 | 0.42 |
| 148 | 1.21(3H×2, d, J=6.9), 2.32(3H×2, s), 2.4-2.7(6H, m), 3.42(1H, sept, J=6.9), 3.6-3.8 (2H, m), 3.8-4.4(4H, m) | 280(M⁺ +1) 114 | 0.40 |
| 149 | 1.23(3H, d, J=6.9), 1.24(3H, d, J=6.9), 2.30(3H, s), 2.32(3H, s), 2.3-2.7(10H, m), 3.42(1H, sept, J=6.9), 3.52(2H, s), 3.9-4.2(2H, m), 7.29(5H, s) | 369(M⁺ +1) 204 | 0.39 |
| 150 | 1.23(3H, d, J=6.9), 1.25(3H, d, J=6.9), 2.30(3H, s), 2.32(3H, s), 2.3-2.7(10H, m), 3.42(1H, sept, J=6.9), 3.46(2H, s), 3.8-4.3(2H, m), 7.26(4H,s) | 405(M⁺ +1) 403 223 | 0.38 |
| 151 | 1.23(3H, d, J=6.9), 1.24(3H, d, J=6.9), 2.30(3H, s), 2.32(3H, s), 2.3-2.7(10H, m), 3.42(1H, sept, J=6.9), 3.47(2H, s), 3.9-4.2(2H, m), 6.8-7.1(2H, m), 7.1-7.3(2H, m) | 413(M⁺ +1) | 0.39 |
| 152 | 0.88(3H, t, J=7.4), 1.11(3H, d, J=6.9), 1.3-2.0(2H, m), 2.32(3H×2, s), 2.4-2.8(8H, m) 3.0-3.5(1H, m), 3.6-3.8(4H, m), 4.0-4.4(2H, m) | 294(M⁺ +1) 114 102 | 0.44 |
| 153 | 0.88(3H, t, J=7.4), 1.17(3H, d, J=6.9), 1.2-2.0(2H, m), 2.30(3H, s), 2.32(3H, s), 2.3-2.7(10H, m), 3.0-3.4(1H, m), 3.51(2H, s), 3.8-4.3(2H, m), 7.29(5H, s) | 383(M⁺ +1) 189 | 0.38 |
| 154 | 0.88(3H, t, J=7.4), 1.17(3H, d, J=6.9), 1.2-2.0(2H, m), 2.31(3H×2, s), 2.3-2.7(10H, m), 3.0-3.5(1H, m), 3.47(2H, s), 3.8-4.3(2H, m), 7.26(4H, s) | 419(M⁺ +1) 417 223 | 0.34 |
| 155 | 0.88(3H, t, J=7.4), 1.17(3H, d, J=6.8), 1.3-2.0(2H, m), 2.31(3H×2, s), 2.3-2.7(10H, m), 3.0-3.5(1H, m), 3.47(2H, s), 4.0-4.3(2H, m), 7.1-7.3(2H, m) | 401(M⁺ +1) 207 | 0.36 |
| 156 | 0.94(3H, t, J=6.7), 1.2-1.8(4H, m), 2.31(3H, s), 2.33(3H, s), 2.3-2.9(8H, m), 3.6-3.8 (4H, m), 4.0-4.3(2H, m) | 294(M⁺ +1) 207 114 102 | 0.42 |
| 157 | 0.93(3H, t, J=6.7), 1.2-1.9(4H, m), 2.30(3H, s), 2.33(3H, s), 2.3-2.9(12H, m), 3.51 (2H, s), 3.9-4.2(2H, m), 7.29(5H, s) | 383(M⁺ +1) 207 | 0.41 |
| 158 | 0.93(3H, t, J=6.7), 1.2-1.8(4H, m), 2.30(3H, s), 2.32(3H, s), 2.3-2.9(12H, m), 3.47 (2H, s), 3.9-4.3(2H, m), 7.26(4H, s) | 419(M⁺ +1) 417 207 125 | 0.46 |
| 159 | 1.1-1.4(12H, m), 2.4-2.8(10H, m), 3.42(1H, sept, J=6.8), 3.8-4.4(6H, m) | 308(M⁺ +1) 239 113 | 0.47 |
| 160 | 1.1-1.4(12H, m), 2.3-2.8(14H, m), 3.41(1H, sept, J=6.9), 3.52(2H, s), 3.8-4.3(2H, m), 7.29(5H, s) | 396(M⁺ +1) 189 | 0.49 |
| 161 | 1.1-1.4(12H, m), 2.4-2.8(14H, m), 3.41(1H, sept, J=6.8), 3.48(2H, s), 3.8-4.3(2H, m), 7.26(4H, s) | 433(M⁺ +1) 431 236 223 125 | 0.48 |
| 162 | 1.20(3H×2, t, J=7.3), 1.21(3H×2, d, J=6.8), 2.4-2.8(14H, m), 3.41(1H, sept, J=6.8), 3.48(2H, s), 3.9-4.3(2H, m), 6.8-7.1(2H, m), 7.1-7.3(2H, m) | 415(M⁺ +1) 207 | 0.43 |
| 163 | 1.0-1.7(18H, m), 2.4-2.8(10H, m), 3.42(1H, sept, J=6.8), 3.8-4.3(2H, m) | 306(M⁺ +1) 239 221 | 0.44 |
| 164 | 1.1-1.4(12H, m), 2.4-2.8(14H, m), 3.41(1H, sept, J=6.8), 3.48(2H, s), 3.9-4.3(2H, m), 6.8-7.1(2H, m), 7.1-7.3(2H, m) | 415(M⁺ +1) 207 | 0.13 |
| 165 | 1.1-1.4(12H, m), 2.4-2.8(14H, m), 3.42(1H, sept, J=6.8), 3.48(2H, s), 3.8-4.3(2H, m), 7.1-7.3(4H, m) | 433(M⁺ +1) 431 223 | 0.40 |
| 166 | 0.94(3H, d, J=6.7), 0.95(3H, d, J=6.7), 1.20(3H, t, J=7.4), 1.21(3H, t, J=7.4), 2.4-2.5 (1H, sept, J=6.7), 2.3-2.9(16H, m), 3.48(2H, s), 3.8-4.3(2H,m), 6.8-7.1(2H, m), 7.1-7.4(2H, m) | 429(M⁺ +1) 220 207 | 0.46 |
| 167 | 0.95(3H×2, d, J=6.4), 1.21(3H×2, t, J=7.4), 2.0-2.4(1H, m), 2.4-2.8(12H, m), 3.5-3.8 (4H, m), 4.0-4.3(2H, m) | 322(M⁺ +1) | 0.41 |
| 168 | 0.94(3H, d, J=6.7), 0.95(3H, d, J=6.7), 1.20(3H, t, J=7.3), 1.21(3H, t, J=7.3), 2.0-2.5 (1H, m), 2.3-2.9(16H, m), 3.47(2H, s), 3.9-4.3(2H, m), 7.26(4H, s) | 447(M⁺ +1) 445 223 | 0.44 |
| 170 | 0.94(3H×2, d, J=6.7), 1.20(3H, t, J=6.7), 1.21(3H, t, J=6.5), 2.0-2.4(1H, m), 2.3-2.8 (16H, m), 3.51(2H, s), 4.0-4.3(2H, m), 7.29(5H, m) | 411(M⁺ +1) 189 | 0.36 |
| 171 | 0.88(3H, t, J=7.4), 1.17(3H, d, J=6.8), 1.22(3H×2, t, J=7.2), 1.3-2.0(8H, m), 2.4-2.8 (10H, m), 3.0-3.4(1H, m), 4.1-4.3(2H, m) | 320(M⁺ +1) 111 | 0.38 |
| 172 | 0.88(3H, t, J=7.3), 1.17(3H, d, J=6.3), 1.21(3H×2, t, J=7.2), 1.4-2.0(2H, m), 2.3-2.8 (6H, m), 3.1-3.3(1H, m), 3.61(2H, t, J=5.4), 4.0-4.3(2H, m) | 365(M⁺ +1) 156 | 0.09 |
| 173 | 0.88(3H, t, J=7.5), 1.17(3H, d, J=6.8), 1.21(3H×2, t, J=7.1), 1.2-1.9(2H, m), 2.4-2.8 (10H, m), 3.1-3.4(1H, m), 3.6-4.0(4H, m), 4.0-4.3(2H, m) | 322(M⁺ +1) 103 | 0.42 |
| 174 | 0.87(3H, t, J=7.2), 1.16(3H, d, J=6.8), 1.20(3H×2, t, J=6.6), 1.3-1.9(2H, m), 2.4-2.8 (14H, m), 3.0-3.4(1H, m), 3.53(2H, s), 4.1-4.3(2H, m), 7.30(5H, s) | 411(M⁺ +1) | 0.43 |
| 175 | 0.87(3H, t, J=7.4), 1.1-1.3(9H, m), 1.3-2.0(2H, m), 2.4-2.7(14H, m), 3.0-3.4(1H, m), 3.47(2H, s), 3.9-4.3(2H, m), 6.8-7.1(2H, m), 7.1-7.3(2H, m) | 429(M⁺ +1) 220 | 0.42 |
| 176 | 0.88(3H, t, J=7.6), 1.17(3H, d, J=7.1), 1.21(3H×2, t, J=7.1), 1.4-2.0(2H, m), 2.3-2.8 | 447(M⁺ +1) | 0.42 |

TABLE 27-continued

| Compound Nos. | NMR (CDCl₃, TMS) δ | Mass | TLC |
|---|---|---|---|
| | (14H, m), 3.0-3.4(1H, m), 3.47(2H, s), 4.0-4.3(2H, m), 7.26(4H, s) | 445 223 | |
| 177 | 0.87(3H, t, J=7.2), 1.17(3H, d, J=6.8), 1.21(3H×2, t, J=6.9), 1.2-2.0(2H, m), 2.3-2.8 (14H, m), 3.1-3.4(1H, m), 3.48(2H, s), 4.0-4.3(2H, m), 7.1-7.4(4H, m) | 447(M⁺+1) 445 223 | 0.39 |
| 178 | 0.93(3H, t, J=6.4), 1.20(3H×2, t, J=7.4), 1.2-1.9(4H, m), 2.2-2.9(16H, m), 3.63(2H, s), 3.9-4.3(2H, m), 7.1-7.5(4H, m) | 447(M⁺+1) 445 223 | 0.43 |
| 179 | 0.93(3H, t, J=6.4), 1.20(3H×2, t, J=7.5), 1.2-1.9(4H, m), 2.2-2.8(16H, m), 3.52(2H, s), 3.9-4.3(2H, m), 7.29(5H, s) | 411(M⁺+1) 189 | 0.46 |
| 180 | 0.93(3H, t, J=6.4), 1.21(3H×2, t, J=7.4), 1.2-1.9(4H, m), 2.2-2.9(16H, m), 3.47(2H, s), 3.9-4.3(2H, m), 7.26(4H, s) | 447(M⁺+1) 445 223 | 0.43 |
| 181 | 0.94(3H, t, J=6.6), 1.20(3H, t, J=7.6), 1.23(3H, t, J=7.6), 1.2-1.9(10H, m), 2.4-2.9 (12H, m), 4.1-4.4(2H, m) | 320(M⁺+1) | 0.40 |
| 182 | 0.94(3H, t, J=6.6), 1.21(3H, t, J=7.6), 1.23(3H, t, J=7.6), 1.2-1.9(4H, m), 2.4-2.9( 12H, m), 3.6-4.0(4H, m), 3.9-4.3(2H, m) | 322(M⁺+1) 113 | 0.39 |
| 183 | 0.93(3H, t, J=6.6), 1.20(3H×2, t, J=7.5), 1.2-1.8(4H, m), 2.3-2.9(16H, m), 3.47(2H, s), 3.9-4.3(2H, m), 6.8-7.1(2H, m), 7.1-7.4(2H, m) | 429(M⁺+1) 207 | 0.42 |
| 185 | 0.94(3H, t, J=6.4), 1.21(3H×2, t, J=7.4), 1.2-1.8(4H, m), 2.2-2.9(16H, m), 3.48(2H, s), 4.0-4.3(2H, m) | 447(M⁺+1) 445 223 | |
| 187 | 1.22(3H×2, t, J=7.3), 1.23(3H, t, J=7.3), 2.4-2.9(12H, m), 3.6-3.8(4H, m), 3.8-4.3( 2H, m), | 294(M⁺+1) 207 | 0.39 |
| 188 | 1.21(3H×2, t, J=7.3), 1.22(3H, t, J=7.3), 2.3-2.9(16H, m), 3.48(2H, s), 3.8-4.3(2H, m), 7.26(4H, s) | 419(M⁺+1) 417 225 | 0.40 |
| 189 | 1.21(3H×2, t, J=7.3), 1.22(3H, t, J=7.3), 2.4-2.9(16H, m), 3.54(2H, s), 3.8-4.3(2H, m), 7.29(5H, s) | 383(M⁺+1) 189 | 0.40 |
| 190 | 1.23(3H, t, J=7.5), 2.32(3H×2, s), 2.2-2.7(6H, m), 2.78(2H, q, J=7.5), 3.6-4H, m), 4.16(2H, t, J=7.2) | 266(M⁺+1) 179 174 | 0.56 |
| 191 | 1.22(3H, t, J=7.5), 2.31(3H×2, s), 2.3-2.7(10H, m), 2.78(2H, q, J=7.5), 3.46(2H, s), 3.9-4.3(2H, m), 7.26(4H, s) | 391(M⁺+1) 389 | 0.49 |
| 192 | 1.22(3H, t, J=7.5), 2.31(3H, s), 2.33(3H, s), 2.3-2.7(10H, m), 2.78(2H, q, J=7.5), 3.47(2H, s), 3.9-4.3(2H, m), 6.8-7.3(4H, m) | 373(M⁺+1) 207 179 | 0.42 |
| 193 | 1.22(3H, t, J=7.5), 2.31(3H, s), 2.33(3H, s), 2.3-2.7(10H, m), 2.78(2H, q, J=7.5), 3.45(2H, s), 3.79(3H, s), 3.8-4.2(2H, m), 6.7-6.9(2H, m), 7.1-7.3(2H, m) | 385(M⁺+1) 219 | 0.50 |
| 250 | 0.89(3H, t, J=6.5), 1.1-1.9(10H, m), 2.3-2.8(16H, m), 3.47(2H, s), 3.8-4.2(2H, m), 7.26(4H, s) | 459(M⁺+1) 457 247 223 | 0.36 |
| 251 | 0.89(3H, t, J=6.5), 1.1-1.9(10H, m), 2.3-2.8(16H, m), 3.48(2H, s), 3.8-4.2(2H, s), 6.8-7.3(4H, m) | 441(M⁺+1) 247 207 | 0.35 |
| 252 | 0.89(3H, t, J=6.5), 1.1-1.5(4H, m), 1.5-1.9(6H, m), 2.4-2.8(12H, m), 3.5-3.7(4H, m), 3.8-4.2(2H, m) | 334(M⁺+1) 114 | 0.35 |
| 253 | 0.8-1.0(6H, m), 1.1-1.9(14H, m), 2.2-2.8(18H, m), 3.9-4.1(2H, m) | 389(M⁺+1) 155 125 | 0.29 |
| 254 | 0.89(3H, t, J=6.5), 1.1-1.9(10H, m), 2.3-2.8(16H, m), 3.47(2H, s), 3.80(3H, s), 3.8-4.2(2H, m), 6.84(2H, d, J=8.6), 7.22(2H, d, J=8.6) | 453(M⁺+1) 247 219 111 | 0.34 |
| 255 | 0.88(3H, t, J=6.3), 1.1-1.9(12H, m), 2.4-2.9(12H, m), 3.6-3.8(4H, m), 3.9-4.2(2H, m) | 348(M⁺+1) 113 | 0.51 |
| 256 | 0.87(3H, t, J=6.3), 1.1-1.9(12H, m), 2.3-2.8(16H, m), 3.47(2H, s), 3.9-4.2(2H, m), 7.26(4H, s) | 473 471 (M⁺+1) 238 236 112 | 0.49 |
| 257 | 0.87(3H, t, J=6.3), 1.1-1.9(12H, m), 2.3-2.8(16H, m), 3.59(2H, s), 3.9-4.2(2H, m), 7.50(2H, d, J=8.8), 8.16(2H, d, J=8.8) | 482(M⁺+1) 347 234 112 | 0.42 |
| 258 | 0.87(3H, t, J=6), 1.2-2.0(14H, m), 2.5-2.9(16H, m), 3.60(2H, s), 3.9-4.2(2H, s), 6.8-7.4(4H, m) | 469(M⁺+1) 235 221 | 0.46 |
| 259 | 0.87(3H, t, J=6.5), 1.1-1.9(14H, m), 2.4-2.9(12H, m), 3.4-3.8(4H, m), 3.9-4.2(2H, m) | 362(M⁺+1) 114 | 0.41 |
| 260 | 0.87(3H, t, J=6), 1.1-1.9(14H, m), 2.3-2.9(16H, m), 3.47(2H, s), 3.9-4.2(2H, m), 7.26(4H, s) | 485 487 (M⁺+1) 223 | 0.40 |
| 261 | 0.87(3H, t, J=6), 1.1-1.9(14H, m), 2.4-2.8(16H, m), 3.59(2H, s), 3.9-4.2(2H, m), 7.49(2H, d, J=8.8), 8.17(2H, d, J=8.8) | 496(M⁺+1) 234 | 0.46 |
| 262 | 0.87(3H, t, J=6), 1.1-1.9(14H, m), 2.3-2.9(16H, m), 3.49(2H, s), 3.9-4.1(2H, m), 6.8-7.3(4H, m) | 469(M⁺+1) 275 207 | 0.42 |
| 263 | 0.8-1.0(6H, m), 1.1-1.6(12H, m), 1.5-1.9(6H, m), 2.1-2.9(18H, m), 3.9-4.2(2H, m) | 417(M⁺+1) 155 | 0.43 |

TABLE 27-continued

| Compound Nos. | NMR (CDCl$_3$, TMS) δ | Mass | TLC |
|---|---|---|---|
| 264 | 0.87(3H, t, J=6), 1.1–2.0(16H, m), 2.5–2.9(16H, m), 3.59(2H, s), 3.9–4.2(2H, m), 7.27(4H, s) | 498 500 (M$^+$ +1) 250 237 | 0.45 |
| 265 | 0.87(3H, t, J=6), 1.1–1.9(16H, m), 2.4–2.9(12H, m), 3.6–3.8(4H, m), 3.9–4.2(2H, m) | 376(M$^+$ +1) 114 | 0.47 |
| 266 | 0.87(3H, t, J=6), 1.1–1.9(16H, m), 2.3–2.9(16H, m), 3.47(2H, s), 3.9–4.2(2H, m), 7.26(4H, s) | 499 501 (M$^+$ +1) 289 223 | 0.43 |
| 267 | 0.87(3H, t, J=6), 1.1–2.0(16H, m), 2.3–2.9(16H, m), 3.46(2H, s), 3.80(3H, s), 3.9–4.1(2H, m), 6.84(2H, d, J=8.6), 7.22(2H, d, J=8.6) | 495(M$^+$ +1) 232 | 0.42 |
| 268 | 0.87(3H, t, J=6), 1.1–2.0(16H, m), 2.3–2.9(16H, m), 3.59(2H, s), 3.8–4.2(2H, m), 7.5(2H, d, J=8.8), 8.17(2H, d, J=8.8) | 510(M$^+$ +1) 234 | 0.46 |
| 269 | 0.87(3H, t, J=6), 1.1–2.0(16H, m), 2.3–2.9(16H, m), 3.47(2H, s), 3.9–4.2(2H, m), 6.8–7.3(4H, m) | 483(M$^+$ +1) 289 207 | 0.51 |
| 270 | 0.87(3H, t, J=6), 1.1–2.0(18H, m), 2.5–2.9(16H, m), 3.59(2H, s), 3.9–4.1(2H, m), 6.8–7.3(4H, m) | 497(M$^+$ +1) 235 221 | 0.45 |
| 271 | 0.87(3H, t, J=6), 1.1–1.9(18H, m), 2.4–2.9(12H, m), 3.6–3.8(4H, m), 3.9–4.2(2H, m) | 390(M$^+$ +1) | 0.48 |
| 272 | 0.87(3H, t, J=6), 1.1–1.9(18H, m), 2.3–2.9(16H, m), 3.46(2H, s), 3.9–4.2(2H, m), 7.26(4H, s) | 513 515 (M$^+$ +1) 223 | 0.51 |
| 273 | 0.87(3H, t, J=6), 1.1–1.9(18H, m), 2.4–2.9(16H, m), 3.46(2H, s), 3.9–4.2(2H, m), 6.8–7.3(4H, m) | 497(M$^+$ +1) 207 | 0.48 |
| 274 | 0.87(3H, t, J=6), 1.1–1.9(18H, m), 2.3–2.9(16H, m), 3.59(2H, s), 3.9–4.3(2H, m), 7.50(2H, d, J=8.8), 8.17(2H, d, J=8.8) | 524(M$^+$ +1) 247 234 | 0.52 |
| 275 | 0.87(3H, t, J=6), 1.1–2.0(18H, m), 2.3–2.9(16H, m), 3.47(2H, s), 3.80(3H, s), 3.9–4.2(2H, m), 6.85(2H, d, J=8.8), 7.23(2H, d, J=8.8) | 509(M$^+$ +1) 232 219 | 0.43 |
| 276 | 0.87(3H, t, J=6), 1.1–1.9(24H, m), 2.4–2.9(12H, m), 3.6–3.8(4H, m), 3.9–4.2(2H, m) | 432(M$^+$ +1) | 0.45 |
| 277 | 0.87(3H, t, J=6), 1.1–2.0(24H, m), 2.3–2.9(16H, m), 3.47(2H, s), 3.9–4.2(2H, m), 7.26(4H, s) | 555 557 (M$^+$ +1) 345 236 223 | 0.44 |
| 278 | 0.87(3H, t, J=6), 1.1–2.0(26H, m), 2.5–2.9(16H, m), 3.59(2H, s), 3.9–4.1(2H, m), 6.8–7.3(4H, m) | 553(M$^+$ +1) 235 221 | 0.46 |
| 279 | 0.87(3H, t, J=6), 1.1–2.0(24H, m), 2.3–2.9(16H, m), 3.58(3H, m), 3.9–4.3(2H, m), 7.49(2H, d, J=8.6), 8.17(2H, d, J=8.6) | 566(M$^+$ +1) 431 247 112 | 0.47 |
| 280 | 0.88(3H, t, J=6), 1.1–1.9(28H, m), 2.4–2.9(12H, m), 3.5–3.7(4H, m), 3.9–4.2(2H, m) | 460(M$^+$ +1) 114 | 0.53 |
| 281 | 0.88(3H, t, J=6), 1.1–2.0(28H, m), 2.3–2.9(16H, m), 3.45(2H, s), 3.79(3H, s), 3.9–4.2(2H, m), 6.84(2H, d, J=8.7), 7.22(2H, d, J=8.7) | 579(M$^+$ +1) 232 219 | 0.44 |
| 282 | 0.88(3H, t, J=6), 1.1–2.0(30H, m), 2.5–2.9(16H, m), 3.59(3H, s), 3.9–4.1(2H, m), 6.8–7.3(4H, m) | 581(M$^+$ +1) 234 221 | 0.50 |
| 283 | 0.88(3H, t, J=6), 1.1–1.7(32H, m), 2.4–2.9(12H, m), 3.5–3.7(4H, m), 3.9–4.2(2H, m) | 488(M$^+$ +1) 114 | 0.54 |
| 284 | 0.88(3H, t, J=6), 1.1–2.0(32H, m), 2.3–2.9(16H, m), 3.46(2H, s), 3.9–4.2(2H, m), 7.26(4H, s) | 611 613 (M$^+$ +1) 279 236 | 0.50 |
| 285 | 0.88(3H, t, J=6), 1.1–2.0(32H, m), 2.3–2.9(16H, m), 3.58(2H, s), 3.9–4.2(2H, m), 7.49(2H, d, J=8.8), 8.19(2H, d, J=8.8) | 622(M$^+$ +1) 419 208 | 0.50 |
| 286 | 0.88(3H, t, J=6), 1.1–2.0(34H, m), 2.5–2.9(16H, m), 3.59(2H, s), 3.8–4.1(2H, m), 7.26(4H, s) | 627 625 (M$^+$ +1) 307 250 | 0.48 |
| 287 | 1.23(3H, t, J=7.5), 2.31(3H×2, s), 2.3–3.0(12H, m), 3.51(2H, s), 3.9–4.3(2H, m), 7.29(5H, s) | 355(M$^+$ +1) 179 | 0.49 |
| 288 | 1.23(3H, t, J=7.5), 1.6–1.9(2H, m), 2.31(3H×2, s), 2.4–3.0(12H, m), 3.59(2H, s), 3.9–4.2(2H, m), 7.27(4H, s) | 391(M$^+$ +1) 389 | 0.40 |
| 289 | 1.23(3H, t, J=7.5), 1.6–1.9(2H, m), 2.31(3H×2, s), 2.4–3.0(12H, m), 3.60(2H, s), 3.9–4.2(2H, m), 6.8–7.4(4H, m) | 387(M$^+$ +1) 225 221 179 | 0.39 |
| 290 | 1.23(3H, t, J=7.5), 2.31(3H×2, s), 2.3–3.0(12H, m), 3.59(2H, s), 3.9–4.3(2H, m), 7.50(2H, d, J=8.7), 8.17(2H, d, J=8.7) | 400(M$^+$ +1) 234 179 | 0.44 |
| 291 | 1.21(3H×2, t, J=7.6), 2.4–2.8(10H, m), 3.5–3.7(2H, m), 3.8–4.2(4H, m), 4.09(2H, s), 7.0–7.4(5H, m) | 356 | 0.36 |
| 292 | 1.18(3H, t, J=7.6), 1.20(3H, t, J=7.6), 1.3–1.8(6H, m), 2.3–2.8(10H, m), 3.8–4.3(2H, m), 4.09(2H, s), 7.0–7.5(5H, m) | 354 | 0.40 |

TABLE 27-continued

| Compound Nos. | NMR (CDCl₃, TMS) δ | Mass | TLC |
|---|---|---|---|
| 293 | 1.18(3H, t, J=7.6), 1.20(3H, t, J=7.6), 2.3–2.8(14H, m), 3.50(2H, s), 3.8–4.2(2H, m), 4.08(2H, s), 7.0–7.4(10H, m) | 444 202 189 | 0.36 |
| 294 | 1.18(3H, t, J=7.6), 1.20(3H, t, J=7.6), 2.3–2.8(14H, m), 3.45(2H, s), 3.8–4.2(2H, m), 4.08(2H, s), 7.0–7.4(9H, m) | 479, 481 236 | 0.36 |
| 295 | 1.19(3H, t, J=7.6), 1.20(3H, t, J=7.6), 2.3–2.8(14H, m), 3.56(2H, s), 4.09(2H, s), 3.8–4.2(2H, m), 7.0–7.4(8H, m) | 513,515 517 237 219 | 0.60 |
| 296 | 1.18(3H, t, J=7.6), 1.20(3H, t, J=7.6), 2.2–2.8(14H, m), 3.45(2H, s), 3.8–4.2(2H, m), 4.08(2H, s), 6.8–7.4(9H, m) | 462 207 | 0.37 |
| 297 | 1.18(3H, t, J=7.6), 1.20(3H, t, J=7.6), 2.2–2.7(14H, m), 3.43(2H, s), 3.79(3H, s), 3-8–4.2(2H, m), 4.08(2H, s), 6.83(2H, d, J=8.8), 7.0–7.4(7H, m) | 474 232 219 | 0.37 |
| 305 | 0.87(3H, t, J=5.7), 1.2–2.0(12H, m), 2.4–2.9(12H, m), 3.0–3.4(6H, m), 4.0–4.3(2H, m), 7.1–7.3(5H, m) | 423,422 174 | 0.65 |
| 306 | 0.87(3H, t, J=5.7), 1.2–2.0(12H, m), 2.3–2.9(16H, m), 3.51(2H, s), 3.9–4.2(2H, m), 7.29(5H, s) | 437 189 | 0.36 |
| 307 | 0.87(3H, t, J=5.7), 1.2–2.0(12H, m), 2.3–2.9(16H, m), 3.46(2H, s), 3.9–4.2(2H, m), 6.8–7.4(14H, m) | 455 207 | 0.38 |
| 308 | 0.87(3H, t, J=5.7), 1.2–2.0(12H, m), 2.3–2.9(16H, m), 3.45(2H, s), 3.79(3H, s), 3.9–4.2(2H, m), 6.84(2H, d, J=8.6), 7.22(2H, d, J=8.6) | 467 219 | 0.40 |
| 309 | 0.87(3H, t, J=5.7), 1.2–2.0(12H, m), 2.6–2.9(12H, m), 3.0–3.2(4H, m), 4.0–4.3(2H, m), 6.8–7.4(4H, m) | 457,459 209 | 0.36 |
| 310 | 0.87(3H, t, J=5.7), 1.2–2.0(12H, m), 2.6–2.9(12H, m), 3.0–3.2(4H, m), 3.89(3H, s), 4.0–4.3(2H, m), 7.7–8.1(4H, m) | 453 203 | 0.53 |
| 311 | 0.87(3H, t, J=5.6), 1.2–2.0(14H, m), 2.6–3.0(16H, m), 3.72(2H, s), 3.9–4.2(2H, m), 7.51(2H, d, J=8.8), 8.17(2H, d, J=8.8) | 496 301 248 | 0.43 |
| 312 | 0.87(3H, t, J=5.6), 1.2–2.0(14H, m), 2.5–3.0(16H, m), 3.59(2H, s), 3.9–4.2(2H, m), 7.28(4H, s) | 485,487 237 | 0.49 |
| 313 | 0.87(3H, t, J=5.6), 1.2–2.0(14H, m), 2.6–2.9(16H, m), 3.58(2H, s), 3.80(3H, s), 3.9–4.2(2H, m), 6.84(2H, d, J=8.8), 7.24(2H, d, J=8.8) | 481 247 233 | 0.48 |
| 314 | 0.87(3H, t, J=5.7), 1.1–1.9(14H, m), 2.3–2.9(16H, m), 3.51(2H, s), 3.9–4.1(2H, m), 7.30(5H, s) | 451 189 | 0.48 |
| 315 | 0.87(3H, t, J=5.6), 1.1–1.9(14H, m), 2.5–2.9(12H, m), 3.1–3.3(4H, m), 4.0–4.2(2H, m), 6.7–8.3(5H, m) | 437 189 175 | 0.60 |
| 316 | 0.87(3H, t, J=5.6), 1.1–2.0(14H, m), 2.5–2.9(12H, m), 2.9–3.2(4H, m), 3.86(3H, s), 3.9–4.2(2H, m), 6.7–7.1(4H, m) | 467 203 | 0.65 |
| 317 | 0.87(3H, t, J=5.6), 1.1–2.0(14H, m), 2.5–2.9(12H, m), 2.9–3.2(4H, m), 4.0–4.2(2H, m), 6.7–7.4(4H, m) | 471,473 209 | 0.72 |
| 318 | 0.87(3H, t, J=5.6), 1.1–2.0(16H, m), 2.5–2.9(16H, m), 3.59(2H, s), 3.9–4.1(2H, m), 6.8–7.3(4H, m) | 483 221 | 0.40 |
| 319 | 0.87(3H, t, J=5.6), 1.2–2.0(16H, m), 2.5–3.0(16H, m), 3.58(2H, s), 3.8(3H, s), 3.9–4.2(2H, m), 6.84(2H, d, J=8.8), 7.24(2H, d, J=8.8) | 495 246,247 | 0.44 |
| 320 | 0.87(3H, t, J=5.6), 1.1–2.0(16H, m), 2.5–2.9(16H, m), 3.72(2H, s), 3.9–4.1(2H, m), 7.51(2H, d, J=8.8), 8.17(2H, d, J=8.8) | 510 | 0.45 |
| 321 | 0.87(3H, t, J=5.6), 1.0–2.0(16H, m), 2.3–2.8(16H, m), 3.51(2H, s), 3.9–4.2(2H, m), 7.29(5H, s) | 465 189 | 0.50 |
| 322 | 0.87(3H, t, J=6), 1.0–2.0(16H, m), 2.5–2.9(12H, m), 3.0–3.3(4H, m), 4.0–4.2(2H, m), 6.7–7.4(5H, m) | 451 175 | 0.55 |
| 323 | 0.87(3H, t, J=6), 1.1–2.0(16H, m), 2.5–2.9(12H, m), 2.9–3.2(4H, m), 3.58(3H, s), 4.0–4.2(2H, m), 6.7–7.1(4H, m) | 481 205 | 0.57 |
| 324 | 0.87(3H, t, J=6), 1.0–2.0(16H, m), 2.5–2.9(12H, m), 2.9–3.2(4H, m), 4.0–4.2(2H, m), 6.8–7.4(4H, m) | 485,487 209 | 0.52 |
| 325 | 0.87(3H, t, J=5.6), 1.1–2.0(18H, m), 2.5–3.0(16H, m), 3.72(2H, s), 3.9–4.2(2H, m), 7.51(2H, d, J=8.8), 8.17(2H, d, J=8.8) | 523 339 248 | 0.41 |
| 326 | 0.87(3H, t, J=6), 1.1–2.2(18H, m), 2.5–3.0(16H, m), 3.58(2H, s), 3.80(3H, s), 3.9–4.2(2H, m), 6.84(2H, d, J=8.8), 7.24(2H, d, J=8.8) | 509 247 233 | 0.41 |
| 327 | 0.87(3H, t, J=6), 1.1–2.2(18H, m), 2.5–3.0(16H, m), 3.59(2H, s), 3.9–4.2(2H, m), 7.26(4H, s) | 513,515 237 | 0.43 |
| 328 | 0.87(3H, t, J=6), 1.2–2.2(18H, m), 2.4–2.9(16H, m), 3.51(2H, s), 3.9–4.2(2H, m), 7.29(5H, s) | 479 189 | 0.48 |
| 329 | 0.87(3H, t, J=6), 1.1–2.1(20H, m), 2.4–3.0(16H, m), 3.59(2H, s), 3.9–4.2(2H, m), 7.26(4H, s) | 527,529 237 | 0.49 |
| 330 | 0.87(3H, t, J=6), 1.1–2.2(20H, m), 2.5–3.0(16H, m), 3.72(2H, s), 3.9–4.2(2H, m), 7.51(2H, d, J=8.8), 8.17(2H, d, J=8.8) | 538 402 | 0.51 |
| 331 | 0.87(3H, t, J=6), 1.1–2.2(20H, m), 2.5–3.0(16H, m), 3.60(2H, s), 3.9–4.2(2H, m), 6.8–7.4(4H, m) | 511 220 | 0.45 |
| 332 | 0.87(3H, t, J=6), 1.1–2.2(20H, m), 2.5–3.0(16H, m), 3.58(2H, s), 3.80(3H, s), 3.9–4.2(2H, m), 6.84(2H, d, J=8.4), 7.24(2H, d, J=8.4) | 523 247 233 | 0.43 |
| 334 | 0.87(3H, t, J=6), 1.1–2.0(20H, m), 2.3–2.9(12H, m), 3.5–3.8(4H, m), 3.9–4.2(2H, m) | 404 102 | 0.46 |
| 335 | 0.87(3H, t, J=6), 1.1–2.2(20H, m), 2.3–2.9(16H, m), 3.51(2H, s), 3.9–4.2(2H, m), 7.29(5H, s) | 493 189 | 0.47 |
| 336 | 0.87(3H, t, J=6), 1.0–2.0(20H, m), 2.5–2.9(12H, m), 3.0–3.3(4H, m), 3.9–4.2(2H, m), | 479 | 0.54 |

TABLE 27-continued

| Compound Nos. | NMR (CDCl₃, TMS) δ | Mass | TLC |
|---|---|---|---|
| | 6.7–7.4(4H, m) | 190 | |
| | | 175 | |
| 337 | 0.87(3H, t, J=6), 1.0–2.0(20H, m), 2.1–2.9(16H, m), 3.45(2H, s), 3.79(3H, s), 3.9–4.2(2H, m), 6.84(2H, d, J=8.8), 7.12(2H, d, J=8.8) | 523 232 219 | 0.47 |
| 338 | 0.87(3H, t, J=6), 1.0–2.2(20H, m), 2.3–2.9(16H, m), 3.9–4.2(2H, m), 7.26(4H, s) | 527,529 235 223 | 0.48 |
| 339 | 0.87(3H, t, J=6), 1.0–2.0(22H, m), 2.5–3.0(16H, m), 3.72(2H, s), 3.9–4.2(2H, m), 7.51(2H, d, J=8.8), 8.17(2H, d, J=8.8) | 552 417 248 | 0.49 |
| 340 | 0.87(3H, t, J=6), 1.1–2.1(22H, m), 2.5–3.0(16H, m), 3.60(2H, s), 3.9–4.2(2H, m), 7.27(4H, s) | 541,543 251 237 | 0.48 |
| 374 | 1.21(3H×2, t, J=7.6), 1.7–2.0(4H, m), 2.1–3.3(11H, m), 4.10(2H, s), 4.1–4.3(2H, m), 7.1–7.5(10H, m) | 430 134 | 0.74 |
| 375 | 0.91(3H, d, J=4.9), 1.19(3H, t, J=7.7), 1.20(3H, t, J=7.7), 1.4–2.3(5H, m), 2.4–3.0(10H, m), 3.9–4.2(2H, m), 4.09(2H, s), 7.1–7.5(5H, m) | 368 112 | 0.53 |
| 378 | 1.19(3H, t, J=7.6), 1.20(3H, t, J=7.6), 2.4–2.7(14H, m), 3.58(2H, s), 4.09(2H, s), 3.8–4.3(2H, m), 7.1–7.5(7H, m), 8.16(2H, d, J=8.8) | 490 247 191 | 0.49 |
| 380 | 1.21(3H×2, t, J=7.6), 2.4–3.6(14H, m), 4.10(2H, s), 4.0–4.4(2H, m), 6.8–7.5(10H, m) | 431 188,189 175 | 0.63 |
| 384 | 1.20(3H×2, t, J=7.4), 2.2–2.8(10H, m), 3.6–4.3(6H, m), 4.04(2H, s), 7.1–7.4(4H, m) | 392 390 114 | 0.43 |
| 385 | 1.19(3H×2, t, J=7.6), 2.2–2.8(14H, m), 3.46(2H, s), 3.8–4.3(2H, m), 4.04(2H, s), 7.1–7.4(8H, m) | 517 515 513 303 223 | 0.48 |
| 386 | 1.19(3H×2, t, J=7.6), 2.1–2.8(14H, m), 3.46(2H, s), 3.79(3H, s), 3.9–4.2(2H, m), 4.03(2H, s), 6.84(2H, d, J=8.8), 7.1–7.4(6H, m) | 511 509 232 219 | 0.42 |
| 387 | 1.19(3H, t, J=7.1), 1.20(3H, t, J=7.1), 2.3–2.8(14H, m), 3.47(2H, s), 4.05(2H, s), 4.1–4.3(2H, m), 7.52(2H, d, J=8.8), 7.26(4H, s), 8.17(2H, d, J=8.8) | 526 524 247 | 0.43 |
| 454 | 1.23(3H, t, J=7.4), 2.32(3H, s), 2.33(3H, s), 2.4–3.0(13H, m), 4.0–4.2(2H, m) | 265 179 | |
| 455 | 1.22(3H, t, J=7.4), 2.30(3H×2, s), 2.2–3.0(8H, m), 3.44(2H, t, J=5), 3.65(2H, t, J=5), 3.72(2H, s), 4.0–4.2(2H, m), 7.1–7.4(5H, m) | 383 217 139 | |
| 456 | 1.22(3H, t, J=7.4), 2.32(3H×2, s), 2.4–2.9(8H, m), 3.3–3.8(4H, m), 4.0–4.3(2H, m), 7.36(4H, s) | 405 403 251 237 | |
| 457 | 1.23(3H, t, J=7.4), 2.31(3H×2, s), 2.3–2.9(8H, m), 3.51(2H, t, J=5), 3.65(2H, t, J=5), 3.90(2H, s), 4.0–4.2(2H, m), 6.8–7.3(3H, m) | 389 223 | |
| 458 | 1.22(3H, t, J=7.4), 2.32(3H×2, s), 2.4–3.0(8H, m), 3.2–3.5(2H, m), 3.5–3.9(2H, m), 4.0–4.3(2H, m), 7.56(2H, d, J=8.8), 8.28(2H, d, J=8.8) | 414 262 248 | |
| 459 | 1.23(3H, t, J=7.4), 2.31(3H×2, s), 2.4–3.0(8H, m), 3.48(2H, t, J=5), 3.65(2H, t, J=5), 3.81(2H, s), 4.0–4.3(2H, m), 7.41(2H, d, J=8.6), 8.19(2H, d, J=8.6) | 428 265 | |
| 460 | 1.23(3H, t, J=7.4), 2.32(3H×2, s), 2.4–2.9(8H, m), 3.5–3.7(4H, m), 3.83(3H, s), 4.0–4.3(2H, m), 6.8–7.0(2H, m), 7.3–7.5(2H, m) | 399 247 233 | |
| 461 | 1.22(3H, t, J=7.4), 2.31(3H×2, s), 2.2–3.0(8H, m), 3.1–3.4(2H, m), 3.6–3.9(2H, m), 3.85(3H, s), 3.88(3H, s), 4.0–4.3(2H, m), 6.7–7.2(3H, m) | 429 277 263 164 | |
| 462 | 1.22(3H, t, J=7.4), 2.31(3H×2, s), 2.2–3.0(8H, m), 3.1–3.4(2H, m), 3.6–3.8(2H, m), 3.82(3H×2, s), 4.0–4.3(2H, m), 6.5–6.7(2H, m), 7.0–7.2(1H, m) | 429 277 263 164 | |
| 463 | 1.23(3H, t, J=7.4), 2.32(3H×2, s), 2.4–3.0(8H, m), 3.7–3.9(4H, m), 3.90(3H, s), 3.91(3H, s), 4.0–4.3(2H, m), 6.7–7.0(3H, m) | 429 277 263 164 | |
| 464 | 1.22(3H, t, J=7.4), 2.32(3H×2, s), 2.4–3.0(8H, m), 3.4–3.8(4H, m), 3.87(3H×2, s), 4.0–4.3(2H, m), 6.61(2H, s) | 459 306 195 | |
| 465 | 1.17(3H, t, J=7.4), 2.27(3H×2, s), 2.4–2.9(8H, m), 2.9–3.1(4H, m), 3.9–4.2(2H, m), 7.4–7.8(4H, m) | 441 439 287 283 | |
| 467 | 1.18(3H×2, t, J=7.4), 2.3–2.8(14H, m), 3.51(2H, s), 3.9–4.2(2H, m), 4.03(2H, s), 7.1–7.4(9H, m) | 481(M⁺+1) 479 | 0.42 |
| 468 | 1.19(3H, t, J=7.4), 1.20(3H, t, J=7.4), 2.3–2.8(14H, m), 3.58(2H, s), 3.8–4.0(2H, m), 4.05(2H, s), 4.1–4.3(2H, m), 7.0–7.5(2H, m), 7.26(4H, s), 8.17(2H, d, J=8.8) | 526(M⁺+1) 524 | |

TABLE 27-continued

| Compound Nos. | NMR (CDCl₃, TMS) δ | Mass | TLC |
|---|---|---|---|
| | | 247 | |
| 470 | 1.6–2.0(4H, m), 2.4–2.8(10H, m), 3.5–3.8(4H, m), 3.9–4.2(2H, m), 4.09(2H, s), 7.0–7.5(5H, m) | 354(M⁺ +1) 114 | |
| 471 | 1.6–2.0(4H, m), 2.3–2.8(14H, m), 3.50(2H, s), 3.9–4.1(2H, m), 4.09(2H, s), 7.1–7.5 (10H, m) | 443(M⁺ +1) 189 | |
| 472 | 1.6–2.0(4H, m), 2.5–2.9(10H, m), 3.0–3.3(4H, m), 3.9–4.2(2H, m), 4.10(2H, s), 6.7–7.5(10H, m) | 429(M⁺ +1) 175 | |
| 473 | 1.6–2.0(4H, m), 2.3–2.8(14H, m), 3.45(2H, s), 3.9–4.1(2H, m), 4.09(2H, s), 7.1–7.5 (5H, m), 7.25(4H, s) | 479(M⁺ +1) 477 223 | |
| 474 | 1.6–2.0(4H, m), 2.3–2.8(14H, m), 3.44(2H, s), 3.79(3H, s), 3.9–4.1(2H, m), 4.09( 2H, s), 6.84(2H, d, J=8.8), 7.0–7.5(7H, m) | 473(M⁺ +1) 219 | |
| 475 | 1.6–2.0(4H, m), 2.3–2.8(14H, m), 3.46(2H, s), 3.9–4.1(2H, m), 4.09(2H, s), 6.8–7.5 (9H, m) | 461(M⁺ +1) 207 | |
| 476 | 1.6–1.9(4H, m), 2.4–2.8(14H, m), 2.9–3.2(4H, m), 4.6–4.8(4H, m), 3.9–4.2(2H, m), 7.1–7.4(5H, m) | 368(M⁺ +1) 114 | |
| 477 | 1.6–1.9(4H, m), 2.4–2.8(14H, m), 2.9–3.2(4H, m), 3.52(2H, s), 3.9–4.2(2H, m), 7.1–7.4(10H, m) | 457(M⁺ +1) 189 | |
| 478 | 1.6–2.0(4H, m), 2.4–2.9(10H, m), 2.9–3.4(8H, m), 4.0–4.2(2H, m), 6.7–7.4(10H, m) | 443(M⁺ +1) 175 | |
| 479 | 1.6–2.0(4H, m), 2.3–2.8(14H, m), 2.9–3.2(4H, m), 3.47(2H, s), 3.9–4.2(2H, m), 7.0–7.4(5H, m), 7.26(4H, s) | 493(M⁺ +1) 491 236 223 | |
| 480 | 1.6–2.0(4H, m), 2.3–2.8(14H, m), 2.9–3.2(4H, m), 3.45(2H, s), 3.79(3H, s), 3.9–4.2 (2H, m), 6.92(2H, d, J=8.8), 7.0–7.4(7H, m) | 407(M⁺ +1) 232 219 | |
| 481 | 1.23(3H, t, J=7.4), 1.6–2.0(4H, m), 2.3–3.0(12H, m), 3.5–3.8(4H, m), 3.9–4.2(2H, m) | 292(M⁺ +1) | |
| 482 | 1.23(3H, t, J=7.4), 1.6–2.0(4H, m), 2.3–3.0(16H, m), 3.47(2H, s), 3.9–4.2(2H, m), 7.27(4H, s) | 417(M⁺ +1) 415 223 | |
| 483 | 1.23(3H, t, J=7.4), 1.6–2.0(4H, m), 2.4–3.0(16H, m), 3.52(2H, s), 3.9–4.2(2H, m), 7.2–7.3(5H, m) | 381(M⁺ +1) 189 | |
| 484 | 1.24(3H, t, J=7.4), 1.6–2.0(4H, m), 2.6–3.0(12H, m), 3.1–3.3(4H, m), 4.0–4.3(2H, m), 6.7–7.4(5H, m) | 367(M⁺ +1) 175 | |
| 485 | 1.23(3H, t, J=7.4), 1.6–2.0(6H, m), 2.4–3.0(16H, m), 3.59(2H, s), 3.9–4.2(2h, m), 7.27(4H, s) | 431(M⁺ +1) 429 237 | |
| 486 | 1.22(3H, t, J=7.4), 1.6–2.0(4H, m), 2.3–3.0(16H, m), 3.47(2H, s), 3.80(3H, s), 3.9–4.2(2H, m), 6.84(2H, d, J=8.8), 7.23(2H, d, J=8.8) | 411(M⁺ +1) 219 | |
| 487 | 0.88(3H, t, J=6), 1.1–1.5(20H, m), 1.5–2.0(10H, m), 2.4–2.9(14H, m), 3.51(2H, s), 3.9–4.2(2H, m), 7.29(5H, s) | 549(M⁺ +1) 202 121 | |
| 488 | 0.88(3H, t, J=6), 1.1–1.5(22H, m), 1.5–2.0(10H, m), 2.5–3.0(14H, m), 3.72(2H, s), 3.9–4.2(2H, m), 7.51(2H, d, J=8.8), 8.17(2H, d, J=8.8) | 608(M⁺ +1) 473 | |
| 489 | 0.88(3H, t, J=6), 1.1–1.5(22H, m), 1.5–2.0(10H, m), 2.4–2.9(14H, m), 3.54(2H, s), 3.9–4.2(2H, m), 7.27(4H, s) | 599 597 | |
| 490 | 0.87(3H, t, J=6), 1.1–1.5(22H, m), 1.5–2.0(10H, m), 2.5–3.0(14H, m), 3.59(2H, s), 3.80(3H, s), 3.9–4.2(2H, m), 6.84(2H, d, J=8.8), 7.24(2H, d, J=8.8) | 593(M⁺ +1) 246 101 | |
| 611 | 2.30(3H, s), 2.34(3H, s), 2.4(3H, s), 2.5–3.0(9H, m), 4.0–4.2(2H, m) | 250(M⁺ +1) | 0.04 |
| 612 | 2.44(3H×2, s), 3.91(2H, t, J=6.3), 4.43(2H, t, J=6.3), 8.1–8.3(5H, m) | 265 263 (M⁺ +1) | 0.79 |
| 613 | 2.33(3H×2, s), 3.80(2H, t, J=5.4), 4.09(2H, s), 4.29(2H, t, J=5.4), 7.1–7.5(5H, m) | 278 276 (M⁺ +1) | |
| 614 | 0.99(3H, t, J=7.3), 1.5–1.9(6H, m), 2.5–2.9(6H, m), 3.38(1H, bs), 3.8–4.0(2H, m), 4.1–4.3(2H, m) | 237(M⁺ +1) 164 | 0.34 |
| 615 | 0.99(3H, t, J=7.3), 1.5–2.0(6H, m), 2.3–2.8(6H, m), 3.1–3.4(2H, m), 4.0–4.2(2H, m), 7.1–7.6(5H, m) | 329(M⁺ +1) 319 | |
| 616 | 0.99(3H, t, J=7.2), 1.5–2.0(2H, m), 2.33(3H×2, s), 2.74(2H, t, J=7.7), 3.8–4.0(2H, m), 4.1–4.3(2H, m) | 211(M⁺ +1) | 0.29 |
| 617 | 0.94(3H×2, d, J=6.6), 1.8–2.4(1H, m), 2.33(3H×2, s), 2.64(2H, d, J=7.1), 3.8–4.0(2H, m), 4.1–4.3(2H, m) | 255(M⁺ +1) | 0.29 |
| 618 | 0.95(3H×2, d, J=6.6), 1.6–2.0(4H, m), 2.0–2.4(1H, m), 2.5–2.8(6H, m), 3.8–4.0(2H, m), 4.1–4.3(2H, m) | 251(M⁺ +1) | 0.34 |
| 619 | 0.93(3H×2, d, J=6.4), 2.0–2.4(1H, m), 2.31(2H×2, s), 2.3–2.7(12H, m), 3.46(2H, s), 3.9–4.3(2H, m), 6.8–7.1(2H, m), 7.1–7.4(2H, m) | 401(M⁺ +1) 207 | 0.34 |
| 620 | 1.00(3H, t, J=7.3), 1.21(3H×3, t, J=7.5), 1.5–1.9(2H, m), 2.4–2.9(6H, m), 3.9–4.0( 2H, m), 4.1–4.3(2H, m) | 239(M⁺ +1) | 0.44 |
| 621 | 0.94(3H, t, J=7.0), 1.2–2.0(8H, m), 2.5–2.9(6H, m), 3.8–4.0(2H, m), 4.0–4.3(2H, m) | 251(M⁺ +1) | 0.32 |
| 622 | 1.20(3H×2, d, J=6.8), 2.32(3H×2, s), 3.41(1H, sept, J=6.8), 3.8–4.1(2H, m), 4.1–4.3( m) | 211(M⁺ +1) | 0.36 |
| 623 | 0.79(3H, t, J=7.3), 1.18*3H, d, J=6.9), 1.3–2.0(3H, t, J=7.4), 1.11(3H, d, J=6.9), 1.3–2.0(2H, m), 2.32(3H×2, s), 3.22(1H, sept, J=6.9), 3.94(2H, t, J=5.2), 4.26(2H, t, J= 5.2) | 225(M⁺ +1) | 0.35 |
| 624 | 0.93(3H, t, J=6.7), 1.2–2.0(4H, m), 2.33(3H×2, s), 2.77(2H, t, J=5.6), 3.7–4.0(2H, m), 4.1–4.3(2H, m) | 225(M⁺ +1) | 0.33 |
| 625 | 1.1–1.4(12H, m), 2.55(2H, t, J=7.6), 2.72(2H, t, J=7.6), 3.41(1H, sept, J=6.9), 3.72 (1H, bs), 3.8–4.1(2H, m), 4.26(2H, t, J=5.1) | 239(M⁺ +1) 195 | 0.40 |
| 626 | 0.95(3H×2, d, J=6.4), 1.21(3H×2, t, J=7.4), 2.0–2.4(1H, m), 2.4–2.9(6H, m), 3.8–4.0( 2H, m), 4.1–4.3(2H, m) | 253(M⁺ +1) 210 | 0.34 |

TABLE 27-continued

| Compound Nos. | NMR (CDCl₃, TMS) δ | Mass | TLC |
|---|---|---|---|
| 627 | 0.88(3H, t,J=7.5), 1.0-1.4(9H, m), 1.2-2.2(2H, m), 2.4-2.8(4H, m), 3.1-3.4(1H, m), 3.8-4.0(2H, m), 4.1-4.3(2H, m) | 253(M⁺ +1) | 0.34 |
| 628 | 0.97(3H×2, d, J=6.4), 1.21(3H×2, t, J=7.4), 1.2-1.9(4H, m), 2.4-2.9(6H, M), 3.8-4.0(2H, m) | 253(M⁺ +1) 210 | 0.37 |
| 629 | 1.1-1.4(9H, m), 2.4-2.6(6H, m), 3.93(3H, t, J=5.1), 4.20(3H, t, J=5.1) | 225(M⁺ +1) 130 | 0.33 |
| 630 | 1.21(3Ht, J=7.5), 2.32(3H×2, s), 2.77(2H, q, J=7.5), 3.92(2H, t, J=5.0), 4.24(2H, t, J=5.0) | 197(M⁺ +1) 153 | |
| 631 | 0.89(3H, t, J=6.6), 1.2-1.9(10H, m), 2.5-2.9(6H, m), 3.8-4.0(2H, m), 4.0-4.3(3H, m) | 265(M⁺ +1) 239 208 | 0.32 |
| 632 | 0.88(3H, t, J=6.6), 1.2-1.9(12H, m), 2.5-2.9(6H, m), 3.8-4.0(2H, m), 4.0-4.3(2H, m) | 265(M⁺ +1) 219 208 | 0.33 |
| 633 | 0.87(3H, t, J=6), 1.1-2.0(14H, m), 2.5-2.9(6H, m), 3.8-4.0(2H, m), 4.0-4.3(2H, m) | 293(M⁺ +1) 247 208 | 0.34 |
| 634 | 0.87(3H, t, J=6), 1.1-2.0(16H, m), 2.5-2.9(6H, m), 3.8-4.0(2H, m), 4.0-4.3(2H, m) | 307(M⁺ +1) 208 | 0.38 |
| 635 | 0.87(3H, t, J=6), 1.1-2.0(18H, m), 2.5-2.9(6H, m), 3.3(1H, bs), 3.8-4.0(2H, m) 4.0-4.3(2H, m) | 321(M⁺ +1) | 0.39 |
| 636 | 0.87(3H, t, J=6), 1.2-2.0(20H, m), 2.5-2.9(6H, m), 3.3(1H, bs), 3.8-4.0(2H, m) 4.1-4.3(2H, m) | 335(M⁺ +1) 208 | 0.35 |
| 637 | 0.88(3H, t, J=6), 1.1-2.0(24H, m), 2.5-2.9(6H, m), 3.34(1H, bs), 3.8-4.0(2H, m) 4.0-4.3(2H, m) | 363(M⁺ +1) | 0.41 |
| 638 | 0.88(3H, t, J=6), 1.1-2.0(28H, m), 2.5-2.9(6H, m), 3.20(1H, bs), 3.8-4.0(2H, m) 4.0-4.3(2H, m) | 391(M⁺ +1) | 0.41 |
| 639 | 0.88(3H, t, J=6), 1.1-2.0(32H, m), 2.5-2.9(6H, m), 3.25(1H, bs), 3.8-4.0(2H, m) 4.0-4.3(2H, m) | 419(M⁺ +1) | 0.46 |
| 640 | 1.18(3H, t, J=7.6), 1.20(3H, t, J=7.6), 2.58(2H, q, J=7.6), 2.68(2H, q, J=7.6), 3.89(2H, t, J=6.6), 4.08(2H, s), 4.19(2H, t, J=6), 7.0-7.4(5H, m) | 286(M⁺ +1) | 0.31 |
| 641 | 1.19(3H, t, J=7.7), 1.20(3H, t, J=7.7), 2.58(2H, q, J=7.7), 2.69(2H, q, J=7.7), 3.8-4.0(2H, m), 4.05(2H, s), 4.21(2H, t, J=5.2), 7.1-7.4(4H, m) | 323 321 | 0.26 |
| 642 | 2.30(3H, s), 2.34(3H, s), 2.41(3H, s), 2.5-3.0(8H, m), 4.0-4.2(2H, m) | 250(M⁺ +1) | 0.06 |
| 643 | 1.6-1.9(4H, m), 2.5-2.8(4H, m), 3.7-4.0(2H, m), 4.09(2H, s), 4.0-4.2(2H, m), 7.0-7.4(5H, m) | 255(M⁺ +1) | |
| 644 | 1.6-2.0(4H, m), 2.5-2.8(4H, m), 3.79(2H, t, J=7), 4.10(2H, s), 4.23(2H, t, J=7), 7.0-7.5(5H, m) | 305 303 267 239 | |
| 645 | 1.6-2.0(4H, m), 2.5-2.8(4H, m), 3.03(2H×2, s), 3.90(2H, t, J=5), 7.0-7.4(5H, m) | 299 | |
| 646 | 1.22(3H, t, J=7.3), 1.7-4.0(4H, m), 2.6-2.8(4H, m), 3.78(2H, q, J=7.3), 3.7-4.0(2H, m), 4.0-4.3(2H, m) | 223 | |
| 647 | 1.19(3H, t, J=7.7), 1.21(3H, t, J=7.7), 2.61(2H, q, J=7.7), 2.74(2H, q, J=7.7), 3.8-4.4(4H, m), 7.1-7.5(4H, m) | 343 341 339(M⁺ +1) | |

What is claimed is:
1. A compound of the formula

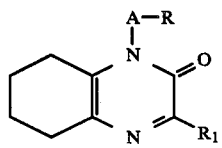

wherein

A is lower alkylene; R₁ is selected from the group consisting of alkyl, phenyl-lower alkyl, and substituted phenyl-lower alkyl; and R is selected from the group consisting of hydroxyl, halogen, lower alkanoyloxy, R₄-carbamoyloxy and arylthio, in which R₄ is lower alkyl or aryl; and pharmaceutically acceptable salts thereof.

2. The compound of claim 1 wherein R is hydroxyl.
3. The compound of claim 1 wherein R is halogen.
4. The compound of claim 1 wherein R is lower alkanoyloxy.
5. The compound of claim 1 wherein R is R₄-carbamoyloxy wherein R₄ is lower alkyl or aryl.
6. The compound of claim 1 wherein R is arylthio.

* * * * *